United States Patent
Sheng et al.

(10) Patent No.: US 10,689,459 B2
(45) Date of Patent: Jun. 23, 2020

(54) TREATMENT OF BREAST CANCER BRAIN METASTASES

(71) Applicants: THE GENERAL HOSPITAL CORPORATION, Boston, MA (US); NOVARTIS AG, Basel (CH)

(72) Inventors: Qing Sheng, Sharon, MA (US); Rakesh K. Jain, Freemont, CA (US); Vasileios Askoxylakis, Cambridge, MA (US); Gino B. Ferraro, Somerville, MA (US); Dai Fukumura, Newton, MA (US); David P. Kodack, Boston, MA (US)

(73) Assignees: Novartis AG, Basel (CH); The General Hospital Corporation, Boston, MA (US)

( * ) Notice: Subject to any disclaimer, the term of this patent is extended or adjusted under 35 U.S.C. 154(b) by 156 days.

(21) Appl. No.: 15/535,405

(22) PCT Filed: Dec. 10, 2015

(86) PCT No.: PCT/IB2015/059252
§ 371 (c)(1),
(2) Date: Jun. 12, 2017

(87) PCT Pub. No.: WO2016/092508
PCT Pub. Date: Jun. 16, 2016

(65) Prior Publication Data
US 2019/0211110 A1    Jul. 11, 2019

Related U.S. Application Data

(60) Provisional application No. 62/091,200, filed on Dec. 12, 2014.

(51) Int. Cl.
*A61K 39/395* (2006.01)
*C07K 16/32* (2006.01)
*A61K 31/5377* (2006.01)
*C07K 16/30* (2006.01)
*A61K 45/06* (2006.01)
*A61P 35/04* (2006.01)
*A61K 39/00* (2006.01)

(52) U.S. Cl.
CPC .......... *C07K 16/32* (2013.01); *A61K 31/5377* (2013.01); *A61K 39/39558* (2013.01); *A61K 45/06* (2013.01); *A61P 35/04* (2018.01); *C07K 16/30* (2013.01); *A61K 2039/505* (2013.01); *A61K 2039/545* (2013.01); *C07K 2317/565* (2013.01); *C07K 2317/73* (2013.01); *C07K 2317/76* (2013.01)

(58) Field of Classification Search
CPC ..................................................... C07K 16/32
See application file for complete search history.

(56) References Cited

U.S. PATENT DOCUMENTS

| 8,735,551 B2 | 5/2014 | Garner et al. |
| 9,192,663 B2 | 11/2015 | Elis et al. |
| 10,077,317 B2 * | 9/2018 | Garner ............ A61K 39/39558 |
| 2012/0107306 A1 * | 5/2012 | Elis ................. A61K 39/39558 424/133.1 |
| 2016/0158358 A1 | 6/2016 | Elis et al. |
| 2017/0166653 A1 | 6/2017 | Garner et al. |

FOREIGN PATENT DOCUMENTS

| WO | WO-2007084786 A1 * | 7/2007 | .......... C07D 401/04 |
| WO | 2009/109605 A1 | 9/2009 | |
| WO | 2012022814 A1 | 2/2012 | |
| WO | 2013084147 A2 | 6/2013 | |
| WO | 2014/028566 A1 | 2/2014 | |
| WO | 2014177915 A1 | 11/2014 | |
| WO | 2016011167 A1 | 1/2016 | |

OTHER PUBLICATIONS

Li, J. et al., "Dual inhibition of EGFR at protein and activity level via combinatorial blocking of PI4KIIalpha as antitumor strategy", Protein & Cell, 5(6):457-468. (2014).
She, Q et al., "Resistance to gefitinib in PTEN-Null Her overexpressing tumor cells can be overcome through restoration of PTEN function or pharmacologic modulation of constitutive phosphatidylinositol 3'-kinase/Akt pathway signaling", Clinical Cancer Research, 9:4340-4346. (2003).
Altundag, K. et al., "Rationale for the use of trastuzumab in patients with cerebral metastases who previously receive trastuzumab-based therapy for metastatic breast cancer", Breast, 14:425. (2005).
Da Silva et al., "HER3 and downstream pathways are involved in colonization of brain metastases from breast cancer", Breast Cancer Research, 2010, 12:R46.

* cited by examiner

*Primary Examiner* — Sheela J. Huff
(74) *Attorney, Agent, or Firm* — Kun Wang; Genomics Institute of the Novartis Research Foundation

(57) ABSTRACT

The present invention relates to a pharmaceutical combination which comprises (a) a phosphatidylinositol 3-kinase inhibitor or pharmaceutically acceptable salt thereof, and (b) a Her3 antagonist, for simultaneous, separate or sequential administration for the treatment of breast cancer brain metastases; a method of treating a subject having a breast cancer brain metastases comprising administration of said combination to a subject in need thereof; use of such combination for the treatment of breast cancer brain metastases; and a commercial package comprising such combination.

14 Claims, 3 Drawing Sheets
Specification includes a Sequence Listing.

TREATMENT OF BREAST CANCER BRAIN METASTASES

This application is a U.S. National Phase filing of International Application No. PCT/162015/059525 filed 10 Dec. 2015, which claims priority to U.S. Application No. 62/091,200 filed 14 Dec. 2014, the contents of which are incorporated herein by reference in their entirety.

FIELD OF THE INVENTION

The present invention relates to a pharmaceutical combination which comprises (a) a phosphatidylinositol 3-kinase inhibitor or pharmaceutically acceptable salt thereof, and (b) a Her3 antagonist, for simultaneous, separate or sequential administration for the treatment of metastatic breast cancer in the brain (referred to herein as breast cancer brain metastases).

BACKGROUND

Major progress has been achieved in developing and optimizing HER2-targeted therapies for breast cancer. Examples of FDA-approved drugs with significant clinical efficacy for metastatic disease include the anti-HER2 antibody trastuzumab, the dual EGFR-HER2 kinase inhibitor lapatinib, the anti-HER2-HER3 dimerization inhibitor pertuzumab, and the antibody-drug conjugate T-DM1 (Krop, I. E., et al. *Lancet Oncol* (2014); Slamon, D. J., et al. *The New England journal of medicine* 344, 783-792 (2001)). Clinical data reveal an increased incidence of brain metastases (BM) after adjuvant trastuzumab therapy (Olson, E. M., et al. Annals of oncology: official journal of the European Society for Medical Oncology/ESMO 24, 1526-1533 (2013). This incidence is high as 50% in patients with advanced disease. Established BM often exhibit resistance to trastuzumab, a phenomenon which has been mostly attributed to inadequate penetration of the antibody through the blood-brain barrier (BBB) (Lampson, L. A. *mAbs* 3, 153-160 (2011). However, despite adequate drug delivery, the efficacy of small molecules on BM is also very limited and can only be marginally increased through the addition of further therapeutic modalities (Lin, N. U., et al. Journal of clinical oncology 26, 1993-1999 (2008); Lin, N. U., et al. Clinical cancer research: an official journal of the American Association for Cancer Research 15, 1452-1459 (2009); Bachelot, T., et al. The lancet oncology 14, 64-71 (2013)). Brain metastases is a devastating progression of breast cancer. Treatment options are limited, and the same anti-HER2 therapies that slow growth systemically do not typically control brain metastases. Thus, there is a need to identify a drug(s) that can be useful for treating breast cancer brain metastases.

SUMMARY OF THE INVENTION

Breast cancer brain metastases is the result of metastatic breast cancer in the brain. The present invention is based on the surprising finding that a combination of a phosphatidylinositol 3-kinase inhibitor and a Her3 antagonist can be used to treat breast cancer brain metastases.

In one aspect, the present invention pertains to a pharmaceutical combination comprising (a) a phosphatidylinositol 3-kinase inhibitor selected from the group consisting of a compound of formula (I)

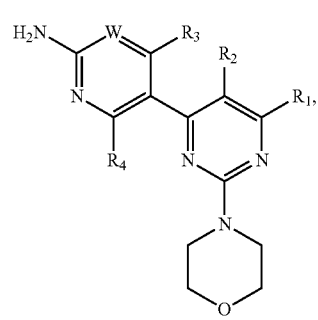

wherein
wherein W is $CR_w$ or N, wherein
$R_w$ is selected from the group consisting of:
(1) hydrogen,
(2) cyano,
(3) halogen,
(4) methyl,
5) trifluoromethyl,
(6) sulfonamide;
$R_1$ is selected from the group consisting of:
(1) hydrogen,
(2) cyano,
(3) nitro,
(4) halogen,
(5) substituted and unsubstituted alkyl,
(6) substituted and unsubstituted alkenyl,
(7) substituted and unsubstituted alkynyl,
(8) substituted and unsubstituted aryl,
(9) substituted and unsubstituted heteroaryl,
(10) substituted and unsubstituted heterocyclyl,
(11) substituted and unsubstituted cycloalkyl,
(12) —$COR_{1a}$,
(13) —$CO_2R_{1a}$,
(14) —$CONR_{1a}R_{1b}$,
(15) —$NR_{1a}R_{1b}$,
(16) —$NR_{1a}COR_{1b}$,
(17) —$NR_{1a}SO_2R_{1b}$,
(18) —$OCOR_{1a}$,
(19) —$OR_{1a}$,
(20) —$SR_{1a}$,
(21) —$SOR_{1a}$,
(23) —$SO_2NR_{1a}R_{1b}$ wherein
$R_{1a}$ and $R_{1b}$ are independently selected from the group consisting of:
(a) hydrogen,
(b) substituted or unsubstituted alkyl,
(c) substituted and unsubstituted aryl,
(d) substituted and unsubstituted heteroaryl,
(e) substituted and unsubstituted heterocyclyl, and
(f) substituted and unsubstituted cycloalkyl;
$R_2$ is selected from the group consisting of:
(1) hydrogen,
(2) cyano,
(3) nitro,
(4) halogen,
(5) hydroxy,
(6) amino,
(7) substituted and unsubstituted alkyl,
(8) —$COR_{2a}$, and
(9) —$NR_{2a}COR_{2b}$, wherein
$R_{2a}$ and $R_{2b}$ are independently selected from the group consisting of:
(a) hydrogen, and
(b) substituted or unsubstituted alkyl;

$R_3$ is selected from the group consisting of:
(1) hydrogen,
(2) cyano,
(3) nitro,
(4) halogen,
(5) substituted and unsubstituted alkyl,
(6) substituted and unsubstituted alkenyl,
(7) substituted and unsubstituted alkynyl,
(8) substituted and unsubstituted aryl,
(9) substituted and unsubstituted heteroaryl,
(10) substituted and unsubstituted heterocyclyl,
(11) substituted and unsubstituted cycloalkyl,
(12) —$COR_{3a}$,
(14) —$NR_{3a}R_{3b}$
(13) —$NR_{3a}COR_{3b}$,
(15) —$NR_{3a}SO_2R_{3b}$,
(16) —$OR_{3a}$,
(17) —$SR_{3a}$,
(18) —$SOR_{3a}$,
(19) —$SO_2R_{3a}$, wherein
$R_{3a}$, and $R_{3b}$ are independently selected from the group consisting of:
(a) hydrogen,
(b) substituted or unsubstituted alkyl,
(c) substituted and unsubstituted aryl,
(d) substituted and unsubstituted heteroaryl,
(e) substituted and unsubstituted heterocyclyl, and
(f) substituted and unsubstituted cycloalkyl; and
$R_4$ is selected from the group consisting of
(1) hydrogen, and
(2) halogen.
or a pharmaceutically acceptable salt thereof and (b) a Her3 antagonist such as a Her3 antibody or fragment thereof, wherein the antibody or fragment recognizes a conformational epitope of a HER3 receptor comprising amino acid residues 265-277, and 315 within domain 2 and amino acid residues 571, 582-584, 596-597, 600-602, and 609-615 within domain 4 of the HER3 receptor of SEQ ID NO: 1, and wherein the antibody or fragment thereof blocks both ligand-dependent and ligand-independent signal transduction, for simultaneous, separate or sequential administration for the treatment of breast cancer brain metastases.

In one embodiment, the compound of formula (I) is 5-(2,6-di-morpholin-4-yl-pyrimidin-4-yl)-4-trifluoromethyl-pyridin-2-ylamine or its hydrochloride salt.

In another embodiment, the Her3 antibody or fragment comprises a heavy chain variable region and a light chain variable region as shown in Table 1 below. In another embodiment, the Her3 antibody or fragment comprises a heavy chain variable region CDR1 of SEQ ID NO: 128; CDR2 of SEQ ID NO: 129; CDR3 of SEQ ID NO: 130; and a light chain variable region CDR1 of SEQ ID NO: 131; CDR2 of SEQ ID NO: 132; and CDR3 of SEQ ID NO: 133. In another example, the HER3 antagonist can be MOR10703, the sequence of which is shown in Table 1 below.

In another embodiment, the pharmaceutical combination of the invention includes 5-(2,6-di-morpholin-4-yl-pyrimidin-4-yl)-4-trifluoromethyl-pyridin-2-ylamine or its hydrochloride salt and an antibody or fragment thereof that recognizes a conformational epitope of a HER3 receptor comprising amino acid residues 265-277, and 315 within domain 2 and amino acid residues 571, 582-584, 596-597, 600-602, and 609-615 within domain 4 of the HER3 receptor of SEQ ID NO: 1, and wherein the antibody or fragment thereof blocks both ligand-dependent and ligand-independent signal transduction.

In another embodiment, the pharmaceutical combination of the invention includes 5-(2,6-di-morpholin-4-yl-pyrimidin-4-yl)-4-trifluoromethyl-pyridin-2-ylamine or its hydrochloride salt and an Her3 antibody or fragment comprising a heavy chain variable region CDR1 of SEQ ID NO: 128; CDR2 of SEQ ID NO: 129; CDR3 of SEQ ID NO: 130; and a light chain variable region CDR1 of SEQ ID NO: 131; CDR2 of SEQ ID NO: 132; and CDR3 of SEQ ID NO: 133.

In another aspect, the present invention relates to the use of a pharmaceutical combination comprising (a) a phosphatidylinositol 3-kinase selected from the group consisting of a compound of formula (I) or pharmaceutically acceptable salt thereof, and (b) a Her3 antagonist such as a Her3 antibody or fragment thereof, for the treatment of breast cancer brain metastases and/or for the preparation of a medicament for the treatment of a breast cancer brain metastases.

In one embodiment, the breast cancer brain metastases is a HER2-positive breast cancer brain metastases.

In another aspect, the present invention pertains to a method of treating breast cancer brain metastases comprising administering (a) a phosphatidylinositol 3-kinase inhibitor is selected from the group consisting of a compound of formula (I)

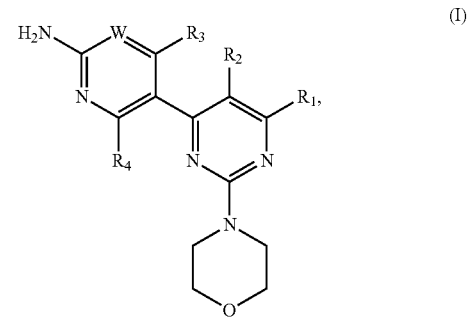

wherein
wherein W is $CR_w$ or N, wherein
$R_w$ is selected from the group consisting of:
(1) hydrogen,
(2) cyano,
(3) halogen,
(4) methyl,
5) trifluoromethyl,
(6) sulfonamide;
$R_1$ is selected from the group consisting of:
(1) hydrogen,
(2) cyano,
(3) nitro,
(4) halogen,
(5) substituted and unsubstituted alkyl,
(6) substituted and unsubstituted alkenyl,
(7) substituted and unsubstituted alkynyl,
(8) substituted and unsubstituted aryl,
(9) substituted and unsubstituted heteroaryl,
(10) substituted and unsubstituted heterocyclyl,
(11) substituted and unsubstituted cycloalkyl,
(12) —$COR_{1a}$,
(13) —$CO_2R_{1a}$,
(14) —$CONR_{1a}R_{1b}$,
(15) —$NR_{1a}R_{1b}$,
(16) —$NR_{1a}COR_{1b}$,
(17) —$NR_{1a}SO_2R_{1b}$,

(18) —OCOR$_{1a}$,
(19) —OR$_{1a}$,
(20) —SR$_{1a}$,
(21) —SOR$_{1a}$,
(23) —SO$_2$NR$_{1a}$R$_{1b}$ wherein R$_{1a}$, and R$_{1b}$ are independently selected from the group consisting of:
(a) hydrogen,
(b) substituted or unsubstituted alkyl,
(c) substituted and unsubstituted aryl,
(d) substituted and unsubstituted heteroaryl,
(e) substituted and unsubstituted heterocyclyl, and
(f) substituted and unsubstituted cycloalkyl;

R$_2$ is selected from the group consisting of:
(1) hydrogen,
(2) cyano,
(3) nitro,
(4) halogen,
(5) hydroxy,
(6) amino,
(7) substituted and unsubstituted alkyl,
(8) —COR$_{2a}$, and
(9) —NR$_{2a}$COR$_{2b}$, wherein R$_{2a}$, and R$_{2b}$ are independently selected from the group consisting of:
(a) hydrogen, and
(b) substituted or unsubstituted alkyl;

R$_3$ is selected from the group consisting of:
(1) hydrogen,
(2) cyano,
(3) nitro,
(4) halogen,
(5) substituted and unsubstituted alkyl,
(6) substituted and unsubstituted alkenyl,
(7) substituted and unsubstituted alkynyl,
(8) substituted and unsubstituted aryl,
(9) substituted and unsubstituted heteroaryl,
(10) substituted and unsubstituted heterocyclyl,
(11) substituted and unsubstituted cycloalkyl,
(12) —COR$_{3a}$,
(14) —NR$_{3a}$R$_{3b}$
(13) —NR$_{3a}$COR$_{3b}$,
(15) —NR$_{3a}$SO$_2$R$_{3b}$,
(16) —OR$_{3a}$,
(17) —SR$_{3a}$,
(18) —SOR$_{3a}$,
(19) —SO$_2$R$_{3a}$, wherein R$_{3a}$, and R$_{3b}$ are independently selected from the group consisting of:
(a) hydrogen,
(b) substituted or unsubstituted alkyl,
(c) substituted and unsubstituted aryl,
(d) substituted and unsubstituted heteroaryl,
(e) substituted and unsubstituted heterocyclyl, and
(f) substituted and unsubstituted cycloalkyl; and R$_4$ is selected from the group consisting of
(1) hydrogen, and
(2) halogen.

or a pharmaceutically acceptable salt thereof and (b) a Her3 antibody or fragment thereof, wherein the antibody or fragment recognizes a conformational epitope of a HER3 receptor comprising amino acid residues 265-277, and 315 within domain 2 and amino acid residues 571, 582-584, 596-597, 600-602, and 609-615 within domain 4 of the HER3 receptor of SEQ ID NO: 1, and wherein the antibody or fragment thereof blocks both ligand-dependent and ligand-independent signal transduction. In one embodiment, the phosphatidylinositol 3-kinase inhibitor is 5-(2,6-di-morpholin-4-yl-pyrimidin-4-yl)-4-trifluoromethyl-pyridin-2-ylamine or its hydrochloride salt and the Her3 antibody or fragment comprises a heavy chain variable region CDR1 of SEQ ID NO: 128; CDR2 of SEQ ID NO: 129; and CDR3 of SEQ ID NO: 130; and a light chain variable region CDR1 of SEQ ID NO: 131; CDR2 of SEQ ID NO: 132; and CDR3 of SEQ ID NO: 133. In another example, the HER3 antibody can be any antibody shown in Table 1 such as MOR10703, the sequence of which is shown in Table 1 below. The combination can be administered simultaneous, separate or sequential.

In yet another aspect, the present invention pertains to a method of treating breast cancer brain metastases comprising administering (a) a phosphatidylinositol 3-kinase inhibitor is 5-(2,6-di-morpholin-4-yl-pyrimidin-4-yl)-4-trifluoromethyl-pyridin-2-ylamine or a pharmaceutically acceptable salt thereof and (b) an Her3 antibody or fragment thereof, wherein the antibody or fragment recognizes a conformational epitope of a HER3 receptor comprising amino acid residues 265-277, and 315 within domain 2 and amino acid residues 571, 582-584, 596-597, 600-602, and 609-615 within domain 4 of the HER3 receptor of SEQ ID NO: 1, and wherein the antibody or fragment thereof blocks both ligand-dependent and ligand-independent signal transduction. In one embodiment, the phosphatidylinositol 3-kinase inhibitor is 5-(2,6-di-morpholin-4-yl-pyrimidin-4-yl)-4-trifluoromethyl-pyridin-2-ylamine or its hydrochloride salt and the Her3 antibody or fragment comprises a heavy chain variable region CDR1 of SEQ ID NO: 128; CDR2 of SEQ ID NO: 129; CDR3 of SEQ ID NO: 130; and a light chain variable region CDR1 of SEQ ID NO: 131; CDR2 of SEQ ID NO: 132; and CDR3 of SEQ ID NO: 133. In another example, the HER3 antibody is MOR10703, the sequence of which is shown in Table 1 below.

In another aspect, the present invention provides a commercial package comprising as therapeutic agents of (a) a phosphatidylinositol 3-kinase inhibitor selected from the group consisting of a compound of formula (I) or pharmaceutically acceptable salt thereof, and (b) a Her3 antagonist such as antibody or fragment thereof, together with instructions for the simultaneous, separate or sequential administration thereof in the treatment of a breast cancer brain metastases. The HER3 antagonist useful in the invention can be an antibody or fragment thereof that recognizes a conformational epitope of a HER3 receptor comprising amino acid residues 265-277, and 315 within domain 2 and amino acid residues 571, 582-584, 596-597, 600-602, and 609-615 within domain 4 of the HER3 receptor of SEQ ID NO: 1, and wherein the antibody or fragment thereof blocks both ligand-dependent and ligand-independent signal transduction. In one example, the HER3 antagonist comprises a heavy chain variable region CDR1 of SEQ ID NO: 128; CDR2 of SEQ ID NO: 129; CDR3 of SEQ ID NO: 130; and a light chain variable region CDR1 of SEQ ID NO: 131; CDR2 of SEQ ID NO: 132; and CDR3 of SEQ ID NO: 133. In another example, the HER3 antagonist can be MOR10703, the sequence of which is shown in Table 1 below.

DETAILED DESCRIPTION OF THE FIGURES

DETAILED DESCRIPTION

Figure 1:
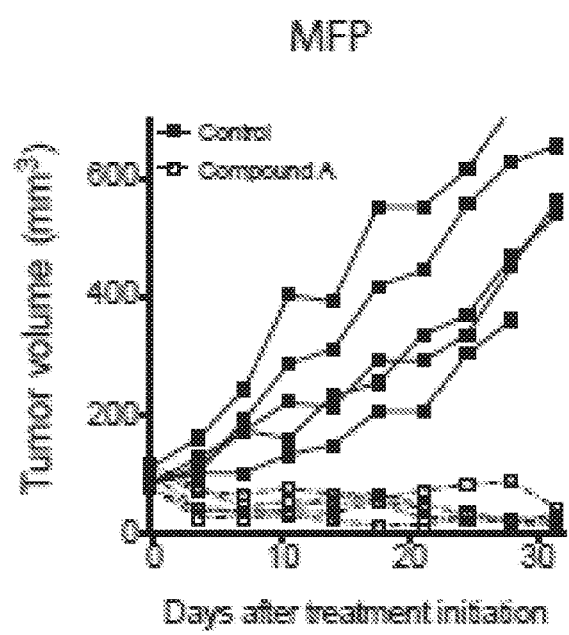
FIG. 1 shows a differential response of BT474-Gluc tumors growing in the MFP (FIG. 1A) and BT474-Gluc tumors growing in the brain (FIG. 1B) despite similar target inhibition and drug penetration.
Figure 1:
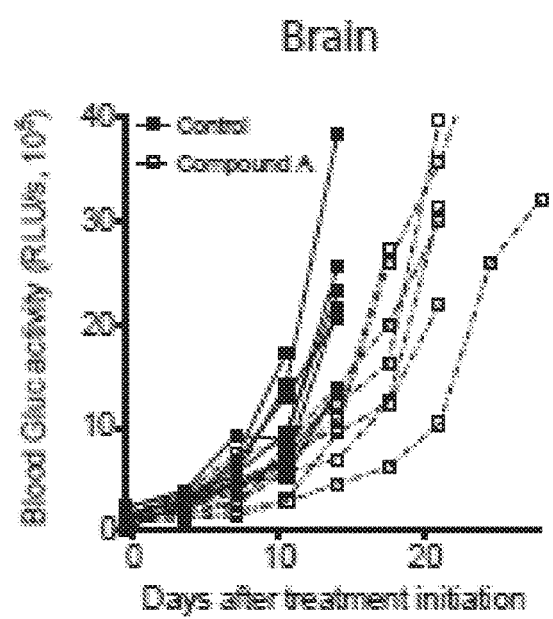

Brain metastases is a devastating progression of breast cancer. Currently treatment options are limited. The present invention is based on the finding that the lack of response to HER2 pathway inhibition in the brain is not due to impaired drug delivery and exposure but that HER3 is hyperactivated by the brain microenvironment and that therapeutic targeting of this pathway overcomes the resistance of HER2-positive breast cancer brain metastases to PI3K inhibition and significantly improves survival.

The present invention pertains to a pharmaceutical combination comprising (a) a phosphatidylinositol 3-kinase, e.g., comprising a compound of formula (I) or a pharmaceutically acceptable salt thereof, and (b) a HER3 antagonist, for simultaneous, separate or sequential administration for use in the treatment of breast cancer brain metastases. In one embodiment, brain metastases from breast cancer can be from a Her2 positive breast cancer. In another embodiment, brain metastases from breast cancer can be from a Her2 positive breast cancer which has also been determined to have one more PIK3CA mutations, e.g., in exon 1, 2, 5, 7, 9 or 20 (e.g., in exon 9 E545K or exon 20 H1047R). The HER3 antagonist can be an antibody or fragment thereof that recognizes a conformational epitope of a HER3 receptor comprising amino acid residues 265-277, and 315 within domain 2 and amino acid residues 571, 582-584, 596-597, 600-602, and 609-615 within domain 4 of the HER3 receptor of SEQ ID NO: 1, and wherein the antibody or fragment thereof blocks both ligand-dependent and ligand-independent signal transduction. Specifically the HER3 antagonist comprises a heavy chain variable region CDR1 of SEQ ID NO: 128; CDR2 of SEQ ID NO: 129; CDR3 of SEQ ID NO: 130; and a light chain variable region CDR1 of SEQ ID NO: 131; CDR2 of SEQ ID NO: 132; and CDR3 of SEQ ID NO: 133. In one example, the HER3 antagonist can be MOR10703, the sequence of which is shown in Table 1 below.

The general terms used herein are defined with the following meanings, unless explicitly stated otherwise:

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The term "combination" or "pharmaceutical combination" is defined herein to refer to either a fixed combination in one dosage unit form, a non-fixed combination or a kit of parts for the combined administration where the phosphatidylinositol 3-kinase inhibitor and the Her3 antagonist may be administered independently at the same time or separately within time intervals that allow that the therapeutic agents show a cooperative, e.g., synergistic, effect.

The term "non-fixed combination" means that the therapeutic agents, e.g. the phosphatidylinositol 3-kinase inhibitor and the Her3 antagonist or pharmaceutically acceptable salt thereof, are both administered to a patient as separate entities or dosage forms either simultaneously, concurrently or sequentially with no specific time limits, wherein such administration provides therapeutically effective levels of the compounds in the body of the subject, e.g., a mammal or human, in need thereof. For example, in one embodiment, PI3k inhibitor is administered daily and the Her3 antagonist is administered weekly.

The term "kit of parts" refers to the therapeutic agents (a) and (b) as defined above that are dosed independently or by use of different fixed combinations with distinguished amounts of the therapeutic agents (a) and (b), i.e., simultaneously or at different time points. The parts of the kit of parts can then e.g., be administered simultaneously or chronologically staggered, that is at different time points and with equal or different time intervals for any part of the kit of parts. The ratio of the total amounts of the therapeutic agent (a) to the therapeutic agent (b) to be administered in the combined preparation can be varied, e.g., in order to cope with the needs of a patient sub-population to be treated or the needs of the single patient.

The term "a phosphatidylinositol 3-kinase inhibitor" or "PI3K inhibitor" is defined herein to refer to a compound which targets, decreases or inhibits phosphatidylinositol 3-kinase. Phosphatidylinositol 3-kinase activity has been shown to increase in response to a number of hormonal and growth factor stimuli, including insulin, platelet-derived growth factor, insulin-like growth factor, epidermal growth factor, colony-stimulating factor, and hepatocyte growth factor, and has been implicated in processes related to cellular growth and transformation.

The term "Her3 antagonist" is defined herein to refer to an inhibitor which targets, decreases, or inhibitor activity of Her3.

The term "HER3" or "HER3 receptor" also known as "ErbB3" as used herein refers to mammalia HER3 protein and refers to mammalia HER3 gene. The preferred HER3 protein is huma HER3 protein present in the cell membrane of a cell. The huma HER3 gene is described in U.S. Pat. No. 5,480,968 and Plowman et al., (1990) Proc. Natl. Acad. Sci. USA, 87:4905-4909. Huma HER3 is well known and defined in Accession No. NP_001973 (human), and represented below as SEQ ID NO: 1.

The term "HER3 ligand" as used herein refers to polypeptides which bind and activate HER3. Examples of HER3 ligands include, but are not limited to neuregulin 1 (NRG) and neuregulin 2, betacellulin, heparin-binding epidermal growth factor, and epiregulin. The term includes biologically active fragments and/or variants of a naturally occurring polypeptide.

The phrase "HER3 activity" or "HER3 activation" as used herein refers to an increase in oligomerization (e.g. an increase in HER3 containing complexes), HER3 phosphorylation, conformational rearrangements (for example those induced by ligands), and HER3 mediated downstream signaling.

The term "ligand-dependent signaling" as used herein refers to the activation of HER (e.g., HER3) via ligand. HER3 activation is evidenced by increased oligomerization (e.g. heterodimerization) and/or HER3 phosphorylation such that downstream signaling pathways (e.g. PI3K) are activated. The antibody or fragment thereof can statistically significantly reduce the amount of phosphorylated HER3 in a stimulated cell exposed to the antigen binding protein (e.g., an antibody) relative to an untreated (control) cell, as measured using the assays described in the Examples. The cell which expresses HER3 can be a naturally occurring cell line (e.g. MCF7) or can be recombinantly produced by introducing nucleic acids encoding HER3 protein into a host cell. Cell stimulation can occur either via the exogenous addition of an activating HER3 ligand or by the endogenous expression of an activating ligand.

The term "ligand-independent signaling" as used herein refers to cellular HER3 activity (e.g phosphorylation) in the absence of a requirement for ligand binding. For example, ligand-independent HER3 activation can be a result of HER2 overexpression or activating mutations in HER3 heterodimer partners such as EGFR and HER2. The antibody or fragment thereof can statistically significantly reduce the amount of phosphorylated HER3 in a cell exposed to the antigen binding protein (e.g., an antibody) relative to an untreated (control) cell. The cell which expresses HER3 can be a naturally occurring cell line (e.g. SK-Br-3) or can be recombinantly produced by introducing nucleic acids encoding HER3 protein into a host cell.

The term "blocks" as used herein refers to stopping or preventing an interaction or a process, e.g., stopping ligand-dependent or ligand-independent signaling.

The term "antibody" as used herein refers to whole antibodies that interact with (e.g., by binding, steric hindrance, stabilizing/destabilizing, spatial distribution) a HER3 epitope and inhibit signal transduction. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. The term "antibody" includes for example, monoclonal antibodies, human antibodies, humanized antibodies, camelised antibodies, chimeric antibodies, single-chain Fvs (scFv), disulfide-linked Fvs (sdFv), Fab fragments, F (ab') fragments, and anti-idiotypic (anti-Id) antibodies (including, e.g., anti-Id antibodies to antibodies of the invention), and epitope-binding fragments of any of the above. The antibodies can be of any isotype (e.g., IgG, IgE, IgM, IgD, IgA and IgY), class (e.g., IgG1, IgG2, IgG3, IgG4, IgA1 and IgA2) or subclass.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminus is a variable region and at the C-terminus is a constant region; the CH3 and CL domains actually comprise the carboxy-terminus of the heavy and light chain, respectively.

The phrase "antibody fragment", as used herein, refers to one or more portions of an antibody that retain the ability to specifically interact with (e.g., by binding, steric hindrance, stabilizing/destabilizing, spatial distribution) a HER3 epitope and inhibit signal transduction. Examples of binding fragments include, but are not limited to, a Fab fragment, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., (1989) Nature 341:544-546), which consists of a VH domain; and an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) Science 242:423-426; and Huston et al., (1988) Proc. Natl. Acad. Sci. 85:5879-5883). Such single chain antibodies are also intended to be encompassed within the term "antibody fragment". These antibody fragments are obtained using conventional techniques known to those of skill in the art, and the fragments are screened for utility in the same manner as are intact antibodies.

The phrase "specifically (or selectively) binds" to an antibody (e.g., a HER3 binding antibody) refers to a binding reaction that is determinative of the presence of a cognate antigen (e.g., a huma HER3) in a heterogeneous population of proteins and other biologics. In addition to the equilibrium constant (KA) noted above, a HER3 binding antibody of the invention typically also has a dissociation rate constant (KD) (koff/kon) of less than $5\times10^{-2}$M, less than $10^{-2}$M, less than $5\times10^{-3}$M, less than $10^{-3}$M, less than $5\times10^{-4}$M, less than $10^{-4}$M, less than $5\times10^{-5}$M, less than $10^{-5}$M, less than $5\times10^{-6}$M, less than $10^{-6}$M, less than $5\times10^{-7}$M, less than $10^{-7}$M, less than $5\times10^{-8}$M, less than $10^{-8}$M, less than $5\times10^{-9}$M, less than $10^{-9}$M, less than $5\times10^{-10}$M, less than $10^{-10}$M, less than $5\times10^{-11}$M, less than $10^{-11}$M, less than $5\times10^{-12}$M, less than $10^{-12}$M, less than $5\times10^{-13}$M, less than $10^{-13}$M, less than $5\times10^{-14}$M, less than $10^{-14}$M, less than $5\times10^{-15}$M, or less than $10^{-15}$M or lower, and binds to HER3 with an affinity that is at least two-fold greater than its affinity for binding to a non-specific antigen (e.g., HSA). In one embodiment, the antibody or fragment thereof has dissociation constant (Kd) of less than 3000 pM, less than 2500 pM, less than 2000 pM, less than 1500 pM, less than 1000 pM, less than 750 pM, less than 500 pM, less than 250 pM, less than 200 pM, less than 150 pM, less than 100 pM, less than 75 pM, less than 10 pM, less than 1 pM as assessed using a method described herein or known to one of skill in the art (e.g., a BIAcore assay, ELISA, FACS, SET) (Biacore International AB, Uppsala, Sweden). The term "Kassoc" or "Ka", as used herein, refers to the association rate of a particular antibody-antigen interaction, whereas the term "Kdis" or "Kd," as used herein, refers to the dissociation rate of a particular antibody-antigen interaction. The term "KD", as used herein, refers to the dissociation constant, which is obtained from the ratio of Kd to Ka (i.e. Kd/Ka) and is expressed as a molar concentration (M). KD values for antibodies can be determined using methods well established in the art. A method for determining the KD of an antibody is by using surface plasmon resonance, or using a biosensor system such as a Biacore® system.

The phrase "antagonist" as used herein refers to an antibody that binds with HER3 and neutralizes the biological activity of HER3 signaling, e.g., reduces, decreases and/or inhibits HER3 induced signaling activity, e.g., in a phospho-HER3 or phospho-Akt assay. Accordingly, an antibody that "inhibits" one or more of these HER3 functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (e.g., or when a control antibody of irrelevant specificity is present). An antibody that inhibits HER3 activity effects such a statistically significant decrease by at least 10% of the measured parameter, by at least 50%, 80% or 90%, and in certain embodiments an antibody of the invention may inhibit greater than 95%, 98% or 99% of HER3 functional activity as evidenced by a reduction in the level of cellular HER3 phosphorylation. Non-limiting examples of HER3 antagonists include antibodies or fragments thereof that bind to a conformational epitope of a HER3 receptor comprising amino acid residues within domain 2 and domain 4 of HER3. This binding of the antibodies or fragments thereof with domain 2 and domain 4 stabilizes the HER3 receptor in an inactive or closed conformation such that HER3 activation is inhibited. Such antibodies block both ligand-dependent (e.g. neuregulin) and ligand-independent HER3 signaling pathways.

The phrase "isolated antibody" refers to an antibody that is substantially free of other antibodies having different antigenic specificities (e.g., an isolated antibody that specifically binds HER3 is substantially free of antibodies that specifically bind antigens other than HER3). An isolated antibody that specifically binds HER3 may, however, have cross-reactivity to other antigens. Moreover, an isolated antibody may be substantially free of other cellular material and/or chemicals.

The term "pharmaceutical composition" is defined herein to refer to a mixture or solution containing at least one therapeutic agent to be administered to a subject, e.g., a mammal or human, in order to treat a particular disease or condition affecting the subject thereof.

The term "pharmaceutically acceptable" is defined herein to refer to those compounds, materials, compositions and/or dosage forms, which are, within the scope of sound medical judgment, suitable for contact with the tissues a subject, e.g., a mammal or human, without excessive toxicity, irritation allergic response and other problem complications commensurate with a reasonable benefit/risk ratio.

The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of a disorder, such as cancer. Within the meaning of the present invention, the term "treat" also denotes to arrest, delay the onset (i.e., the period prior to clinical manifestation of a disease) and/or reduce the risk of developing or worsening a disease.

The term "jointly therapeutically active" or "joint therapeutic effect" as used herein means that the therapeutic agents may be given separately (in a chronologically staggered manner, especially a sequence-specific manner) in such time intervals that they prefer, in the warm-blooded animal, especially a human, to be treated, still show a (preferably synergistic) interaction (joint therapeutic effect). Whether this is the case can, inter alia, be determined by following the blood levels, showing that both therapeutic agents are present in the blood of the human to be treated at least during certain time intervals.

The term "pharmaceutically effective amount" or "clinically effective amount" of a pharmaceutical combination of therapeutic agents is an amount sufficient to provide an observable improvement over the baseline clinically observable signs and symptoms of the breast cancer brain metastases treated with the combination.

The term "synergistic effect" as used herein refers to action of two therapeutic agents such as, for example, (a) a compound of formula (I) or a pharmaceutically acceptable salt thereof, and a Her3 antagonist producing an effect, for example, slowing the symptomatic progression of a breast cancer brain metastases or symptoms thereof, which is greater than the simple addition of the effects of each therapeutic agent administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

The term "subject" or "patient" as used herein includes animals, which are capable of suffering from or afflicted with a breast cancer brain metastases. Examples of subjects include mammals, e.g., humans, dogs, cows, horses, pigs, sheep, goats, cats, mice, rabbits, rats and transgenic non-human animals. In the preferred embodiment, the subject is a human, e.g., a human suffering from, at risk of suffering from, or potentially capable of suffering from a breast cancer brain metastases.

The term about" or "approximately" shall have the meaning of within 10%, more preferably within 5%, of a given value or range.

HER3 Antagonists

Any HER3 antagonist can be used. In one embodiment, the invention includes an antibody or fragment thereof is as described in WO2012022814, which publication is hereby incorporated into the present application by reference in its entirety. In one example, the HER3 antagonist useful for treatment in the presently disclosed method includes an antibody or fragment thereof which recognizes a specific conformational state of HER3 such that the antibody or fragment thereof prevents HER3 from interacting with a co-receptor (including, but not limited to, HER1, HER2 and HER4). In some embodiments, the antibody or fragment thereof prevents HER3 from interacting with a co-receptor by stabilizing the HER3 receptor in an inactive or closed state. In one embodiment, the antibody or fragment thereof stabilizes the HER3 receptor by binding to amino acid residues within domain 2 and domain 4 of HER3. In this inactive state, the dimerization loop located within domain 2 is not exposed and therefore unavailable for dimerization with other co-receptors (including, but not limited to, HER1, HER2 and HER4). In one example, the antibody recognizes a conformational epitope of a HER3 receptor, wherein the conformational epitope comprises amino acid residues within domain 2 and domain 4 of the HER3 receptor, and wherein the antibody or fragment thereof blocks both ligand-dependent and ligand-independent signal transduction. The conformational epitope comprises amino acid residues 265-277, 315 (of domain 2), 571, 582-584, 596-597, 600-602, 609-615 (of domain 4), or a subset thereof. In one example, the VH of the antibody or fragment thereof binds to at least one of the following HER3 residues: Asn266, Lys267, Leu268, Thr269, Gln271, Glu273, Pro274, Asn275, Pro276, His277, Asn315, Asp571, Pro583, His584, Ala596, Lys597. In another example, the VL of the antibody or fragment thereof binds to at least one of the following HER3 residues: Tyr265, Lys267, Leu268, Phe270, Gly582, Pro583, Lys597, Ile600, Lys602, Glu609, Arg611, Pro612, Cys613, His614, Glu615. The isolated antibody or fragment thereof can be a monoclonal antibody, a polyclonal antibody, a chimeric antibody, a humanized antibody, and a synthetic antibody.

In another example, the isolated antibody or fragment thereof can recognize a conformational epitope of a HER3 receptor, wherein the conformational epitope comprises amino acid residues within domain 2 and domain 4 of the HER3 receptor, and wherein the antibody or fragment thereof inhibits phosphorylation of HER3 as assessed by HER3 ligand-dependent phosphorylation assay (e.g., an assay uses stimulated MCF7 cells in the presence of neuregulin (NRG)). In this example, the antibody or fragment thereof to a HER3 receptor can have a dissociation (KO) of at least $1\times10^7$ M-1, $10^8$ M-1, $10^9$ M-1, $10^{10}$ M-1, $10^{11}$ M-1, $10^{12}$ M-1, or $10^{13}$ M-1.

In another example, the isolated antibody or fragment thereof can bind to the same conformational epitope as an antibody described in Table 1.

In some embodiments, the antibody or fragment thereof binds to human HER3 protein having a conformational epitope comprising (i) HER3 amino acid residues 265-277 and 315 (of domain 2) and (ii) HER3 amino acid residues 571, 582-584, 596-597, 600-602, 609-615 (of domain 4) of SEQ ID NO: 1, or a subset thereof. In some embodiments, the antibody or fragment thereof binds to amino acids within or overlapping amino acid residues 265-277 and 315 (of domain 2) and (ii) HER3 amino acid residues 571, 582-584, 596-597, 600-602, 609-615 (of domain 4) of SEQ ID NO: 1. In some embodiments, the antibody or fragment thereof binds to amino acids within (and/or amino acid sequences consisting of) amino acids 265-277 and 315 (of domain 2) and (ii) HER3 amino acid residues 571, 582-584, 596-597, 600-602, 609-615 (of domain 4) of SEQ ID NO: 1, or a subset thereof. In some embodiments, the antibody or fragment thereof binds to the conformational epitope such that it restricts the mobility of domain 2 and domain 4, stabilizing it in an inactive or closed conformation. The failure to form the active conformation results in failure to activate signal transduction. In some embodiments, the antibody or fragment thereof binds to the conformational epitope such that it occludes the dimerization loop within domain 2, thereby rendering it unavailable for receptor-receptor interaction. The failure to form homo- or heterodimers results in failure to activate signal transduction. The present invention can utilize HER3 antibodies that recognize a conformational epitope of HER3 such that they block both ligand-dependent and ligand-independent HER3 signal transduction pathways. Such a class of antibodies are disclosed in Table 1.

The present invention provides antibodies that specifically bind a HER3 protein (e.g., human and/or cynomologus HER3), said antibodies comprising a VH domain having an amino acid sequence of SEQ ID NO: 15, 33, 51, 69, 87, 105, 123, 141, 159, 177, 195, 213, 231, 249, 267, 285, 303, 321, 339, 357, and 375. The present invention provides antibodies that specifically bind a HER3 protein (e.g., human and/or cynomologus HER3), said antibodies comprising a VL domain having an amino acid sequence of SEQ ID NO: 14, 32, 50, 68, 86, 104, 122, 140, 158, 176, 194, 212, 230, 248, 266, 284, 302, 320, 338, 356, and 374. The present invention also provides antibodies that specifically bind to a HER3 protein (e.g., human and/or cynomologus HER3), said antibodies comprising a VH CDR having an amino acid sequence of any one of the VH CDRs listed in Table 1, infra. In particular, the invention provides antibodies that specifically bind to a HER3 protein (e.g., human and/or cynomologus HER3), said antibodies comprising (or alternatively, consisting of) one, two, three, four, five or more VH CDRs having an amino acid sequence of any of the VH CDRs listed in Table 1, infra.

Other antibodies of the invention include amino acids that have been mutated, yet have at least 60, 70, 80, 90, 95, or 98 percent identity in the CDR regions with the CDR regions depicted in the sequences described in Table 1. In some embodiments, it includes mutant amino acid sequences wherein no more than 1, 2, 3, 4 or 5 amino acids have been mutated in the CDR regions when compared with the CDR regions depicted in the sequence described Table 1, while still maintaining their specificity for the original antibody's epitope Other antibodies of the invention include amino acids that have been mutated, yet have at least 60, 70, 80, 90, 95, or 98 percent identity in the framework regions with the framework regions depicted in the sequences described in Table 1. In some embodiments, it includes mutant amino acid sequences wherein no more than 1, 2, 3, 4, 5, 6, or 7 amino acids have been mutated in the framework regions when compared with the framework regions depicted in the sequence described Table 1, while still maintaining their specificity for the original antibody's epitope. The present invention also provides nucleic acid sequences that encode VH, VL, the full length heavy chain, and the full length light chain of the antibodies that specifically bind to a HER3 protein (e.g., human and/or cynomologus HER3).

The HER3 antibodies of the invention useful in the methods of the invention can bind to the conformational epitope of HER3 comprising amino acid residues from domain 2 and domain 4 of HER3.

TABLE 1

Examples of HER3 Antibodies useful in the methods of the Present Invention

| SEQ ID NUMBER | Ab region | |
|---|---|---|
| MOR09823 | | |
| SEQ ID NO: 2 (Kabat) | HCDR1 | SYAMS |
| SEQ ID NO: 3 (Kabat) | HCDR2 | VTGAVGRTYYPDSVKG |

TABLE 1-continued

Examples of HER3 Antibodies useful in the methods of the Present Invention

| SEQ ID NUMBER | Ab region | |
|---|---|---|
| SEQ ID NO: 4 (Kabat) | HCDR3 | WGDEGFDI |
| SEQ ID NO: 5 (Kabat) | LCDR1 | RASQGISNWLA |
| SEQ ID NO: 6 (Kabat) | LCDR2 | GASSLQS |
| SEQ ID NO: 7 (Kabat) | LCDR3 | QQYSSFPTT |
| SEQ ID NO: 8 (Chothia) | HCDR1 | GFTFSSY |
| SEQ ID NO: 9 (Chothia) | HCDR2 | GAVGR |
| SEQ ID NO: 10 (Chothia) | HCDR3 | WGDEGFDI |
| SEQ ID NO: 11 (Chothia) | LCDR1 | SQGISNW |
| SEQ ID NO: 12 (Chothia) | LCDR2 | GAS |
| SEQ ID NO: (Chothia) 13 | LCDR3 | YSSFPT |
| SEQ ID NO: 14 | VL | DIQMTQSPSSLSASVGDRVTITCRASQGISNWLAWYQQKPGKAPKLLIYGASSLQSGVPSRFSGSGSGTDFTLTISSLQPEDFAVYYCQQYSSFPTTFGQGTKVEIK |
| SEQ ID NO: 15 | VH | QVQLVESGGGLVQPGGSLRLSCAASGFTFSSYAMSWVRQAPGKGLEWVSVTGAVGRTYYPDSVKGRFTISRDNSKNTLYLQMNSLRAEDTAVYYCARWGDEGFDIWGQGTLVTVSS |
| SEQ ID NO: 16 | DNA VL | GATATCCAGATGACCCAGAGCCCGTCTAGCCTGAGCGCGAGCGTGGGTGATCGTGTGACCATTACCTGCAGAGCGAGCCAGGGTATTTCTAATTGGCTGGCTTGGTACCAGCAGAAACCAGGTAAAGCACCGAAACTATTAATTTATGGTGCTTCTTCTTTGCAAAGCGGGGTCCCGTCCCGTTTTAGCGGCTCTGGATCCGGCACTGATTTTACCCTGACCATTAGCAGCCTGCAACCTGAAGACTTTGCGGTTTATTATTGCCAGCAGTATTCTTCTTTTCCTACTACCTTTGGCCAGGGTACGAAAGTTGAAATTAAA |
| SEQ ID NO: 17 | DNA VH | CAGGTGCAATTGGTGGAAAGCGGCGGCGCCTGGTGCAACCGGGCGGCAGCCTGCGTCTGAGCTGCGCGGCCTCCGGATTTACCTTTAGCAGCTATGCGATGAGCTGGGTGCGCCAAGCCCCTGGGAAGGGTCTCGAGTGGGTGAGCGTTACTGGTGCTGTTGGTCGTACTTATTATCCTGATTCTGTTAAGGGTCGTTTTACCATTTCACGTGATAATTCGAAAAACACCCTGTATCTGCAAATGAACAGCCTGCGTGCGGAAGATACGGCCGTGTATTATTGCGCGCGTTGGGGTGATGAGGGTTTTGATATTTGGGGCCAAGGCACCCTGGTGACGGTTAGCTCA |
| SEQ ID NO: 18 | Light Kappa | DIQMTQSPSSLSASVGDRVTITCRASQGISNWLAWYQQKPGKAPKLLIYGASSLQSGVPSRFSGSGSGTDFTLTISSLQPEDFAVYYCQQYSSFPTTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| SEQ ID NO: 19 | Heavy IgG1 | QVQLVESGGGLVQPGGSLRLSCAASGFTFSSYAMSWVRQAPGKGLEWVSVTGAVGRTYYPDSVKGRFTISRDNSKNTLYLQMNSLRAEDTAVYYCARWGDEGFDIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| MOR09824 | | |
| SEQ ID NO: 20 (Kabat) | HCDR1 | SYAMS |
| SEQ ID NO: 21 (Kabat) | HCDR2 | VISAWGHVKYYADSVKG |
| SEQ ID NO: 22 (Kabat) | HCDR3 | WGDEGFDI |

TABLE 1-continued

Examples of HER3 Antibodies useful in the methods of the Present Invention

| SEQ ID NUMBER | Ab region | |
|---|---|---|
| SEQ ID NO: 23 (Kabat) | LCDR1 | RASQGISNWLA |
| SEQ ID NO: 24 (Kabat) | LCDR2 | GASSLQS |
| SEQ ID NO: 25 (Kabat) | LCDR3 | QQYSSFPTT |
| SEQ ID NO: 26 (Chothia) | HCDR1 | GFTFSSY |
| SEQ ID NO: 27 (Chothia) | HCDR2 | SAWGHV |
| SEQ ID NO: 28 (Chothia) | HCDR3 | WGDEGFDI |
| SEQ ID NO: 29 (Chothia) | LCDR1 | SQGISNW |
| SEQ ID NO: 30 (Chothia) | LCDR2 | GAS |
| SEQ ID NO: 31 (Chothia) | LCDR3 | YSSFPT |
| SEQ ID NO: 32 | VL | DIQMTQSPSSLSASVGDRVTITCRASQGISNWLAWYQ QKPGKAPKLLIYGASSLQSGVPSRFSGSGSGTDFTLT ISSLQPEDFAVYYCQQYSSFPTTFGQGTKVEIK |
| SEQ ID NO: 33 | VH | QVQLVESGGGLVQPGGSLRLSCAASGFTFSSYAMSWV RQAPGKGLEWVSVISAWGHVKYYADSVKGRFTISRDN SKNTLYLQMNSLRAEDTAVYYCARWGDEGFDIWGQGT LVTVSS |
| SEQ ID NO: 34 | DNA VL | GATATCCAGATGACCCAGAGCCCGTCTAGCCTGAGCG CGAGCGTGGGTGATCGTGTGACCATTACCTGCAGAGC GAGCCAGGGTATTTCTAATTGGCTGGCTTGGTACCAG CAGAAACCAGGTAAAGCACCGAAACTATTAATTTATG GTGCTTCTTCTTTGCAAAGCGGGGTCCCGTCCCGTTT TAGCGGCTCTGGATCCGGCACTGATTTTACCCTGACC ATTAGCAGCCTGCAACCTGAAGACTTTGCGGTTTATT ATTGCCAGCAGTATTCTTCTTTTCCTACTACCTTTGG CCAGGGTACGAAAGTTGAAATTAAA |
| SEQ ID NO: 35 | DNA VH | CAGGTGCAATTGGTGGAAAGCGGCGGCGGCCTGGTGC AACCGGGCGGCAGCCTGCGTCTGAGCTGCGCGGCCTC CGGATTTACCTTTAGCAGCTATGCGATGAGCTGGGTG CGCCAAGCCCCTGGGAAGGGTCTCGAGTGGGTGAGCG TTATTTCTGCTTGGGGTCATGTTAAGTATTATGCTGA TTCTGTTAAGGGTCGTTTTACCATTTCACGTGATAAT TCGAAAAACACCCTGTATCTGCAAATGAACAGCCTGC GTGCGGAAGATACGGCCGTGTATTATTGCGCGCGTTG GGGTGATGAGGGTTTTGATATTTGGGGCCAAGGCACC CTGGTGACGGTTAGCTCA |
| SEQ ID NO: 36 | Light Kappa | DIQMTQSPSSLSASVGDRVTITCRASQGISNWLAWYQ QKPGKAPKLLIYGASSLQSGVPSRFSGSGSGTDFTLT ISSLQPEDFAVYYCQQYSSFPTTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 37 | Heavy IgG1 | QVQLVESGGGLVQPGGSLRLSCAASGFTFSSYAMSWV RQAPGKGLEWVSVISAWGHVKYYADSVKGRFTISRDN SKNTLYLQMNSLRAEDTAVYYCARWGDEGFDIWGQGT LVTVSSASTKGPSVFPLAPSSKSTSGGTAALGCLVKD YFPEPVTVSWNSGALTSGVHTFPAVLQSSGLYSLSSV VTVPSSSLGTQTYICNVNHKPSNTKVDKRVEPKSCDK THTCPPCPAPELLGGPSVFLFPPKPKDTLMISRTPEV TCVVVDVSHEDPEVKFNWYVDGVEVHNAKTKPREEQY NSTYRVVSVLTVLHQDWLNGKEYKCKVSNKALPAPIE KTISKAKGQPREPQVYTLPPSREEMTKNQVSLTCLVK GFYPSDIAVEWESNGQPENNYKTTPPVLDSDGSFFLY SKLTVDKSRWQQGNVFSCSVMHEALHNHYTQKSLSLS PGK |
| MOR09825 | | |
| SEQ ID NO: 38 (Kabat) | HCDR1 | SYAMS |
| SEQ ID NO: 39 (Kabat) | HCDR2 | AINSQGKSTYYADSVKG |
| SEQ ID NO: 40 (Kabat) | HCDR3 | WGDEGFDI |
| SEQ ID NO: 41 (Kabat) | LCDR1 | RASQGISNWLA |

TABLE 1-continued

Examples of HER3 Antibodies useful in the methods of the Present Invention

| SEQ ID NUMBER | Ab region | |
|---|---|---|
| SEQ ID NO: 42 (Kabat) | LCDR2 | GASSLQS |
| SEQ ID NO: 43 (Kabat) | LCDR3 | QQYSSFPTT |
| SEQ ID NO: 44 (Chothia) | HCDR1 | GFTFSSY |
| SEQ ID NO: 45 (Chothia) | HCDR2 | NSQGKS |
| SEQ ID NO: 46 (Chothia) | HCDR3 | WGDEGFDI |
| SEQ ID NO: 47 (Chothia) | LCDR1 | SQGISNW |
| SEQ ID NO: 48 (Chothia) | LCDR2 | GAS |
| SEQ ID NO: 49 (Chothia) | LCDR3 | YSSFPT |
| SEQ ID NO: 50 | VL | DIQMTQSPSSLSASVGDRVTITCRASQGISNWLAWYQQKPGKAPKLLIYGASSLQSGVPSRFSGSGSGTDFTLTISSLQPEDFAVYYCQQYSSFPTTFGQGTKVEIK |
| SEQ ID NO: 51 | VH | QVQLVESGGGLVQPGGSLRLSCAASGFTFSSYAMSWVRQAPGKGLEWVSAINSQGKSTYYADSVKGRFTISRDNSKNTLYLQMNSLRAEDTAVYYCARWGDEGFDIWGQGTLVTVSS |
| SEQ ID NO: 52 | DNA VL | GATATCCAGATGACCCAGAGCCCGTCTAGCCTGAGCGCGAGCGTGGGTGATCGTGTGACCATTACCTGCAGAGCGAGCCAGGGTATTTCTAATTGGCTGGCTTGGTACCAGCAGAAACCAGGTAAAGCACCGAAACTATTAATTTATGGTGCTTCTTCTTTGCAAAGCGGGGTCCCGTCCCGTTTTAGCGGCTCTGGATCCGGCACTGATTTTACCCTGACCATTAGCAGCCTGCAACCTGAAGACTTTGCGGTTTATTATTGCCAGCAGTATTCTTCTTTTCCTACTACCTTTGGCCAGGGTACGAAAGTTGAAATTAAA |
| SEQ ID NO: 53 | DNA VH | CAGGTGCAATTGGTGGAAAGCGGCGGCGCCTGGTGCAACCGGGCGGCAGCCTGCGTCTGAGCTGCGCGGCCTCCGGATTTACCTTTAGCAGCTATGCGATGAGCTGGGTGCGCCAAGCCCCTGGGAAGGGTCTCGAGTGGGTGAGCGCTATTAATTCTCAGGGTAAGTCTACTTATTATGCTGATTCTGTTAAGGGTCGTTTTACCATTTCACGTGATAATTCGAAAAACACCCTGTATCTGCAAATGAACAGCCTGCGTGCGGAAGATACGGCCGTGTATTATTGCGCGCGTTGGGGTGATGAGGGTTTTGATATTTGGGGCCAAGGCACCCTGGTGACGGTTAGCTCA |
| SEQ ID NO: 54 | Light Kappa | DIQMTQSPSSLSASVGDRVTITCRASQGISNWLAWYQQKPGKAPKLLIYGASSLQSGVPSRFSGSGSGTDFTLTISSLQPEDFAVYYCQQYSSFPTTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| SEQ ID NO: 55 | Heavy IgG1 | QVQLVESGGGLVQPGGSLRLSCAASGFTFSSYAMSWVRQAPGKGLEWVSAINSQGKSTYYADSVKGRFTISRDNSKNTLYLQMNSLRAEDTAVYYCARWGDEGFDIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| MOR09974 | | |
| SEQ ID NO: 56 (Kabat) | HCDR1 | SYAMS |
| SEQ ID NO: 57 (Kabat) | HCDR2 | VINPSGNFTNYADSVKG |
| SEQ ID NO: 58 (Kabat) | HCDR3 | WGDEGFDI |
| SEQ ID NO: 59 (Kabat) | LCDR1 | RASQGISNWLA |
| SEQ ID NO: 60 (Kabat) | LCDR2 | GASSLQS |

TABLE 1-continued

Examples of HER3 Antibodies useful in the methods of the Present Invention

| SEQ ID NUMBER | Ab region | |
|---|---|---|
| SEQ ID NO: 61 (Kabat) | LCDR3 | QQYSSFPTT |
| SEQ ID NO: 62 (Chothia) | HCDR1 | GFTFSSY |
| SEQ ID NO: 63 (Chothia) | HCDR2 | NPSGNF |
| SEQ ID NO: 64 (Chothia) | HCDR3 | WGDEGFDI |
| SEQ ID NO: 65 (Chothia) | LCDR1 | SQGISNW |
| SEQ ID NO: 66 (Chothia) | LCDR2 | GAS |
| SEQ ID NO: 67 (Chothia) | LCDR3 | YSSFPT |
| SEQ ID NO: 68 | VL | DIQMTQSPSSLSASVGDRVTITCRASQGISNWLAWYQ QKPGKAPKLLIYGASSLQSGVPSRFSGSGSGTDFTLT ISSLQPEDFAVYYCQQYSSFPTTFGQGTKVEIK |
| SEQ ID NO: 69 | VH | QVQLVESGGGLVQPGGSLRLSCAASGFTFSSYAMSWV RQAPGKGLEWVSVINPSGNFTNYADSVKGRFTISRDN SKNTLYLQMNSLRAEDTAVYYCARWGDEGFDIWGQGT LVTVSS |
| SEQ ID NO: 70 | DNA VL | GATATCCAGATGACCCAGAGCCCGTCTAGCCTGAGCG CGAGCGTGGGTGATCGTGTGACCATTACCTGCAGAGC GAGCCAGGGTATTTCTAATTGGCTGGCTTGGTACCAG CAGAAACCAGGTAAAGCACCGAAACTATTAATTTATG GTGCTTCTTCTTTGCAAAGCGGGGTCCCGTCCCGTTT TAGCGGCTCTGGATCCGGCACTGATTTTACCCTGACC ATTAGCAGCCTGCAACCTGAAGACTTTGCGGTTTATT ATTGCCAGCAGTATTCTTCTTTTCCTACTACCTTTGG CCAGGGTACGAAAGTTGAAATTAAA |
| SEQ ID NO: 71 | DNA VH | CAGGTGCAATTGGTGGAAAGCGGCGGCGGCCTGGTGC AACCGGGCGGCAGCCTGCGTCTGAGCTGCGCGGCCTC CGGATTTACCTTTAGCAGCTATGCGATGAGCTGGGTG CGCCAAGCCCCTGGGAAGGGTCTCGAGTGGGTGAGCG TTATTAATCCTTCTGGTAATTTTACTAATTATGCTGA TTCTGTTAAGGGTCGTTTTACCATTTCACGTGATAAT TCGAAAAACACCCTGTATCTGCAAATGAACAGCCTGC GTGCGGAAGATACGGCCGTGTATTATTGCGCGCGTTG GGGTGATGAGGGTTTTGATATTTGGGGCCAAGGCACC CTGGTGACGGTTAGCTCA |
| SEQ ID NO: 72 | Light Kappa | DIQMTQSPSSLSASVGDRVTITCRASQGISNWLAWYQ QKPGKAPKLLIYGASSLQSGVPSRFSGSGSGTDFTLT ISSLQPEDFAVYYCQQYSSFPTTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 73 | Heavy IgG1 | QVQLVESGGGLVQPGGSLRLSCAASGFTFSSYAMSWV RQAPGKGLEWVSVINPSGNFTNYADSVKGRFTISRDN SKNTLYLQMNSLRAEDTAVYYCARWGDEGFDIWGQGT LVTVSSASTKGPSVFPLAPSSKSTSGGTAALGCLVKD YFPEPVTVSWNSGALTSGVHTFPAVLQSSGLYSLSSV VTVPRVPSSSLGTQTYICNVNHKPSNTKVDKRVEPKSC DKTHTCPPCPAPELLGGPSVFLFPPKPKDTLMISRTP EVTCVVVDVSHEDPEVKFNWYVDGVEVHNAKTKPREE QYNSTYRVVSVLTVLHQDWLNGKEYKCKVSNKALPAP IEKTISKAKGQPREPQVYTLPPSREEMTKNQVSLTCL VKGFYPSDIAVEWESNGQPENNYKTTPPVLDSDGSFF LYSKLTVDKSRWQQGNVFSCSVMHEALHNHYTQKSLS LSPGK |

MOR10452

| SEQ ID NO: 74 (Kabat) | HCDR1 | SYAMS |
| SEQ ID NO: 75 (Kabat) | HCDR2 | NTSPIGYTYYAGSVKG |
| SEQ ID NO: 76 (Kabat) | HCDR3 | WGDEGFDI |
| SEQ ID NO: 77 (Kabat) | LCDR1 | RASQGISNWLA |
| SEQ ID NO: 78 (Kabat) | LCDR2 | GASSLQS |
| SEQ ID NO: 79 (Kabat) | LCDR3 | QQYSSFPTT |

TABLE 1-continued

Examples of HER3 Antibodies useful in the methods of the Present Invention

| SEQ ID NUMBER | Ab region | |
|---|---|---|
| SEQ ID NO: 80 (Chothia) | HCDR1 | GFTFSSY |
| SEQ ID NO: 81 (Chothia) | HCDR2 | SPIGY |
| SEQ ID NO: 82 (Chothia) | HCDR3 | WGDEGFDI |
| SEQ ID NO: 83 (Chothia) | LCDR1 | SQGISNW |
| SEQ ID NO: 84 (Chothia) | LCDR2 | GAS |
| SEQ ID NO: 85 (Chothia) | LCDR3 | YSSFPT |
| SEQ ID NO: 86 | VL | DIQMTQSPSSLSASVGDRVTITCRASQGISNWLAWYQ QKPGKAPKLLIYGASSLQSGVPSRFSGSGSGTDFTLT ISSLQPEDFAVYYCQQYSSFPTTFGQGTKVEIK |
| SEQ ID NO: 87 | VH | QVQLVESGGGLVQPGGSLRLSCAASGFTFSSYAMSWV RQAPGKGLEWVSNTSPIGYTYYAGSVKGRFTISRDNS KNTLYLQMNSLRAEDTAVYYCARWGDEGFDIWGQGTL VTVSS |
| SEQ ID NO: 88 | DNA VL | GATATCCAGATGACCCAGAGCCCGTCTAGCCTGAGCG CGAGCGTGGGTGATCGTGTGACCATTACCTGCAGAGC GAGCCAGGGTATTTCTAATTGGCTGGCTTGGTACCAG CAGAAACCAGGTAAAGCACCGAAACTATTAATTTATG GTGCTTCTTCTTTGCAAAGCGGGGTCCCGTCCCGTTT TAGCGGCTCTGGATCCGGCACTGATTTTACCCTGACC ATTAGCAGCCTGCAACCTGAAGACTTTGCGGTTTATT ATTGCCAGCAGTATTCTTCTTTTCCTACTACCTTTGG CCAGGGTACGAAAGTTGAAATTAAA |
| SEQ ID NO: 89 | DNA VH | CAGGTGCAATTGGTGGAAAGCGGCGGCGCCTGGTGC AACCGGGCGGCAGCCTGCGTCTGAGCTGCGCGGCCTC CGGATTTACCTTTAGCAGCTATGCGATGAGCTGGGTG CGCCAAGCCCCTGGGAAGGGTCTCGAGTGGGTGAGCA ATACTTCTCCTATTGGTTATACTTATTATGCTGGTTC TGTTAAGGGTCGTTTTACCATTTCACGTGATAATTCG AAAAACACCCTGTATCTGCAAATGAACAGCCTGCGTG CGGAAGATACGGCCGTGTATTATTGCGCGCGTTGGGG TGATGAGGGTTTTGATATTTGGGGCCAAGGCACCCTG GTGACGGTTAGCTCA |
| SEQ ID NO: 90 | Light Kappa | DIQMTQSPSSLSASVGDRVTITCRASQGISNWLAWYQ QKPGKAPKLLIYGASSLQSGVPSRFSGSGSGTDFTLT ISSLQPEDFAVYYCQQYSSFPTTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEA |
| SEQ ID NO: 91 | Heavy Chain (only VH and CH1 domains) | QVQLVESGGGLVQPGGSLRLSCAASGFTFSSYAMSWV RQAPGKGLEWVSNTSPIGYTYYAGSVKGRFTISRDNS KNTLYLQMNSLRAEDTAVYYCARWGDEGFDIWGQGTL VTVSSASTKGPSVFPLAPSSKSTSGGTAALGCLVKDY FPEPVTVSWNSGALTSGVHTFPAVLQSSGLYSLSSVV TVPSSSLGTQTYICNVNHKPSNTKVDKKVEPKS |
| MOR10701 | | |
| SEQ ID NO: 92 (Kabat) | HCDR1 | SYAMS |
| SEQ ID NO: 93 (Kabat) | HCDR2 | VTGAVGRSTYYPDSVKG |
| SEQ ID NO: 94 (Kabat) | HCDR3 | WGDEGFDI |
| SEQ ID NO: 95 (Kabat) | LCDR1 | RASQGISNWLA |
| SEQ ID NO: 96 (Kabat) | LCDR2 | GASSLQS |
| SEQ ID NO: 97 (Kabat) | LCDR3 | QQYSSFPTT |
| SEQ ID NO: 98 (Chothia) | HCDR1 | GFTFSSY |
| SEQ ID NO: 99 (Chothia) | HCDR2 | GAVGRS |
| SEQ ID NO: 100 (Chothia) | HCDR3 | WGDEGFDI |
| SEQ ID NO: 101 (Chothia) | LCDR1 | SQGISNW |
| SEQ ID NO: 102 (Chothia) | LCDR2 | GAS |

TABLE 1-continued

Examples of HER3 Antibodies useful in the methods of the Present Invention

| SEQ ID NUMBER | Ab region | |
|---|---|---|
| SEQ ID NO: 103 (Chothia) | LCDR3 | YSSFPT |
| SEQ ID NO: 104 | VL | DIQMTQSPSSLSASVGDRVTITCRASQGISNWLAWYQ QKPGKAPKLLIYGASSLQSGVPSRFSGSGSGTDFTLT ISSLQPEDFATYYCQQYSSFPTTFGQGTKVEIK |
| SEQ ID NO: 105 | VH | EVQLLESGGGLVQPGGSLRLSCAASGFTFSSYAMSWV RQAPGKGLEWVSVTGAVGRSTYYPDSVKGRFTISRDN SKNTLYLQMNSLRAEDTAVYYCARWGDEGFDIWGQGT LVTVSS |
| SEQ ID NO: 106 | DNA VL | GATATCCAGATGACCCAGAGCCCCAGCAGCCTGAGCG CCAGCGTGGGCGACAGAGTGACCATCACCTGTCGGGC CAGCCAGGGCATCAGCAACTGGCTGGCCTGGTATCAG CAGAAGCCCGGCAAGGCCCCCAAGCTGCTGATCTACG GCGCCAGCTCCCTGCAGAGCGGCGTGCCAAGCAGATT CAGCGGCAGCGGCTCCGGCACCGACTTCACCCTGACC ATCAGCAGCCTGCAGCCCGAGGACTTCGCCACCTACT ACTGCCAGCAGTACAGCAGCTTCCCCACCACCTTCGG CCAGGGCACCAAGGTGGAAATCAAG |
| SEQ ID NO: 107 | DNA VH | GAGGTGCAATTGCTGGAAAGCGGCGGAGGCCTGGTGC AGCCTGGCGGCAGCCTGAGACTGTCTTGCGCCGCCAG CGGCTTCACCTTCAGCAGCTACGCCATGAGCTGGGTC CGCCAGGCCCCTGGCAAGGGACTGGAATGGGTGTCCG TGACAGGCGCCGTGGGCAGAAGCACCTACTACCCCGA CAGCGTGAAGGGCCGGTTCACCATCAGCCGGGACAAC AGCAAGAACACCCTGTACCTGCAGATGAACAGCCTGC GGGCCGAGGACACCGCCGTGTACTACTGTGCCAGATG GGGCGACGAGGGCTTCGACATCTGGGGCCAGGGCACC CTGGTCACCGTCAGCTCA |
| SEQ ID NO: 108 | Light Kappa | DIQMTQSPSSLSASVGDRVTITCRASQGISNWLAWYQ QKPGKAPKLLIYGASSLQSGVPSRFSGSGSGTDFTLT ISSLQPEDFATYYCQQYSSFPTTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 109 | Heavy IgG1 | EVQLLESGGGLVQPGGSLRLSCAASGFTFSSYAMSWV RQAPGKGLEWVSVTGAVGRSTYYPDSVKGRFTISRDN SKNTLYLQMNSLRAEDTAVYYCARWGDEGFDIWGQGT LVTVSSASTKGPSVFPLAPSSKSTSGGTAALGCLVKD YFPEPVTVSWNSGALTSGVHTFPAVLQSSGLYSLSSV VTVPSSSLGTQTYICNVNHKPSNTKVDKRVEPKSCDK THTCPPCPAPELLGGPSVFLFPPKPKDTLMISRTPEV TCVVVDVSHEDPEVKFNWYVDGVEVHNAKTKPREEQY NSTYRVVSVLTVLHQDWLNGKEYKCKVSNKALPAPIE KTISKAKGQPREPQVYTLPPSREEMTKNQVSLTCLVK GFYPSDIAVEWESNGQPENNYKTTPPVLDSDGSFFLY SKLTVDKSRWQQGNVFSCSVMHEALHNHYTQKSLSLS PGK |
| MOR10702 | | |
| SEQ ID NO: 110 (Kabat) | HCDR1 | SYAMS |
| SEQ ID NO: 111 (Kabat) | HCDR2 | VISAWGHVKYYADSVKG |
| SEQ ID NO: 112 (Kabat) | HCDR3 | WGDEGFDI |
| SEQ ID NO: 113 (Kabat) | LCDR1 | RASQGISNWLA |
| SEQ ID NO: 114 (Kabat) | LCDR2 | GASSLQS |
| SEQ ID NO: 115 (Kabat) | LCDR3 | QQYSSFPTT |
| SEQ ID NO: 116 (Chothia) | HCDR1 | GFTFSSY |
| SEQ ID NO: 117 (Chothia) | HCDR2 | SAWGHV |
| SEQ ID NO: 118 (Chothia) | HCDR3 | WGDEGFDI |
| SEQ ID NO: 119 (Chothia) | LCDR1 | SQGISNW |
| SEQ ID NO: 120 (Chothia) | LCDR2 | GAS |
| SEQ ID NO: 121 (Chothia) | LCDR3 | YSSFPT |

TABLE 1-continued

Examples of HER3 Antibodies useful in the methods of the Present Invention

| SEQ ID NUMBER | Ab region | |
|---|---|---|
| SEQ ID NO: 122 | VL | DIQMTQSPSSLSASVGDRVTITCRASQGISNWLAWYQ<br>QKPGKAPKLLIYGASSLQSGVPSRFSGSGSGTDFTLT<br>ISSLQPEDFATYYCQQYSSFPTTFGQGTKVEIK |
| SEQ ID NO: 123 | VH | EVQLLESGGGLVQPGGSLRLSCAASGFTFSSYAMSWV<br>RQAPGKGLEWVSVISAWGHVKYYADSVKGRFTISRDN<br>SKNTLYLQMNSLRAEDTAVYYCARWGDEGFDIWGQGT<br>LVTVSS |
| SEQ ID NO: 124 | DNA VL | GATATCCAGATGACCCAGAGCCCCAGCAGCCTGAGCG<br>CCAGCGTGGGCGACAGAGTGACCATCACCTGTCGGGC<br>CAGCCAGGGCATCAGCAACTGGCTGGCCTGGTATCAG<br>CAGAAGCCCGGCAAGGCCCCCAAGCTGCTGATCTACG<br>GCGCCAGCTCCCTGCAGAGCGGCGTGCCAAGCAGATT<br>CAGCGGCAGCGGCTCCGGCACCGACTTCACCCTGACC<br>ATCAGCAGCCTGCAGCCCGAGGACTTCGCCACCTACT<br>ACTGCCAGCAGTACAGCAGCTTCCCCACCACCTTCGG<br>CCAGGGCACCAAGGTGGAAATCAAG |
| SEQ ID NO: 125 | DNA VH | GAGGTGCAATTGCTGGAAAGCGGCGGAGGCCTGGTGC<br>AGCCTGGCGGCAGCCTGAGACTGTCTTGCGCCGCCAG<br>CGGCTTCACCTTCAGCAGCTACGCCATGAGCTGGGTC<br>CGCCAGGCCCCTGGCAAGGGACTGGAATGGGTGTCCG<br>TGATCAGCGCCTGGGGCCACGTGAAGTACTACGCCGA<br>CAGCGTGAAGGGCCGGTTCACCATCAGCCGGGACAAC<br>AGCAAGAACACCCTGTACCTGCAGATGAACAGCCTGC<br>GGGCCGAGGACACCGCCGTGTACTACTGTGCCAGATG<br>GGGCGACGAGGGCTTCGACATCTGGGGCCAGGGCACC<br>CTGGTCACCGTCAGCTCA |
| SEQ ID NO: 126 | Light Kappa | DIQMTQSPSSLSASVGDRVTITCRASQGISNWLAWYQ<br>QKPGKAPKLLIYGASSLQSGVPSRFSGSGSGTDFTLT<br>ISSLQPEDFATYYCQQYSSFPTTFGQGTKVEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC |
| SEQ ID NO: 127 | Heavy IgG1 | EVQLLESGGGLVQPGGSLRLSCAASGFTFSSYAMSWV<br>RQAPGKGLEWVSVISAWGHVKYYADSVKGRFTISRDN<br>SKNTLYLQMNSLRAEDTAVYYCARWGDEGFDIWGQGT<br>LVTVSSASTKGPSVFPLAPSSKSTSGGTAALGCLVKD<br>YFPEPVTVSWNSGALTSGVHTFPAVLQSSGLYSLSSV<br>VTVPSSSLGTQTYICNVNHKPSNTKVDKRVEPKSCDK<br>THTCPPCPAPELLGGPSVFLFPPKPKDTLMISRTPEV<br>TCVVVDVSHEDPEVKFNWYVDGVEVHNAKTKPREEQY<br>NSTYRVVSVLTVLHQDWLNGKEYKCKVSNKALPAPIE<br>KTISKAKGQPREPQVYTLPPSREEMTKNQVSLTCLVK<br>GFYPSDIAVEWESNGQPENNYKTTPPVLDSDGSFFLY<br>SKLTVDKSRWQQGNVFSCSVMHEALHNHYTQKSLSLS<br>PGK |
| MOR10703 | | |
| SEQ ID NO: 128 (Kabat) | HCDR1 | SYAMS |
| SEQ ID NO: 129 (Kabat) | HCDR2 | AINSQGKSTYYADSVKG |
| SEQ ID NO: 130 (Kabat) | HCDR3 | WGDEGFDI |
| SEQ ID NO: 131 (Kabat) | LCDR1 | RASQGISNWLA |
| SEQ ID NO: 132 (Kabat) | LCDR2 | GASSLQS |
| SEQ ID NO: 133 (Kabat) | LCDR3 | QQYSSFPTT |
| SEQ ID NO: 134 (Chothia) | HCDR1 | GFTFSSY |
| SEQ ID NO: 135 (Chothia) | HCDR2 | NSQGKS |
| SEQ ID NO: 136 (Chothia) | HCDR3 | WGDEGFDI |
| SEQ ID NO: 137 (Chothia) | LCDR1 | SQGISNW |
| SEQ ID NO: 138 (Chothia) | LCDR2 | GAS |
| SEQ ID NO: 139 (Chothia) | LCDR3 | YSSFPT |
| SEQ ID NO: 140 | VL | DIQMTQSPSSLSASVGDRVTITCRASQGISNWLAWYQ<br>QKPGKAPKLLIYGASSLQSGVPSRFSGSGSGTDFTLT<br>ISSLQPEDFATYYCQQYSSFPTTFGQGTKVEIK |

TABLE 1-continued

Examples of HER3 Antibodies useful in the methods of the Present Invention

| SEQ ID NUMBER | Ab region | |
|---|---|---|
| SEQ ID NO: 141 | VH | EVQLLESGGGLVQPGGSLRLSCAASGFTFSSYAMSWV RQAPGKGLEWVSAINSQGKSTYYADSVKGRFTISRDN SKNTLYLQMNSLRAEDTAVYYCARWGDEGFDIWGQGT LVTVSS |
| SEQ ID NO: 142 | DNA VL | GATATCCAGATGACCCAGAGCCCCAGCAGCCTGAGCG CCAGCGTGGGCGACAGAGTGACCATCACCTGTCGGGC CAGCCAGGGCATCAGCAACTGGCTGGCCTGGTATCAG CAGAAGCCCGGCAAGGCCCCCAAGCTGCTGATCTACG GCGCCAGCTCCCTGCAGAGCGGCGTGCCAAGCAGATT CAGCGGCAGCGGCTCCGGCACCGACTTCACCCTGACC ATCAGCAGCCTGCAGCCCGAGGACTTCGCCACCTACT ACTGCCAGCAGTACAGCAGCTTCCCCACCACCTTCGG CCAGGGCACCAAGGTGGAAATCAAG |
| SEQ ID NO: 143 | DNA VH | GAGGTGCAATTGCTGGAAAGCGGCGGAGGCCTGGTGC AGCCTGGCGGCAGCCTGAGACTGTCTTGCGCCGCCAG CGGCTTCACCTTCAGCAGCTACGCCATGAGCTGGGTC CGCCAGGCCCCTGGCAAGGGACTGGAATGGGTGTCCG CCATCAACAGCCAGGGCAAGAGCACCTACTACGCCGA CAGCGTGAAGGGCCGGTTCACCATCAGCCGGGACAAC AGCAAGAACACCCTGTACCTGCAGATGAACAGCCTGC GGGCCGAGGACACCGCCGTGTACTACTGTGCCAGATG GGGCGACGAGGGCTTCGACATCTGGGGCCAGGGCACC CTGGTCACCGTCAGCTCA |
| SEQ ID NO: 144 | Light Kappa | DIQMTQSPSSLSASVGDRVTITCRASQGISNWLAWYQ QKPGKAPKLLIYGASSLQSGVPSRFSGSGSGTDFTLT ISSLQPEDFATYYCQQYSSFPTTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 145 | Heavy IgG1 | EVQLLESGGGLVQPGGSLRLSCAASGFTFSSYAMSWV RQAPGKGLEWVSAINSQGKSTYYADSVKGRFTISRDN SKNTLYLQMNSLRAEDTAVYYCARWGDEGFDIWGQGT LVTVSSASTKGPSVFPLAPSSKSTSGGTAALGCLVKD YFPEPVTVSWNSGALTSGVHTFPAVLQSSGLYSLSSV VTVPSSSLGTQTYICNVNHKPSNTKVDKRVEPKSCDK THTCPPCPAPELLGGPSVFLFPPKPKDTLMISRTPEV TCVVVDVSHEDPEVKFNWYVDGVEVHNAKTKPREEQY NSTYRVVSVLTVLHQDWLNGKEYKCKVSNKALPAPIE KTISKAKGQPREPQVYTLPPSREEMTKNQVSLTCLVK GFYPSDIAVEWESNGQPENNYKTTPPVLDSDGSFFLY SKLTVDKSRWQQGNVFSCSVMHEALHNHYTQKSLSLS PGK |
| MOR10703 N52S | | |
| SEQ ID NO: 146 (Kabat) | HCDR1 | SYAMS |
| SEQ ID NO: 147 (Kabat) | HCDR2 | AISSQGKSTYYADSVKG |
| SEQ ID NO: 148 (Kabat) | HCDR3 | WGDEGFDI |
| SEQ ID NO: 149 (Kabat) | LCDR1 | RASQGISNWLA |
| SEQ ID NO: 150 (Kabat) | LCDR2 | GASSLQS |
| SEQ ID NO: 151 (Kabat) | LCDR3 | QQYSSFPTT |
| SEQ ID NO: 152 (Chothia) | HCDR1 | GFTFSSY |
| SEQ ID NO: 153 (Chothia) | HCDR2 | SSQGKS |
| SEQ ID NO: 154 (Chothia) | HCDR3 | WGDEGFDI |
| SEQ ID NO: 155 (Chothia) | LCDR1 | SQGISNW |
| SEQ ID NO: 156 (Chothia) | LCDR2 | GAS |
| SEQ ID NO: 157 (Chothia) | LCDR3 | YSSFPT |
| SEQ ID NO: 158 | VL | DIQMTQSPSSLSASVGDRVTITCRASQGISNWLAWYQ QKPGKAPKLLIYGASSLQSGVPSRFSGSGSGTDFTLT ISSLQPEDFATYYCQQYSSFPTTFGQGTKVEIK |

TABLE 1-continued

Examples of HER3 Antibodies useful in the methods of the Present Invention

| SEQ ID NUMBER | Ab region | |
|---|---|---|
| SEQ ID NO: 159 | VH | EVQLLESGGGLVQPGGSLRLSCAASGFTFSSYAMSWV RQAPGKGLEWVSAISSQGKSTYYADSVKGRFTISRDN SKNTLYLQMNSLRAEDTAVYYCARWGDEGFDIWGQGT LVTVSS |
| SEQ ID NO: 160 | DNA VL | GATATCCAGATGACCCAGAGCCCCAGCAGCCTGAGCG CCAGCGTGGGCGACAGAGTGACCATCACCTGTCGGGC CAGCCAGGGCATCAGCAACTGGCTGGCCTGGTATCAG CAGAAGCCCGGCAAGGCCCCCAAGCTGCTGATCTACG GCGCCAGCTCCCTGCAGAGCGGCGTGCCAAGCAGATT CAGCGGCAGCGGCTCCGGCACCGACTTCACCCTGACC ATCAGCAGCCTGCAGCCCGAGGACTTCGCCACCTACT ACTGCCAGCAGTACAGCAGCTTCCCCACCACCTTCGG CCAGGGCACCAAGGTGGAAATCAAG |
| SEQ ID NO: 161 | DNA VH | GAGGTGCAATTGCTGGAAAGCGGCGGAGGCCTGGTGC AGCCTGGCGGCAGCCTGAGACTGTCTTGCGCCGCCAG CGGCTTCACCTTCAGCAGCTACGCCATGAGCTGGGTC CGCCAGGCCCCTGGCAAGGGACTGGAATGGGTGTCCG CCATCAGCAGCCAGGGCAAGAGCACCTACTACGCCGA CAGCGTGAAGGGCCGGTTCACCATCAGCCGGGACAAC AGCAAGAACACCCTGTACCTGCAGATGAACAGCCTGC GGGCCGAGGACACCGCCGTGTACTACTGTGCCAGATG GGGCGACGAGGGCTTCGACATCTGGGGCCAGGGCACC CTGGTCACCGTCAGCTCA |
| SEQ ID NO: 162 | Light Kappa | DIQMTQSPSSLSASVGDRVTITCRASQGISNWLAWYQ QKPGKAPKLLIYGASSLQSGVPSRFSGSGSGTDFTLT ISSLQPEDFATYYCQQYSSFPTTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 163 | Heavy IgG1 | EVQLLESGGGLVQPGGSLRLSCAASGFTFSSYAMSWV RQAPGKGLEWVSAISSQGKSTYYADSVKGRFTISRDN SKNTLYLQMNSLRAEDTAVYYCARWGDEGFDIWGQGT LVTVSSASTKGPSVFPLAPSSKSTSGGTAALGCLVKD YFPEPVTVSWNSGALTSGVHTFPAVLQSSGLYSLSSV VTVPSSSLGTQTYICNVNHKPSNTKVDKRVEPKSCDK THTCPPCPAPELLGGPSVFLFPPKPKDTLMISRTPEV TCVVVDVSHEDPEVKFNWYVDGVEVHNAKTKPREEQY NSTYRVVSVLTVLHQDWLNGKEYKCKVSNKALPAPIE KTISKAKGQPREPQVYTLPPSREEMTKNQVSLTCLVK GFYPSDIAVEWESNGQPENNYKTTPPVLDSDGSFFLY SKLTVDKSRWQQGNVFSCSVMHEALHNHYTQKSLSLS PGK |

MOR10703 N52G

| SEQ ID NO: 164 (Kabat) | HCDR1 | SYAMS |
| SEQ ID NO: 165 (Kabat) | HCDR2 | AIGSQGKSTYYADSVKG |
| SEQ ID NO: 166 (Kabat) | HCDR3 | WGDEGFDI |
| SEQ ID NO: 167 (Kabat) | LCDR1 | RASQGISNWLA |
| SEQ ID NO: 168 (Kabat) | LCDR2 | GASSLQS |
| SEQ ID NO: 169 (Kabat) | LCDR3 | QQYSSFPTT |
| SEQ ID NO: 170 (Chothia) | HCDR1 | GFTFSSY |
| SEQ ID NO: 171 (Chothia) | HCDR2 | GSQGKS |
| SEQ ID NO: 172 (Chothia) | HCDR3 | WGDEGFDI |
| SEQ ID NO: 173 (Chothia) | LCDR1 | SQGISNW |
| SEQ ID NO: 174 (Chothia) | LCDR2 | GAS |
| SEQ ID NO: 175 (Chothia) | LCDR3 | YSSFPT |
| SEQ ID NO: 176 | VL | DIQMTQSPSSLSASVGDRVTITCRASQGISNWLAWYQ QKPGKAPKLLIYGASSLQSGVPSRFSGSGSGTDFTLT ISSLQPEDFATYYCQQYSSFPTTFGQGTKVEIK |

TABLE 1-continued

Examples of HER3 Antibodies useful in the methods of the Present Invention

| SEQ ID NUMBER | Ab region | |
|---|---|---|
| SEQ ID NO: 177 | VH | EVQLLESGGGLVQPGGSLRLSCAASGFTFSSYAMSWV RQAPGKGLEWVSAIGSQGKSTYYADSVKGRFTISRDN SKNTLYLQMNSLRAEDTAVYYCARWGDEGFDIWGQGT LVTVSS |
| SEQ ID NO: 178 | DNA VL | GATATCCAGATGACCCAGAGCCCCAGCAGCCTGAGCG CCAGCGTGGGCGACAGAGTGACCATCACCTGTCGGGC CAGCCAGGGCATCAGCAACTGGCTGGCCTGGTATCAG CAGAAGCCCGGCAAGGCCCCCAAGCTGCTGATCTACG GCGCCAGCTCCCTGCAGAGCGGCGTGCCAAGCAGATT CAGCGGCAGCGGCTCCGGCACCGACTTCACCCTGACC ATCAGCAGCCTGCAGCCCGAGGACTTCGCCACCTACT ACTGCCAGCAGTACAGCAGCTTCCCCACCACCTTCGG CCAGGGCACCAAGGTGGAAATCAAG |
| SEQ ID NO: 179 | DNA VH | GAGGTGCAATTGCTGGAAAGCGGCGGAGGCCTGGTGC AGCCTGGCGGCAGCCTGAGACTGTCTTGCGCCGCCAG CGGCTTCACCTTCAGCAGCTACGCCATGAGCTGGGTC CGCCAGGCCCCTGGCAAGGGACTGGAATGGGTGTCCG CCATCGGCAGCCAGGGCAAGAGCACCTACTACGCCGA CAGCGTGAAGGGCCGGTTCACCATCAGCCGGGACAAC AGCAAGAACACCCTGTACCTGCAGATGAACAGCCTGC GGGCCGAGGACACCGCCGTGTACTACTGTGCCAGATG GGGCGACGAGGGCTTCGACATCTGGGGCCAGGGCACC CTGGTCACCGTCAGCTCA |
| SEQ ID NO: 180 | Light Kappa | DIQMTQSPSSLSASVGDRVTITCRASQGISNWLAWYQ QKPGKAPKLLIYGASSLQSGVPSRFSGSGSGTDFTLT ISSLQPEDFATYYCQQYSSFPTTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 181 | Heavy IgG1 | EVQLLESGGGLVQPGGSLRLSCAASGFTFSSYAMSWV RQAPGKGLEWVSAIGSQGKSTYYADSVKGRFTISRDN SKNTLYLQMNSLRAEDTAVYYCARWGDEGFDIWGQGT LVTVSSASTKGPSVFPLAPSSKSTSGGTAALGCLVKD YFPEPVTVSWNSGALTSGVHTFPAVLQSSGLYSLSSV VTVPSSSLGTQTYICNVNHKPSNTKVDKRVEPKSCDK THTCPPCPAPELLGGPSVFLFPPKPKDTLMISRTPEV TCVVVDVSHEDPEVKFNWYVDGVEVHNAKTKPREEQY NSTYRVVSVLTVLHQDWLNGKEYKCKVSNKALPAPIE KTISKAKGQPREPQVYTLPPSREEMTKNQVSLTCLVK GFYPSDIAVEWESNGQPENNYKTTPPVLDSDGSFFLY SKLTVDKSRWQQGNVFSCSVMHEALHNHYTQKSLSLS PGK |

MOR10703 N52S_S52aN

| SEQ ID NO: 182 (Kabat) | HCDR1 | SYAMS |
| SEQ ID NO: 183 (Kabat) | HCDR2 | AISNQGKSTYYADSVKG |
| SEQ ID NO: 184 (Kabat) | HCDR3 | WGDEGFDI |
| SEQ ID NO: 185 (Kabat) | LCDR1 | RASQGISNWLA |
| SEQ ID NO: 186 (Kabat) | LCDR2 | GASSLQS |
| SEQ ID NO: 187 (Kabat) | LCDR3 | QQYSSFPTT |
| SEQ ID NO: 188 (Chothia) | HCDR1 | GFTFSSY |
| SEQ ID NO: 189 (Chothia) | HCDR2 | SNQGKS |
| SEQ ID NO: 190 (Chothia) | HCDR3 | WGDEGFDI |
| SEQ ID NO: 191 (Chothia) | LCDR1 | SQGISNW |
| SEQ ID NO: 192 (Chothia) | LCDR2 | GAS |
| SEQ ID NO: 193 (Chothia) | LCDR3 | YSSFPT |
| SEQ ID NO: 194 | VL | DIQMTQSPSSLSASVGDRVTITCRASQGISNWLAWYQ QKPGKAPKLLIYGASSLQSGVPSRFSGSGSGTDFTLT ISSLQPEDFATYYCQQYSSFPTTFGQGTKVEIK |

TABLE 1-continued

Examples of HER3 Antibodies useful in the methods of the Present Invention

| SEQ ID NUMBER | Ab region | |
|---|---|---|
| SEQ ID NO: 195 | VH | EVQLLESGGGLVQPGGSLRLSCAASGFTFSSYAMSWV
RQAPGKGLEWVSAISNQGKSTYYADSVKGRFTISRDN
SKNTLYLQMNSLRAEDTAVYYCARWGDEGFDIWGQGT
LVTVSS |
| SEQ ID NO: 196 | DNA VL | GATATCCAGATGACCCAGAGCCCCAGCAGCCTGAGCG
CCAGCGTGGGCGACAGAGTGACCATCACCTGTCGGGC
CAGCCAGGGCATCAGCAACTGGCTGGCCTGGTATCAG
CAGAAGCCCGGCAAGGCCCCCAAGCTGCTGATCTACG
GCGCCAGCTCCCTGCAGAGCGGCGTGCCAAGCAGATT
CAGCGGCAGCGGCTCCGGCACCGACTTCACCCTGACC
ATCAGCAGCCTGCAGCCCGAGGACTTCGCCACCTACT
ACTGCCAGCAGTACAGCAGCTTCCCCACCACCTTCGG
CCAGGGCACCAAGGTGGAAATCAAG |
| SEQ ID NO: 197 | DNA VH | GAGGTGCAATTGCTGGAAAGCGGCGGAGGCCTGGTGC
AGCCTGGCGGCAGCCTGAGACTGTCTTGCGCCGCCAG
CGGCTTCACCTTCAGCAGCTACGCCATGAGCTGGGTC
CGCCAGGCCCCTGGCAAGGGACTGGAATGGGTGTCCG
CCATCAGCAACCAGGGCAAGAGCACCTACTACGCCGA
CAGCGTGAAGGGCCGGTTCACCATCAGCCGGGACAAC
AGCAAGAACACCCTGTACCTGCAGATGAACAGCCTGC
GGGCCGAGGACACCGCCGTGTACTACTGTGCCAGATG
GGGCGACGAGGGCTTCGACATCTGGGGCCAGGGCACC
CTGGTCACCGTCAGCTCA |
| SEQ ID NO: 198 | Light Kappa | DIQMTQSPSSLSASVGDRVTITCRASQGISNWLAWYQ
QKPGKAPKLLIYGASSLQSGVPSRFSGSGSGTDFTLT
ISSLQPEDFATYYCQQYSSFPTTFGQGTKVEIKRTVA
APSVFIFPPSDEQLKSGTASVVCLLNNFYPREAKVQW
KVDNALQSGNSQESVTEQDSKDSTYSLSSTLTLSKAD
YEKHKVYACEVTHQGLSSPVTKSFNRGEC |
| SEQ ID NO: 199 | Heavy IgG1 | EVQLLESGGGLVQPGGSLRLSCAASGFTFSSYAMSWV
RQAPGKGLEWVSAISNQGKSTYYADSVKGRFTISRDN
SKNTLYLQMNSLRAEDTAVYYCARWGDEGFDIWGQGT
LVTVSSASTKGPSVFPLAPSSKSTSGGTAALGCLVKD
YFPEPVTVSWNSGALTSGVHTFPAVLQSSGLYSLSSV
VTVPSSSLGTQTYICNVNHKPSNTKVDKRVEPKSCDK
THTCPPCPAPELLGGPSVFLFPPKPKDTLMISRTPEV
TCVVVDVSHEDPEVKFNWYVDGVEVHNAKTKPREEQY
NSTYRVVSVLTVLHQDWLNGKEYKCKVSNKALPAPIE
KTISKAKGQPREPQVYTLPPSREEMTKNQVSLTCLVK
GFYPSDIAVEWESNGQPENNYKTTPPVLDSDGSFFLY
SKLTVDKSRWQQGNVFSCSVMHEALHNHYTQKSLSLS
PGK |
| MOR10703 A50V_N52S | | |
| SEQ ID NO: 200 (Kabat) | HCDR1 | SYAMS |
| SEQ ID NO: 201 (Kabat) | HCDR2 | VIS SQGKSTYYADSVKG |
| SEQ ID NO: 202 (Kabat) | HCDR3 | WGDEGFDI |
| SEQ ID NO: 203 (Kabat) | LCDR1 | RASQGISNWLA |
| SEQ ID NO: 204 (Kabat) | LCDR2 | GASSLQS |
| SEQ ID NO: 205 (Kabat) | LCDR3 | QQYSSFPTT |
| SEQ ID NO: 206 (Chothia) | HCDR1 | GFTFSSY |
| SEQ ID NO: 207 (Chothia) | HCDR2 | SSQGKS |
| SEQ ID NO: 208 (Chothia) | HCDR3 | WGDEGFDI |
| SEQ ID NO: 209 (Chothia) | LCDR1 | SQGISNW |
| SEQ ID NO: 210 (Chothia) | LCDR2 | GAS |
| SEQ ID NO: 211 (Chothia) | LCDR3 | YSSFPT |
| SEQ ID NO: 212 | VL | DIQMTQSPSSLSASVGDRVTITCRASQGISNWLAWYQ
QKPGKAPKLLIYGASSLQSGVPSRFSGSGSGTDFTLT
ISSLQPEDFATYYCQQYSSFPTTFGQGTKVEIK |

TABLE 1-continued

Examples of HER3 Antibodies useful in the methods of the Present Invention

| SEQ ID NUMBER | Ab region | |
|---|---|---|
| SEQ ID NO: 213 | VH | EVQLLESGGGLVQPGGSLRLSCAASGFTFSSYAMSWV RQAPGKGLEWVSVISSQGKSTYYADSVKGRFTISRDN SKNTLYLQMNSLRAEDTAVYYCARWGDEGFDIWGQGT LVTVSS |
| SEQ ID NO: 214 | DNA VL | GATATCCAGATGACCCAGAGCCCCAGCAGCCTGAGCG CCAGCGTGGGCGACAGAGTGACCATCACCTGTCGGGC CAGCCAGGGCATCAGCAACTGGCTGGCCTGGTATCAG CAGAAGCCCGGCAAGGCCCCCAAGCTGCTGATCTACG GCGCCAGCTCCCTGCAGAGCGGCGTGCCAAGCAGATT CAGCGGCAGCGGCTCCGGCACCGACTTCACCCTGACC ATCAGCAGCCTGCAGCCCGAGGACTTCGCCACCTACT ACTGCCAGCAGTACAGCAGCTTCCCCACCACCTTCGG CCAGGGCACCAAGGTGGAAATCAAG |
| SEQ ID NO: 215 | DNA VH | GAGGTGCAATTGCTGGAAAGCGGCGGAGGCCTGGTGC AGCCTGGCGGCAGCCTGAGACTGTCTTGCGCCGCCAG CGGCTTCACCTTCAGCAGCTACGCCATGAGCTGGGTC CGCCAGGCCCCTGGCAAGGGACTGGAATGGGTGTCCG TCATCAGCAGCCAGGGCAAGAGCACCTACTACGCCGA CAGCGTGAAGGGCCGGTTCACCATCAGCCGGGACAAC AGCAAGAACACCCTGTACCTGCAGATGAACAGCCTGC GGGCCGAGGACACCGCCGTGTACTACTGTGCCAGATG GGGCGACGAGGGCTTCGACATCTGGGGCCAGGGCACC CTGGTCACCGTCAGCTCA |
| SEQ ID NO: 216 | Light Kappa | DIQMTQSPSSLSASVGDRVTITCRASQGISNWLAWYQ QKPGKAPKLLIYGASSLQSGVPSRFSGSGSGTDFTLT ISSLQPEDFATYYCQQYSSFPTTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 217 | Heavy IgG1 | EVQLLESGGGLVQPGGSLRLSCAASGFTFSSYAMSWV RQAPGKGLEWVSVISSQGKSTYYADSVKGRFTISRDN SKNTLYLQMNSLRAEDTAVYYCARWGDEGFDIWGQGT LVTVSSASTKGPSVFPLAPSSKSTSGGTAALGCLVKD YFPEPVTVSWNSGALTSGVHTFPAVLQSSGLYSLSSV VTVPSSSLGTQTYICNVNHKPSNTKVDKRVEPKSCDK THTCPPCPAPELLGGPSVFLFPPKPKDTLMISRTPEV TCVVVDVSHEDPEVKFNWYVDGVEVHNAKTKPREEQY NSTYRVVSVLTVLHQDWLNGKEYKCKVSNKALPAPIE KTISKAKGQPREPQVYTLPPSREEMTKNQVSLTCLVK GFYPSDIAVEWESNGQPENNYKTTPPVLDSDGSFFLY SKLTVDKSRWQQGNVFSCSVMHEALHNHYTQKSLSLS PGK |

MOR10703_A50V_N52G

| SEQ ID NO: 218 (Kabat) | HCDR1 | SYAMS |
|---|---|---|
| SEQ ID NO: 219 (Kabat) | HCDR2 | VIG**SQGKSTYYADSVKG |
| SEQ ID NO: 220 (Kabat) | HCDR3 | WGDEGFDI |
| SEQ ID NO: 221 (Kabat) | LCDR1 | RASQGISNWLA |
| SEQ ID NO: 222 (Kabat) | LCDR2 | GASSLQS |
| SEQ ID NO: 223 (Kabat) | LCDR3 | QQYSSFPTT |
| SEQ ID NO: 224 (Chothia) | HCDR1 | GFTFSSY |
| SEQ ID NO: 225 (Chothia) | HCDR2 | GSQGKS |
| SEQ ID NO: 226 (Chothia) | HCDR3 | WGDEGFDI |
| SEQ ID NO: 227 (Chothia) | LCDR1 | SQGISNW |
| SEQ ID NO: 228 (Chothia) | LCDR2 | GAS |
| SEQ ID NO: 229 (Chothia) | LCDR3 | YSSFPT |
| SEQ ID NO: 230 | VL | DIQMTQSPSSLSASVGDRVTITCRASQGISNWLAWYQ QKPGKAPKLLIYGASSLQSGVPSRFSGSGSGTDFTLT ISSLQPEDFATYYCQQYSSFPTTFGQGTKVEIK |

TABLE 1-continued

Examples of HER3 Antibodies useful in the methods of the Present Invention

| SEQ ID NUMBER | Ab region | |
|---|---|---|
| SEQ ID NO: 231 | VH | EVQLLESGGGLVQPGGSLRLSCAASGFTFSSYAMSWV RQAPGKGLEWVSVIGSQGKSTYYADSVKGRFTISRDN SKNTLYLQMNSLRAEDTAVYYCARWGDEGFDIWGQGT LVTVSS |
| SEQ ID NO: 232 | DNA VL | GATATCCAGATGACCCAGAGCCCCAGCAGCCTGAGCG CCAGCGTGGGCGACAGAGTGACCATCACCTGTCGGGC CAGCCAGGGCATCAGCAACTGGCTGGCCTGGTATCAG CAGAAGCCCGGCAAGGCCCCCAAGCTGCTGATCTACG GCGCCAGCTCCCTGCAGAGCGGCGTGCCAAGCAGATT CAGCGGCAGCGGCTCCGGCACCGACTTCACCCTGACC ATCAGCAGCCTGCAGCCCGAGGACTTCGCCACCTACT ACTGCCAGCAGTACAGCAGCTTCCCCACCACCTTCGG CCAGGGCACCAAGGTGGAAATCAAG |
| SEQ ID NO: 233 | DNA VH | GAGGTGCAATTGCTGGAAAGCGGCGGAGGCCTGGTGC AGCCTGGCGGCAGCCTGAGACTGTCTTGCGCCGCCAG CGGCTTCACCTTCAGCAGCTACGCCATGAGCTGGGTC CGCCAGGCCCCTGGCAAGGGACTGGAATGGGTGTCCG TCATCGGCAGCCAGGGCAAGAGCACCTACTACGCCGA CAGCGTGAAGGGCCGGTTCACCATCAGCCGGGACAAC AGCAAGAACACCCTGTACCTGCAGATGAACAGCCTGC GGGCCGAGGACACCGCCGTGTACTACTGTGCCAGATG GGGCGACGAGGGCTTCGACATCTGGGGCCAGGGCACC CTGGTCACCGTCAGCTCA |
| SEQ ID NO: 234 | Light Kappa | DIQMTQSPSSLSASVGDRVTITCRASQGISNWLAWYQ QKPGKAPKLLIYGASSLQSGVPSRFSGSGSGTDFTLT ISSLQPEDFATYYCQQYSSFPTTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 235 | Heavy IgG1 | EVQLLESGGGLVQPGGSLRLSCAASGFTFSSYAMSWV RQAPGKGLEWVSVIGSQGKSTYYADSVKGRFTISRDN SKNTLYLQMNSLRAEDTAVYYCARWGDEGFDIWGQGT LVTVSSASTKGPSVFPLAPSSKSTSGGTAALGCLVKD YFPEPVTVSWNSGALTSGVHTFPAVLQSSGLYSLSSV VTVPSSSLGTQTYICNVNHKPSNTKVDKRVEPKSCDK THTCPPCPAPELLGGPSVFLFPPKPKDTLMISRTPEV TCVVVDVSHEDPEVKFNWYVDGVEVHNAKTKPREEQY NSTYRVVSVLTVLHQDWLNGKEYKCKVSNKALPAPIE KTISKAKGQPREPQVYTLPPSREEMTKNQVSLTCLVK GFYPSDIAVEWESNGQPENNYKTTPPVLDSDGSFFLY SKLTVDKSRWQQGNVFSCSVMHEALHNHYTQKSLSLS PGK |
| MOR10703 S52aA | | |
| SEQ ID NO: 236 (Kabat) | HCDR1 | SYAMS |
| SEQ ID NO: 237 (Kabat) | HCDR2 | AINAQGKSTYYADSVKG |
| SEQ ID NO: 238 (Kabat) | HCDR3 | WGDEGFDI |
| SEQ ID NO: 239 (Kabat) | LCDR1 | RASQGISNWLA |
| SEQ ID NO: 240 (Kabat) | LCDR2 | GASSLQS |
| SEQ ID NO: 241 (Kabat) | LCDR3 | QQYSSFPTT |
| SEQ ID NO: 242 (Chothia) | HCDR1 | GFTFSSY |
| SEQ ID NO: 243 (Chothia) | HCDR2 | NAQGKS |
| SEQ ID NO: 244 (Chothia) | HCDR3 | WGDEGFDI |
| SEQ ID NO: 245 (Chothia) | LCDR1 | SQGISNW |
| SEQ ID NO: 246 (Chothia) | LCDR2 | GAS |
| SEQ ID NO: 247 (Chothia) | LCDR3 | YSSFPT |
| SEQ ID NO: 248 | VL | DIQMTQSPSSLSASVGDRVTITCRASQGISNWLAWYQ QKPGKAPKLLIYGASSLQSGVPSRFSGSGSGTDFTLT ISSLQPEDFATYYCQQYSSFPTTFGQGTKVEIK |

TABLE 1-continued

Examples of HER3 Antibodies useful in the methods of the Present Invention

| SEQ ID NUMBER | Ab region | |
|---|---|---|
| SEQ ID NO: 249 | VH | EVQLLESGGGLVQPGGSLRLSCAASGFTFSSYAMSWV RQAPGKGLEWVSAINAQGKSTYYADSVKGRFTISRDN SKNTLYLQMNSLRAEDTAVYYCARWGDEGFDIWGQGT LVTVSS |
| SEQ ID NO: 250 | DNA VL | GATATCCAGATGACCCAGAGCCCCAGCAGCCTGAGCG CCAGCGTGGGCGACAGAGTGACCATCACCTGTCGGGC CAGCCAGGGCATCAGCAACTGGCTGGCCTGGTATCAG CAGAAGCCCGGCAAGGCCCCCAAGCTGCTGATCTACG GCGCCAGCTCCCTGCAGAGCGGCGTGCCAAGCAGATT CAGCGGCAGCGGCTCCGGCACCGACTTCACCCTGACC ATCAGCAGCCTGCAGCCCGAGGACTTCGCCACCTACT ACTGCCAGCAGTACAGCAGCTTCCCCACCACCTTCGG CCAGGGCACCAAGGTGGAAATCAAG |
| SEQ ID NO: 251 | DNA VH | GAGGTGCAATTGCTGGAAAGCGGCGGAGGCCTGGTGC AGCCTGGCGGCAGCCTGAGACTGTCTTGCGCCGCCAG CGGCTTCACCTTCAGCAGCTACGCCATGAGCTGGGTC CGCCAGGCCCCTGGCAAGGGACTGGAATGGGTGTCCG CCATCAACGCCCAGGGCAAGAGCACCTACTACGCCGA CAGCGTGAAGGGCCGGTTCACCATCAGCCGGGACAAC AGCAAGAACACCCTGTACCTGCAGATGAACAGCCTGC GGGCCGAGGACACCGCCGTGTACTACTGTGCCAGATG GGGCGACGAGGGCTTCGACATCTGGGGCCAGGGCACC CTGGTCACCGTCAGCTCA |
| SEQ ID NO: 252 | Light Kappa | DIQMTQSPSSLSASVGDRVTITCRASQGISNWLAWYQ QKPGKAPKLLIYGASSLQSGVPSRFSGSGSGTDFTLT ISSLQPEDFATYYCQQYSSFPTTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 253 | Heavy IgG1 | EVQLLESGGGLVQPGGSLRLSCAASGFTFSSYAMSWV RQAPGKGLEWVSAINAQGKSTYYADSVKGRFTISRDN SKNTLYLQMNSLRAEDTAVYYCARWGDEGFDIWGQGT LVTVSSASTKGPSVFPLAPSSKSTSGGTAALGCLVKD YFPEPVTVSWNSGALTSGVHTFPAVLQSSGLYSLSSV VTVPSSSLGTQTYICNVNHKPSNTKVDKRVEPKSCDK THTCPPCPAPELLGGPSVFLFPPKPKDTLMISRTPEV TCVVVDVSHEDPEVKFNWYVDGVEVHNAKTKPREEQY NSTYRVVSVLTVLHQDWLNGKEYKCKVSNKALPAPIE KTISKAKGQPREPQVYTLPPSREEMTKNQVSLTCLVK GFYPSDIAVEWESNGQPENNYKTTPPVLDSDGSFFLY SKLTVDKSRWQQGNVFSCSVMHEALHNHYTQKSLSLS PGK |

MOR10703 S52aT

| SEQ ID NO: 254 (Kabat) | HCDR1 | SYAMS |
| SEQ ID NO: 255 (Kabat) | HCDR2 | AINTQGKSTYYADSVKG |
| SEQ ID NO: 256 (Kabat) | HCDR3 | WGDEGFDI |
| SEQ ID NO: 257 (Kabat) | LCDR1 | RASQGISNWLA |
| SEQ ID NO: 258 (Kabat) | LCDR2 | GASSLQS |
| SEQ ID NO: 259 (Kabat) | LCDR3 | QQYSSFPTT |
| SEQ ID NO: 260 (Chothia) | HCDR1 | GFTFSSY |
| SEQ ID NO: 261 (Chothia) | HCDR2 | NTQGKS |
| SEQ ID NO: 262 (Chothia) | HCDR3 | WGDEGFDI |
| SEQ ID NO: 263 (Chothia) | LCDR1 | SQGISNW |
| SEQ ID NO: 264 (Chothia) | LCDR2 | GAS |
| SEQ ID NO: 265 (Chothia) | LCDR3 | YSSFPT |
| SEQ ID NO: 266 | VL | DIQMTQSPSSLSASVGDRVTITCRASQGISNWLAWYQ QKPGKAPKLLIYGASSLQSGVPSRFSGSGSGTDFTLT ISSLQPEDFATYYCQQYSSFPTTFGQGTKVEIK |

TABLE 1-continued

Examples of HER3 Antibodies useful in the methods of the Present Invention

| SEQ ID NUMBER | Ab region | |
|---|---|---|
| SEQ ID NO: 267 | VH | EVQLLESGGGLVQPGGSLRLSCAASGFTFSSYAMSWV RQAPGKGLEWVSAINTQGKSTYYADSVKGRFTISRDN SKNTLYLQMNSLRAEDTAVYYCARWGDEGFDIWGQGT LVTVSS |
| SEQ ID NO: 268 | DNA VL | GATATCCAGATGACCCAGAGCCCCAGCAGCCTGAGCG CCAGCGTGGGCGACAGAGTGACCATCACCTGTCGGGC CAGCCAGGGCATCAGCAACTGGCTGGCCTGGTATCAG CAGAAGCCCGGCAAGGCCCCCAAGCTGCTGATCTACG GCGCCAGCTCCCTGCAGAGCGGCGTGCCAAGCAGATT CAGCGGCAGCGGCTCCGGCACCGACTTCACCCTGACC ATCAGCAGCCTGCAGCCCGAGGACTTCGCCACCTACT ACTGCCAGCAGTACAGCAGCTTCCCCACCACCTTCGG CCAGGGCACCAAGGTGGAAATCAAG |
| SEQ ID NO: 269 | DNA VH | GAGGTGCAATTGCTGGAAAGCGGCGGAGGCCTGGTGC AGCCTGGCGGCAGCCTGAGACTGTCTTGCGCCGCCAG CGGCTTCACCTTCAGCAGCTACGCCATGAGCTGGGTC CGCCAGGCCCCTGGCAAGGGACTGGAATGGGTGTCCG CCATCAACACCCAGGGCAAGAGCACCTACTACGCCGA CAGCGTGAAGGGCCGGTTCACCATCAGCCGGGACAAC AGCAAGAACACCCTGTACCTGCAGATGAACAGCCTGC GGGCCGAGGACACCGCCGTGTACTACTGTGCCAGATG GGGCGACGAGGGCTTCGACATCTGGGGCCAGGGCACC CTGGTCACCGTCAGCTCA |
| SEQ ID NO: 270 | Light Kappa | DIQMTQSPSSLSASVGDRVTITCRASQGISNWLAWYQ QKPGKAPKLLIYGASSLQSGVPSRFSGSGSGTDFTLT ISSLQPEDFATYYCQQYSSFPTTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 271 | Heavy IgG1 | EVQLLESGGGLVQPGGSLRLSCAASGFTFSSYAMSWV RQAPGKGLEWVSAINTQGKSTYYADSVKGRFTISRDN SKNTLYLQMNSLRAEDTAVYYCARWGDEGFDIWGQGT LVTVSSASTKGPSVFPLAPSSKSTSGGTAALGCLVKD YFPEPVTVSWNSGALTSGVHTFPAVLQSSGLYSLSSV VTVPSSSLGTQTYICNVNHKPSNTKVDKRVEPKSCDK THTCPPCPAPELLGGPSVFLFPPKPKDTLMISRTPEV TCVVVDVSHEDPEVKFNWYVDGVEVHNAKTKPREEQY NSTYRVVSVLTVLHQDWLNGKEYKCKVSNKALPAPIE KTISKAKGQPREPQVYTLPPSREEMTKNQVSLTCLVK GFYPSDIAVEWESNGQPENNYKTTPPVLDSDGSFFLY SKLTVDKSRWQQGNVFSCSVMHEALHNHYTQKSLSLS PGK |
| MOR10701 R55S | | |
| SEQ ID NO: 272 (Kabat) | HCDR1 | SYAMS |
| SEQ ID NO: 273 (Kabat) | HCDR2 | VTGAVGSSTYYPDSVKG |
| SEQ ID NO: 274 (Kabat) | HCDR3 | WGDEGFDI |
| SEQ ID NO: 275 (Kabat) | LCDR1 | RASQGISNWLA |
| SEQ ID NO: 276 (Kabat) | LCDR2 | GASSLQS |
| SEQ ID NO: 277 (Kabat) | LCDR3 | QQYSSFPTT |
| SEQ ID NO: 278 (Chothia) | HCDR1 | GFTFSSY |
| SEQ ID NO: 279 (Chothia) | HCDR2 | GAVGSS |
| SEQ ID NO: 280 (Chothia) | HCDR3 | WGDEGFDI |
| SEQ ID NO: 281 (Chothia) | LCDR1 | SQGISNW |
| SEQ ID NO: 282 (Chothia) | LCDR2 | GAS |
| SEQ ID NO: 283 (Chothia) | LCDR3 | YSSFPT |
| SEQ ID NO: 284 | VL | DIQMTQSPSSLSASVGDRVTITCRASQGISNWLAWYQ QKPGKAPKLLIYGASSLQSGVPSRFSGSGSGTDFTLT ISSLQPEDFATYYCQQYSSFPTTFGQGTKVEIK |

TABLE 1-continued

Examples of HER3 Antibodies useful in the methods of the Present Invention

| SEQ ID NUMBER | Ab region | |
|---|---|---|
| SEQ ID NO: 285 | VH | EVQLLESGGGLVQPGGSLRLSCAASGFTFSSYAMSWV RQAPGKGLEWVSVTGAVGSSTYYPDSVKGRFTISRDN SKNTLYLQMNSLRAEDTAVYYCARWGDEGFDIWGQGT LVTVSS |
| SEQ ID NO: 286 | DNA VL | GATATCCAGATGACCCAGAGCCCCAGCAGCCTGAGCG CCAGCGTGGGCGACAGAGTGACCATCACCTGTCGGGC CAGCCAGGGCATCAGCAACTGGCTGGCCTGGTATCAG CAGAAGCCCGGCAAGGCCCCCAAGCTGCTGATCTACG GCGCCAGCTCCCTGCAGAGCGGCGTGCCAAGCAGATT CAGCGGCAGCGGCTCCGGCACCGACTTCACCCTGACC ATCAGCAGCCTGCAGCCCGAGGACTTCGCCACCTACT ACTGCCAGCAGTACAGCAGCTTCCCCACCACCTTCGG CCAGGGCACCAAGGTGGAAATCAAG |
| SEQ ID NO: 287 | DNA VH | GAGGTGCAATTGCTGGAAAGCGGCGGAGGCCTGGTGC AGCCTGGCGGCAGCCTGAGACTGTCTTGCGCCGCCAG CGGCTTCACCTTCAGCAGCTACGCCATGAGCTGGGTC CGCCAGGCCCCTGGCAAGGGACTGGAATGGGTGTCCG TGACAGGCGCCGTGGGCAGCAGCACCTACTACCCCGA CAGCGTGAAGGGCCGGTTCACCATCAGCCGGGACAAC AGCAAGAACACCCTGTACCTGCAGATGAACAGCCTGC GGGCCGAGGACACCGCCGTGTACTACTGTGCCAGATG GGGCGACGAGGGCTTCGACATCTGGGGCCAGGGCACC CTGGTCACCGTCAGCTCA |
| SEQ ID NO: 288 | Light Kappa | DIQMTQSPSSLSASVGDRVTITCRASQGISNWLAWYQ QKPGKAPKLLIYGASSLQSGVPSRFSGSGSGTDFTLT ISSLQPEDFATYYCQQYSSFPTTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 289 | Heavy IgG1 | EVQLLESGGGLVQPGGSLRLSCAASGFTFSSYAMSWV RQAPGKGLEWVSVTGAVGSSTYYPDSVKGRFTISRDN SKNTLYLQMNSLRAEDTAVYYCARWGDEGFDIWGQGT LVTVSSASTKGPSVFPLAPSSKSTSGGTAALGCLVKD YFPEPVTVSWNSGALTSGVHTFPAVLQSSGLYSLSSV VTVPSSSLGTQTYICNVNHKPSNTKVDKRVEPKSCDK THTCPPCPAPELLGGPSVFLFPPKPKDTLMISRTPEV TCVVVDVSHEDPEVKFNWYVDGVEVHNAKTKPREEQY NSTYRVVSVLTVLHQDWLNGKEYKCKVSNKALPAPIE KTISKAKGQPREPQVYTLPPSREEMTKNQVSLTCLVK GFYPSDIAVEWESNGQPENNYKTTPPVLDSDGSFFLY SKLTVDKSRWQQGNVFSCSVMHEALHNHYTQKSLSLS PGK |
| MOR10701 R55G | | |
| SEQ ID NO: 290 (Kabat) | HCDR1 | SYAMS |
| SEQ ID NO: 291 (Kabat) | HCDR2 | VTGAVGGSTYYPDSVKG |
| SEQ ID NO: 292 (Kabat) | HCDR3 | WGDEGFDI |
| SEQ ID NO: 293 (Kabat) | LCDR1 | RASQGISNWLA |
| SEQ ID NO: 294 (Kabat) | LCDR2 | GASSLQS |
| SEQ ID NO: 295 (Kabat) | LCDR3 | QQYSSFPTT |
| SEQ ID NO: 296 (Chothia) | HCDR1 | GFTFSSY |
| SEQ ID NO: 297 (Chothia) | HCDR2 | GAVGGS |
| SEQ ID NO: 298 (Chothia) | HCDR3 | WGDEGFDI |
| SEQ ID NO: 299 (Chothia) | LCDR1 | SQGISNW |
| SEQ ID NO: 300 (Chothia) | LCDR2 | GAS |
| SEQ ID NO: 301 (Chothia) | LCDR3 | YSSFPT |
| SEQ ID NO: 302 | VL | DIQMTQSPSSLSASVGDRVTITCRASQGISNWLAWYQ QKPGKAPKLLIYGASSLQSGVPSRFSGSGSGTDFTLT ISSLQPEDFATYYCQQYSSFPTTFGQGTKVEIK |

TABLE 1-continued

Examples of HER3 Antibodies useful in the methods of the Present Invention

| SEQ ID NUMBER | Ab region | |
|---|---|---|
| SEQ ID NO: 303 | VH | EVQLLESGGGLVQPGGSLRLSCAASGFTFSSYAMSWV RQAPGKGLEWVSVTGAVGGSTYYPDSVKGRFTISRDN SKNTLYLQMNSLRAEDTAVYYCARWGDEGFDIWGQGT LVTVSS |
| SEQ ID NO: 304 | DNA VL | GATATCCAGATGACCCAGAGCCCCAGCAGCCTGAGCG CCAGCGTGGGCGACAGAGTGACCATCACCTGTCGGGC CAGCCAGGGCATCAGCAACTGGCTGGCCTGGTATCAG CAGAAGCCCGGCAAGGCCCCCAAGCTGCTGATCTACG GCGCCAGCTCCCTGCAGAGCGGCGTGCCAAGCAGATT CAGCGGCAGCGGCTCCGGCACCGACTTCACCCTGACC ATCAGCAGCCTGCAGCCCGAGGACTTCGCCACCTACT ACTGCCAGCAGTACAGCAGCTTCCCCACCACCTTCGG CCAGGGCACCAAGGTGGAAATCAAG |
| SEQ ID NO: 305 | DNA VH | GAGGTGCAATTGCTGGAAAGCGGCGGAGGCCTGGTGC AGCCTGGCGGCAGCCTGAGACTGTCTTGCGCCGCCAG CGGCTTCACCTTCAGCAGCTACGCCATGAGCTGGGTC CGCCAGGCCCCTGGCAAGGGACTGGAATGGGTGTCCG TGACAGGCGCCGTGGGCGGAAGCACCTACTACCCCGA CAGCGTGAAGGGCCGGTTCACCATCAGCCGGGACAAC AGCAAGAACACCCTGTACCTGCAGATGAACAGCCTGC GGGCCGAGGACACCGCCGTGTACTACTGTGCCAGATG GGGCGACGAGGGCTTCGACATCTGGGGCCAGGGCACC CTGGTCACCGTCAGCTCA |
| SEQ ID NO: 306 | Light Kappa | DIQMTQSPSSLSASVGDRVTITCRASQGISNWLAWYQ QKPGKAPKLLIYGASSLQSGVPSRFSGSGSGTDFTLT ISSLQPEDFATYYCQQYSSFPTTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 307 | Heavy IgG1 | EVQLLESGGGLVQPGGSLRLSCAASGFTFSSYAMSWV RQAPGKGLEWVSVTGAVGGSTYYPDSVKGRFTISRDN SKNTLYLQMNSLRAEDTAVYYCARWGDEGFDIWGQGT LVTVSSASTKGPSVFPLAPSSKSTSGGTAALGCLVKD YFPEPVTVSWNSGALTSGVHTFPAVLQSSGLYSLSSV VTVPSSSLGTQTYICNVNHKPSNTKVDKRVEPKSCDK THTCPPCPAPELLGGPSVFLFPPKPKDTLMISRTPEV TCVVVDVSHEDPEVKFNWYVDGVEVHNAKTKPREEQY NSTYRVVSVLTVLHQDWLNGKEYKCKVSNKALPAPIE KTISKAKGQPREPQVYTLPPSREEMTKNQVSLTCLVK GFYPSDIAVEWESNGQPENNYKTTPPVLDSDGSFFLY SKLTVDKSRWQQGNVFSCSVMHEALHNHYTQKSLSLS PGK |
| MOR10701 R55K | | |
| SEQ ID NO: 308 (Kabat) | HCDR1 | SYAMS |
| SEQ ID NO: 309 (Kabat) | HCDR2 | VTGAVGKSTYYPDSVKG |
| SEQ ID NO: 310 (Kabat) | HCDR3 | WGDEGFDI |
| SEQ ID NO: 311 (Kabat) | LCDR1 | RASQGISNWLA |
| SEQ ID NO: 312 (Kabat) | LCDR2 | GASSLQS |
| SEQ ID NO: 313 (Kabat) | LCDR3 | QQYSSFPTT |
| SEQ ID NO: 314 (Chothia) | HCDR1 | GFTFSSY |
| SEQ ID NO: 315 (Chothia) | HCDR2 | GAVGKS |
| SEQ ID NO: 316 (Chothia) | HCDR3 | WGDEGFDI |
| SEQ ID NO: 317 (Chothia) | LCDR1 | SQGISNW |
| SEQ ID NO: 318 (Chothia) | LCDR2 | GAS |
| SEQ ID NO: 319 (Chothia) | LCDR3 | YSSFPT |
| SEQ ID NO: 320 | VL | DIQMTQSPSSLSASVGDRVTITCRASQGISNWLAWYQ QKPGKAPKLLIYGASSLQSGVPSRFSGSGSGTDFTLT ISSLQPEDFATYYCQQYSSFPTTFGQGTKVEIK |

TABLE 1-continued

Examples of HER3 Antibodies useful in the methods of the Present Invention

| SEQ ID NUMBER | Ab region | |
|---|---|---|
| SEQ ID NO: 321 | VH | EVQLLESGGGLVQPGGSLRLSCAASGFTFSSYAMSWV<br>RQAPGKGLEWVSVTGAVGKSTYYPDSVKGRFTISRDN<br>SKNTLYLQMNSLRAEDTAVYYCARWGDEGFDIWGQGT<br>LVTVSS |
| SEQ ID NO: 322 | DNA VL | GATATCCAGATGACCCAGAGCCCCAGCAGCCTGAGCG<br>CCAGCGTGGGCGACAGAGTGACCATCACCTGTCGGGC<br>CAGCCAGGGCATCAGCAACTGGCTGGCCTGGTATCAG<br>CAGAAGCCCGGCAAGGCCCCCAAGCTGCTGATCTACG<br>GCGCCAGCTCCCTGCAGAGCGGCGTGCCAAGCAGATT<br>CAGCGGCAGCGGCTCCGGCACCGACTTCACCCTGACC<br>ATCAGCAGCCTGCAGCCCGAGGACTTCGCCACCTACT<br>ACTGCCAGCAGTACAGCAGCTTCCCCACCACCTTCGG<br>CCAGGGCACCAAGGTGGAAATCAAG |
| SEQ ID NO: 323 | DNA VH | GAGGTGCAATTGCTGGAAAGCGGCGGAGGCCTGGTGC<br>AGCCTGGCGGCAGCCTGAGACTGTCTTGCGCCGCCAG<br>CGGCTTCACCTTCAGCAGCTACGCCATGAGCTGGGTC<br>CGCCAGGCCCCTGGCAAGGGACTGGAATGGGTGTCCG<br>TGACAGGCGCCGTGGGCAAAAGCACCTACTACCCCGA<br>CAGCGTGAAGGGCCGGTTCACCATCAGCCGGGACAAC<br>AGCAAGAACACCCTGTACCTGCAGATGAACAGCCTGC<br>GGGCCGAGGACACCGCCGTGTACTACTGTGCCAGATG<br>GGGCGACGAGGGCTTCGACATCTGGGGCCAGGGCACC<br>CTGGTCACCGTCAGCTCA |
| SEQ ID NO: 324 | Light Kappa | DIQMTQSPSSLSASVGDRVTITCRASQGISNWLAWYQ<br>QKPGKAPKLLIYGASSLQSGVPSRFSGSGSGTDFTLT<br>ISSLQPEDFATYYCQQYSSFPTTFGQGTKVEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC |
| SEQ ID NO: 325 | Heavy IgG1 | EVQLLESGGGLVQPGGSLRLSCAASGFTFSSYAMSWV<br>RQAPGKGLEWVSVTGAVGKSTYYPDSVKGRFTISRDN<br>SKNTLYLQMNSLRAEDTAVYYCARWGDEGFDIWGQGT<br>LVTVSSASTKGPSVFPLAPSSKSTSGGTAALGCLVKD<br>YFPEPVTVSWNSGALTSGVHTFPAVLQSSGLYSLSSV<br>VTVPSSSLGTQTYICNVNHKPSNTKVDKRVEPKSCDK<br>THTCPPCPAPELLGGPSVFLFPPKPKDTLMISRTPEV<br>TCVVVDVSHEDPEVKFNWYVDGVEVHNAKTKPREEQY<br>NSTYRVVSVLTVLHQDWLNGKEYKCKVSNKALPAPIE<br>KTISKAKGQPREPQVYTLPPSREEMTKNQVSLTCLVK<br>GFYPSDIAVEWESNGQPENNYKTTPPVLDSDGSFFLY<br>SKLTVDKSRWQQGNVFSCSVMHEALHNHYTQKSLSLS<br>PGK |
| MOR10701<br>deletion S56 | | |
| SEQ ID NO: 326 (Kabat) | HCDR1 | SYAMS |
| SEQ ID NO: 327 (Kabat) | HCDR2 | VTGAVGRTYYPDSVKG |
| SEQ ID NO: 328 (Kabat) | HCDR3 | WGDEGFDI |
| SEQ ID NO: 329 (Kabat) | LCDR1 | RASQGISNWLA |
| SEQ ID NO: 330 (Kabat) | LCDR2 | GASSLQS |
| SEQ ID NO: 331 (Kabat) | LCDR3 | QQYSSFPTT |
| SEQ ID NO: 332 (Chothia) | HCDR1 | GFTFSSY |
| SEQ ID NO: 333 (Chothia) | HCDR2 | GAVGRT |
| SEQ ID NO: 334 (Chothia) | HCDR3 | WGDEGFDI |
| SEQ ID NO: 335 (Chothia) | LCDR1 | SQGISNW |
| SEQ ID NO: 336 (Chothia) | LCDR2 | GAS |
| SEQ ID NO: 337 (Chothia) | LCDR3 | YSSFPT |
| SEQ ID NO: 338 | VL | DIQMTQSPSSLSASVGDRVTITCRASQGISNWLAWYQ<br>QKPGKAPKLLIYGASSLQSGVPSRFSGSGSGTDFTLT<br>ISSLQPEDFATYYCQQYSSFPTTFGQGTKVEIK |

TABLE 1-continued

Examples of HER3 Antibodies useful in the methods of the Present Invention

| SEQ ID NUMBER | Ab region | |
|---|---|---|
| SEQ ID NO: 339 | VH | EVQLLESGGGLVQPGGSLRLSCAASGFTFSSYAMSWV RQAPGKGLEWVSVTGAVGRTYYPDSVKGRFTISRDNS KNTLYLQMNSLRAEDTAVYYCARWGDEGFDIWGQGTL VTVSS |
| SEQ ID NO: 340 | DNA VL | GATATCCAGATGACCCAGAGCCCCAGCAGCCTGAGCG CCAGCGTGGGCGACAGAGTGACCATCACCTGTCGGGC CAGCCAGGGCATCAGCAACTGGCTGGCCTGGTATCAG CAGAAGCCCGGCAAGGCCCCCAAGCTGCTGATCTACG GCGCCAGCTCCCTGCAGAGCGGCGTGCCAAGCAGATT CAGCGGCAGCGGCTCCGGCACCGACTTCACCCTGACC ATCAGCAGCCTGCAGCCCGAGGACTTCGCCACCTACT ACTGCCAGCAGTACAGCAGCTTCCCCACCACCTTCGG CCAGGGCACCAAGGTGGAAATCAAG |
| SEQ ID NO: 341 | DNA VH | GAGGTGCAATTGCTGGAAAGCGGCGGAGGCCTGGTGC AGCCTGGCGGCAGCCTGAGACTGTCTTGCGCCGCCAG CGGCTTCACCTTCAGCAGCTACGCCATGAGCTGGGTC CGCCAGGCCCCTGGCAAGGGACTGGAATGGGTGTCCG TGACAGGCGCCGTGGGCAGAACCTACTACCCCGACAG CGTGAAGGGCCGGTTCACCATCAGCCGGGACAACAGC AAGAACACCCTGTACCTGCAGATGAACAGCCTGCGGG CCGAGGACACCGCCGTGTACTACTGTGCCAGATGGGG CGACGAGGGCTTCGACATCTGGGGCCAGGGCACCCTG GTCACCGTCAGCTCA |
| SEQ ID NO: 342 | Light Kappa | DIQMTQSPSSLSASVGDRVTITCRASQGISNWLAWYQ QKPGKAPKLLIYGASSLQSGVPSRFSGSGSGTDFTLT ISSLQPEDFATYYCQQYSSFPTTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 343 | Heavy IgG1 | EVQLLESGGGLVQPGGSLRLSCAASGFTFSSYAMSWV RQAPGKGLEWVSVTGAVGRTYYPDSVKGRFTISRDNS KNTLYLQMNSLRAEDTAVYYCARWGDEGFDIWGQGTL VTVSSASTKGPSVFPLAPSSKSTSGGTAALGCLVKDY FPEPVTVSWNSGALTSGVHTFPAVLQSSGLYSLSSVV TVPSSSLGTQTYICNVNHKPSNTKVDKRVEPKSCDKT HTCPPCPAPELLGGPSVFLFPPKPKDTLMISRTPEVT CVVVDVSHEDPEVKFNWYVDGVEVHNAKTKPREEQYN STYRVVSVLTVLHQDWLNGKEYKCKVSNKALPAPIEK TISKAKGQPREPQVYTLPPSREEMTKNQVSLTCLVKG FYPSDIAVEWESNGQPENNYKTTPPVLDSDGSFFLYS KLTVDKSRWQQGNVFSCSVMHEALHNHYTQKSLSLSP GK |
| MOR12609 | | |
| SEQ ID NO: 344 (Kabat) | HCDR1 | SYAMS |
| SEQ ID NO: 345 (Kabat) | HCDR2 | VINGLGYTTFYADSVKG |
| SEQ ID NO: 346 (Kabat) | HCDR3 | WGDEGFDI |
| SEQ ID NO: 347 (Kabat) | LCDR1 | RASQGISNWLA |
| SEQ ID NO: 348 (Kabat) | LCDR2 | GASSLQS |
| SEQ ID NO: 349 (Kabat) | LCDR3 | QQYSSFPTT |
| SEQ ID NO: 350 (Chothia) | HCDR1 | GFTFSSY |
| SEQ ID NO: 351 (Chothia) | HCDR2 | NGLGYT |
| SEQ ID NO: 352 (Chothia) | HCDR3 | WGDEGFDI |
| SEQ ID NO: 353 (Chothia) | LCDR1 | SQGISNW |
| SEQ ID NO: 354 (Chothia) | LCDR2 | GAS |
| SEQ ID NO: 355 (Chothia) | LCDR3 | YSSFPT |
| SEQ ID NO: 356 | VL | DIQMTQSPSSLSASVGDRVTITCRASQGISNWLAWYQ QKPGKAPKLLIYGASSLQSGVPSRFSGSGSGTDFTLT ISSLQPEDFAVYYCQQYSSFPTTFGQGTKVEIK |

TABLE 1-continued

Examples of HER3 Antibodies useful in the methods of the Present Invention

| SEQ ID NUMBER | Ab region | |
|---|---|---|
| SEQ ID NO: 357 | VH | QVQLVESGGGLVQPGGSLRLSCAASGFTFSSYAMSWV RQAPGKGLEWVSVINGLGYTTFYADSVKGRFTISRDN SKNTLYLQMNSLRAEDTAVYYCARWGDEGFDIWGQGT LVTVSS |
| SEQ ID NO: 358 | DNA VL | GATATCCAGATGACCCAGAGCCCGTCTAGCCTGAGCG CGAGCGTGGGTGATCGTGTGACCATTACCTGCAGAGC GAGCCAGGGTATTTCTAATTGGCTGGCTTGGTACCAG CAGAAACCAGGTAAAGCACCGAAACTATTAATTTATG GTGCTTCTTCTTTGCAAAGCGGGGTCCCGTCCCGTTT TAGCGGCTCTGGATCCGGCACTGATTTTACCCTGACC ATTAGCAGCCTGCAACCTGAAGACTTTGCGGTTTATT ATTGCCAGCAGTATTCTTCTTTTCCTACTACCTTTGG CCAGGGTACGAAAGTTGAAATTAAA |
| SEQ ID NO: 359 | DNA VH | CAGGTGCAATTGGTGGAAAGCGGCGGCGGCCTGGTGC AACCGGGCGGCAGCCTGCGTCTGAGCTGCGCGGCCTC CGGATTTACCTTTAGCAGCTATGCGATGAGCTGGGTG CGCCAAGCCCCTGGGAAGGGTCTCGAGTGGGTGAGCG TTATTAATGGTCTTGGTTATACTACTTTTTATGCTGA TTCTGTTAAGGGTCGTTTTACCATTTCACGTGATAAT TCGAAAAACACCCTGTATCTGCAAATGAACAGCCTGC GTGCGGAAGATACGGCCGTGTATTATTGCGCGCGTTG GGGTGATGAGGGTTTTGATATTTGGGGCCAAGGCACC CTGGTGACGGTTAGCTCA |
| SEQ ID NO: 360 | Light Kappa | DIQMTQSPSSLSASVGDRVTITCRASQGISNWLAWYQ QKPGKAPKLLIYGASSLQSGVPSRFSGSGSGTDFTLT ISSLQPEDFAVYYCQQYSSFPTTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 361 | Heavy IgG1 | QVQLVESGGGLVQPGGSLRLSCAASGFTFSSYAMSWV RQAPGKGLEWVSVINGLGYTTFYADSVKGRFTISRDN SKNTLYLQMNSLRAEDTAVYYCARWGDEGFDIWGQGT LVTVSSASTKGPSVFPLAPSSKSTSGGTAALGCLVKD YFPEPVTVSWNSGALTSGVHTFPAVLQSSGLYSLSSV VTVPSSSLGTQTYICNVNHKPSNTKVDKRVEPKSCDK THTCPPCPAPELLGGPSVFLFPPKPKDTLMISRTPEV TCVVVDVSHEDPEVKFNWYVDGVEVHNAKTKPREEQY NSTYRVVSVLTVLHQDWLNGKEYKCKVSNKALPAPIE KTISKAKGQPREPQVYTLPPSREEMTKNQVSLTCLVK GFYPSDIAVEWESNGQPENNYKTTPPVLDSDGSFFLY SKLTVDKSRWQQGNVFSCSVMHEALHNHYTQKSLSLS PGK |
| MOR12610 | | |
| SEQ ID NO: 362 (Kabat) | HCDR1 | SYAMS |
| SEQ ID NO: 363 (Kabat) | HCDR2 | GTGPYGGTYYPDSVKG |
| SEQ ID NO: 364 (Kabat) | HCDR3 | WGDEGFDI |
| SEQ ID NO: 365 (Kabat) | LCDR1 | RASQGISNWLA |
| SEQ ID NO: 366 (Kabat) | LCDR2 | GASSLQS |
| SEQ ID NO: 367 (Kabat) | LCDR3 | QQYSSFPTT |
| SEQ ID NO: 368 (Chothia) | HCDR1 | GFTFSSY |
| SEQ ID NO: 369 (Chothia) | HCDR2 | GPYGG |
| SEQ ID NO: 370 (Chothia) | HCDR3 | WGDEGFDI |
| SEQ ID NO: 371 (Chothia) | LCDR1 | SQGISNW |
| SEQ ID NO: 372 (Chothia) | LCDR2 | GAS |
| SEQ ID NO: 373 (Chothia) | LCDR3 | YSSFPT |
| SEQ ID NO: 374 | VL | DIQMTQSPSSLSASVGDRVTITCRASQGISNWLAWYQ QKPGKAPKLLIYGASSLQSGVPSRFSGSGSGTDFTLT ISSLQPEDFAVYYCQQYSSFPTTFGQGTKVEIK |

TABLE 1-continued

Examples of HER3 Antibodies useful in the methods of the Present Invention

| SEQ ID NUMBER | Ab region | |
|---|---|---|
| SEQ ID NO: 375 | VH | QVQLVESGGGLVQPGGSLRLSCAASGFTFSSYAMSWV RQAPGKGLEWVSGTGPYGGTYYPDSVKGRFTISRDNS KNTLYLQMNSLRAEDTAVYYCARWGDEGFDIWGQGTL VTVSS |
| SEQ ID NO: 376 | DNA VL | GATATCCAGATGACCCAGAGCCCGTCTAGCCTGAGCG CGAGCGTGGGTGATCGTGTGACCATTACCTGCAGAGC GAGCCAGGGTATTTCTAATTGGCTGGCTTGGTACCAG CAGAAACCAGGTAAAGCACCGAAACTATTAATTTATG GTGCTTCTTCTTTGCAAAGCGGGGTCCCGTCCCGTTT TAGCGGCTCTGGATCCGGCACTGATTTTACCCTGACC ATTAGCAGCCTGCAACCTGAAGACTTTGCGGTTTATT ATTGCCAGCAGTATTCTTCTTTTCCTACTACCTTTGG CCAGGGTACGAAAGTTGAAATTAAA |
| SEQ ID NO: 377 | DNA VH | CAGGTGCAATTGGTGGAAAGCGGCGGCGGCCTGGTGC AACCGGGCGGCAGCCTGCGTCTGAGCTGCGCGGCCTC CGGATTTACCTTTAGCAGCTATGCGATGAGCTGGGTG CGCCAAGCCCCTGGGAAGGGTCTCGAGTGGGTGAGCG GTACTGGTCCTTATGGTGGTACTTATTATCCTGATTC TGTTAAGGGTCGTTTTACCATTTCACGTGATAATTCG AAAAACACCCTGTATCTGCAAATGAACAGCCTGCGTG CGGAAGATACGGCCGTGTATTATTGCGCGCGTTGGGG TGATGAGGGTTTTGATATTTGGGGCCAAGGCACCCTG GTGACGGTTAGCTCA |
| SEQ ID NO: 378 | Light Kappa | DIQMTQSPSSLSASVGDRVTITCRASQGISNWLAWYQ QKPGKAPKLLIYGASSLQSGVPSRFSGSGSGTDFTLT ISSLQPEDFAVYYCQQYSSFPTTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 379 | Heavy IgG1 | QVQLVESGGGLVQPGGSLRLSCAASGFTFSSYAMSWV RQAPGKGLEWVSGTGPYGGTYYPDSVKGRFTISRDNS KNTLYLQMNSLRAEDTAVYYCARWGDEGFDIWGQGTL VTVSSASTKGPSVFPLAPSSKSTSGGTAALGCLVKDY FPEPVTVSWNSGALTSGVHTFPAVLQSSGLYSLSSVV TVPSSSLGTQTYICNVNHKPSNTKVDKRVEPKSCDKT HTCPPCPAPELLGGPSVFLFPPKPKDTLMISRTPEVT CVVVDVSHEDPEVKFNWYVDGVEVHNAKTKPREEQYN STYRVVSVLTVLHQDWLNGKEYKCKVSNKALPAPIEK TISKAKGQPREPQVYTLPPSREEMTKNQVSLTCLVKG FYPSDIAVEWESNGQPENNYKTTPPVLDSDGSFFLYS KLTVDKSRWQQGNVFSCSVMHEALHNHYTQKSLSLSP GK |

Other antibodies of the invention include those where the amino acids or nucleic acids encoding the amino acids have been mutated, yet have at least 60, 70, 80, 90, 95, 96, 97, 98, and 99 percent identity to the sequences described in Table 1. In some embodiments, it include mutant amino acid sequences wherein no more than 1, 2, 3, 4 or 5 amino acids have been mutated in the variable regions when compared with the variable regions depicted in the sequence described in Table 1, while retaining substantially the same therapeutic activity.

Since each of these antibodies or fragments thereof can bind to HER3, the VH, VL, full length light chain, and full length heavy chain sequences (amino acid sequences and the nucleotide sequences encoding the amino acid sequences) can be "mixed and matched" to create other HER3-binding antibodies of the invention. Such "mixed and matched" HER3-binding antibodies can be tested using the binding assays known in the art (e.g., ELISAs, and other assays described WO2012022814, which is incorporated herein in its entirety by reference. When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence. Accordingly, in one aspect, the invention provides an isolated monoclonal antibody or fragment thereof having: a heavy chain variable region comprising an amino acid sequence selected from the group consisting of SEQ ID NO: 15, 33, 51, 69, 87, 105, 123, 141, 159, 177, 195, 213, 231, 249, 267, 285, 303, 321, 339, 357, and 375; and a light chain variable region comprising an amino acid sequence selected from the group consisting of SEQ ID NOs: 14, 32, 50, 68, 86, 104, 122, 140, 158, 176, 194, 212, 230, 248, 266, 284, 302, 320, 338, 356, and 374; wherein the antibody specifically binds to HER3 (e.g., human and/or cynomologus).

In another aspect, the present invention provides HER3-binding antibodies that comprise the heavy chain and light chain CDR1s, CDR2s and CDR3s as described in Table 1, or combinations thereof. The amino acid sequences of the VH CDR1s of the antibodies are shown in SEQ ID NOs: 2, 8, 20, 26, 38, 44, 56, 62, 74, 80, 92, 98, 110, 116, 128, 134, 146, 152, 164, 170, 182, 188, 200, 206, 218, 224, 236, 242, 254, 260, 272, 278, 290, 296, 308, 314, 326, 332, 344, 350, 362, and 368. The amino acid sequences of the VH CDR2s of the antibodies and are shown in SEQ ID NOs: 3, 9, 21, 27, 39, 45, 57, 63, 75, 81, 93, 99, 111, 117, 129, 135, 147, 153, 165, 171, 183, 189, 201, 207, 219, 225, 237, 243, 255, 261, 273, 279, 291, 297, 309, 315, 327, 333, 345, 351, 363, and 369. The amino acid sequences of the VH CDR3s of the antibodies are shown in SEQ ID NOs: 4, 10, 22, 28, 40, 46, 58, 64, 76, 82, 94, 100, 112, 118, 130, 136, 148, 154, 166, 172, 184, 190, 202, 208, 220, 226, 238, 244, 256, 262, 274, 280, 292, 298, 310, 316, 328, 334, 346, 352, 364, and 370. The amino acid sequences of the VL CDR1s of the antibodies are shown in SEQ ID NOs: 5, 11, 23, 29, 41, 47, 59, 65, 77, 83, 95, 101, 113, 119, 131, 137, 149, 155, 167, 173, 185, 191, 203, 209, 221, 227, 239, 245, 257, 263, 275, 281, 293, 299, 311, 317, 329, 335, 347, 353, 365, and 371. The amino acid sequences of the VL CDR2s of the antibodies are shown in SEQ ID NOs: 6, 12, 24, 30, 42, 48, 60, 66, 78, 84, 96, 102, 114, 120, 132, 138, 150, 156, 168, 174, 186, 192, 204, 210, 222, 228, 240, 246, 258, 264, 276, 282, 294, 300, 312, 318, 330, 336, 348, 354, 366, and 372. The amino acid sequences of the VL CDR3s of the antibodies are shown in SEQ ID NOs: 7, 13, 25, 31, 43, 49, 61, 67, 79, 85, 97, 103, 115, 121, 133, 139, 151, 157, 169, 175, 187, 193, 205, 211, 223, 229, 241, 247, 259, 265, 277, 283, 295, 301, 313, 319, 331, 337, 349, 355, 367, and 373. The CDR regions are delineated using the Kabat system (Kabat et al., (1991) Sequences of Proteins of Immunological Interest, Fifth Edition, U.S. Department of Health and Human Services, NIH Publication No. 91-3242; Chothia et al., (1987) J. Mol. Biol. 196:901-917; Chothia et al., (1989) Nature 342: 877-883; and Al-Lazikani et al., (1997) J. Mol. Biol. 273, 927-948).

In a specific embodiment, an antibody that binds to HER3 comprises a heavy chain variable region CDR1 of SEQ ID NO: 2; a CDR2 of SEQ ID NO: 3; a CDR3 of SEQ ID NO: 4; a light chain variable region CDR1 of SEQ ID NO: 5; a CDR2 of SEQ ID NO: 6; and a CDR3 of SEQ ID NO: 7.

In a specific embodiment, an antibody that binds to HER3 comprises a heavy chain variable region CDR1 of SEQ ID NO: 20; a CDR2 of SEQ ID NO: 21; a CDR3 of SEQ ID NO: 22; a light chain variable region CDR1 of SEQ ID NO: 23; a CDR2 of SEQ ID NO: 24; and a CDR3 of SEQ ID NO: 25.

In a specific embodiment, an antibody that binds to HER3 comprises a heavy chain variable region CDR1 of SEQ ID NO: 38; a CDR2 of SEQ ID NO: 39; a CDR3 of SEQ ID NO: 40; a light chain variable region CDR1 of SEQ ID NO: 41; a CDR2 of SEQ ID NO: 42; and a CDR3 of SEQ ID NO: 43.

In a specific embodiment, an antibody that binds to HER3 comprises a heavy chain variable region CDR1 of SEQ ID NO: 56; a CDR2 of SEQ ID NO: 57; a CDR3 of SEQ ID NO: 58; a light chain variable region CDR1 of SEQ ID NO: 59; a CDR2 of SEQ ID NO: 60; and a CDR3 of SEQ ID NO: 61.

In a specific embodiment, an antibody that binds to HER3 comprises a heavy chain variable region CDR1 of SEQ ID NO: 74; a CDR2 of SEQ ID NO: 75; a CDR3 of SEQ ID NO: 76; a light chain variable region CDR1 of SEQ ID NO: 77; a CDR2 of SEQ ID NO: 78; and a CDR3 of SEQ ID NO: 79.

In a specific embodiment, an antibody that binds to HER3 comprises a heavy chain variable region CDR1 of SEQ ID NO: 92; a CDR2 of SEQ ID NO: 93; a CDR3 of SEQ ID NO: 94; a light chain variable region CDR1 of SEQ ID NO: 95; a CDR2 of SEQ ID NO: 96; and a CDR3 of SEQ ID NO: 97.

In a specific embodiment, an antibody that binds to HER3 comprises a heavy chain variable region CDR1 of SEQ ID NO: 110; a CDR2 of SEQ ID NO: 111; a CDR3 of SEQ ID NO: 112; a light chain variable region CDR1 of SEQ ID NO: 113; a CDR2 of SEQ ID NO: 114; and a CDR3 of SEQ ID NO: 115.

In a specific embodiment, an antibody that binds to HER3 comprises a heavy chain variable region CDR1 of SEQ ID NO: 128; a CDR2 of SEQ ID NO: 129; a CDR3 of SEQ ID NO: 130; a light chain variable region CDR1 of SEQ ID NO: 131; a CDR2 of SEQ ID NO: 132; and a CDR3 of SEQ ID NO: 133.

In a specific embodiment, an antibody that binds to HER3 comprises a heavy chain variable region CDR1 of SEQ ID NO: 146; a CDR2 of SEQ ID NO: 147; a CDR3 of SEQ ID NO: 148; a light chain variable region CDR1 of SEQ ID NO: 149; a CDR2 of SEQ ID NO: 150; and a CDR3 of SEQ ID NO: 151.

In a specific embodiment, an antibody that binds to HER3 comprises a heavy chain variable region CDR1 of SEQ ID NO: 164; a CDR2 of SEQ ID NO: 165; a CDR3 of SEQ ID NO: 166; a light chain variable region CDR1 of SEQ ID NO: 167; a CDR2 of SEQ ID NO: 168; and a CDR3 of SEQ ID NO: 169.

In a specific embodiment, an antibody that binds to HER3 comprises a heavy chain variable region CDR1 of SEQ ID NO: 182; a CDR2 of SEQ ID NO: 183; a CDR3 of SEQ ID NO: 184; a light chain variable region CDR1 of SEQ ID NO: 185; a CDR2 of SEQ ID NO: 186; and a CDR3 of SEQ ID NO: 187.

In a specific embodiment, an antibody that binds to HER3 comprises a heavy chain variable region CDR1 of SEQ ID NO: 200; a CDR2 of SEQ ID NO: 201; a CDR3 of SEQ ID NO: 202; a light chain variable region CDR1 of SEQ ID NO: 203; a CDR2 of SEQ ID NO: 204; and a CDR3 of SEQ ID NO: 205.

In a specific embodiment, an antibody that binds to HER3 comprises a heavy chain variable region CDR1 of SEQ ID NO: 218; a CDR2 of SEQ ID NO: 219; a CDR3 of SEQ ID NO: 220; a light chain variable region CDR1 of SEQ ID NO: 221; a CDR2 of SEQ ID NO: 222; and a CDR3 of SEQ ID NO: 223.

In a specific embodiment, an antibody that binds to HER3 comprises a heavy chain variable region CDR1 of SEQ ID NO: 236; a CDR2 of SEQ ID NO: 237; a CDR3 of SEQ ID NO: 238; a light chain variable region CDR1 of SEQ ID NO: 239; a CDR2 of SEQ ID NO: 240; and a CDR3 of SEQ ID NO: 241.

In a specific embodiment, an antibody that binds to HER3 comprises a heavy chain variable region CDR1 of SEQ ID NO: 254; a CDR2 of SEQ ID NO: 255; a CDR3 of SEQ ID NO: 256; a light chain variable region CDR1 of SEQ ID NO: 257; a CDR2 of SEQ ID NO: 258; and a CDR3 of SEQ ID NO: 259.

In a specific embodiment, an antibody that binds to HER3 comprises a heavy chain variable region CDR1 of SEQ ID NO: 272; a CDR2 of SEQ ID NO: 273; a CDR3 of SEQ ID NO: 274; a light chain variable region CDR1 of SEQ ID NO: 275; a CDR2 of SEQ ID NO: 276; and a CDR3 of SEQ ID NO: 277.

In a specific embodiment, an antibody that binds to HER3 comprises a heavy chain variable region CDR1 of SEQ ID NO: 290; a CDR2 of SEQ ID NO: 291; a CDR3 of SEQ ID NO: 292; a light chain variable region CDR1 of SEQ ID NO: 293; a CDR2 of SEQ ID NO: 294; and a CDR3 of SEQ ID NO: 295.

In a specific embodiment, an antibody that binds to HER3 comprises a heavy chain variable region CDR1 of SEQ ID NO: 308; a CDR2 of SEQ ID NO: 309; a CDR3 of SEQ ID NO: 310; a light chain variable region CDR1 of SEQ ID NO: 311; a CDR2 of SEQ ID NO: 312; and a CDR3 of SEQ ID NO: 313.

In a specific embodiment, an antibody that binds to HER3 comprises a heavy chain variable region CDR1 of SEQ ID NO: 326; a CDR2 of SEQ ID NO: 327; a CDR3 of SEQ ID NO: 328; a light chain variable region CDR1 of SEQ ID NO: 329; a CDR2 of SEQ ID NO: 330; and a CDR3 of SEQ ID NO: 331.

In a specific embodiment, an antibody that binds to HER3 comprises a heavy chain variable region CDR1 of SEQ ID NO: 344; a CDR2 of SEQ ID NO: 345; a CDR3 of SEQ ID NO: 346; a light chain variable region CDR1 of SEQ ID NO: 347; a CDR2 of SEQ ID NO: 348; and a CDR3 of SEQ ID NO: 349.

In a specific embodiment, an antibody that binds to HER3 comprises a heavy chain variable region CDR1 of SEQ ID NO: 362; a CDR2 of SEQ ID NO: 363; a CDR3 of SEQ ID NO: 364; a light chain variable region CDR1 of SEQ ID NO: 365; a CDR2 of SEQ ID NO: 366; and a CDR3 of SEQ ID NO: 367.

In a specific embodiment, an antibody that binds to HER3 comprises a VH of SEQ ID NO. 15 and VL of SEQ ID NO: 14. In a specific embodiment, an antibody that binds to HER3 comprises a VH of SEQ ID NO: 33 and VL of SEQ ID NO: 32. In a specific embodiment, an antibody that binds to HER3 comprises a VH of SEQ ID NO: 51 and VL of SEQ ID NO: 50. In a specific embodiment, an antibody that binds to HER3 comprises a SEQ ID NO: 69 and VL of SEQ ID NO: 68. In a specific embodiment, an antibody that binds to HER3 comprises a VH of SEQ ID NO: 87 and VL of SEQ ID NO: 86. In a specific embodiment, an antibody that binds to HER3 comprises a VH of SEQ ID NO: 105 and VL of SEQ ID NO: 104. In a specific embodiment, an antibody that binds to HER3 comprises a VH of SEQ ID NO: 123 and VL of SEQ ID NO: 122. In a specific embodiment, an antibody that binds to HER3 comprises a VH of SEQ ID NO: 141 and VL of SEQ ID NO: 140. In a specific embodiment, an antibody that binds to HER3 comprises a VH of SEQ ID NO: 159 and VL of SEQ ID NO: 158. In a specific embodiment, an antibody that binds to HER3 comprises a VH of SEQ ID NO: 177 and VL of SEQ ID NO: 176. In a specific embodiment, an antibody that binds to HER3 comprises a VH of SEQ ID NO: 195 and VL of SEQ ID NO: 194. In a specific embodiment, an antibody that binds to HER3 comprises a VH of SEQ ID NO: 213 and VL of SEQ ID NO: 212. In a specific embodiment, an antibody that binds to HER3 comprises a VH of SEQ ID NO: 231 and VL of SEQ ID NO: 230. In a specific embodiment, an antibody that binds to HER3 comprises a VH of SEQ ID NO: 249 and VL of SEQ ID NO: 248. In a specific embodiment, an antibody that binds to HER3 comprises a VH of SEQ ID NO: 267 and VL of SEQ ID NO: 266. In a specific embodiment, an antibody that binds to HER3 comprises a VH of SEQ ID NO: 285 and VL of SEQ ID NO: 284. In a specific embodiment, an antibody that binds to HER3 comprises a VH of SEQ ID NO: 303 and VL of SEQ ID NO: 302. In a specific embodiment, an antibody that binds to HER3 comprises a VH of SEQ ID NO: 321 and VL of SEQ ID NO: 320. In a specific embodiment, an antibody that binds to HER3 comprises a VH of SEQ ID NO: 339 and VL of SEQ ID NO: 338. In a specific embodiment, an antibody that binds to HER3 comprises a VH of SEQ ID NO: 357 and VL of SEQ ID NO: 356. In a specific embodiment, an antibody that binds to HER3 comprises a VH of SEQ ID NO: 375 and VL of SEQ ID NO: 374.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutations. However, in the VH or VL framework regions, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a recombinant human antibody will display no more than 10 amino acid differences from the amino acid sequence encoded by the human germline immunoglobulin gene in the VH or VL framework regions. In certain cases, the human antibody may display no more than 5, or even no more than 4, 3, 2, or 1 amino acid difference from the amino acid sequence encoded by the germline immunoglobulin gene. Different germlined versions using the VH and VL germline sequences for a representative number of HER3 antibodies is shown in WO2012022814, which is incorporated herein in its entirety by reference.

The antibodies disclosed herein can be derivatives of single chain antibodies, diabodies, domain antibodies, nanobodies, and unibodies. In yet another embodiment, the present invention provides an antibody or fragment thereof comprising amino acid sequences that are homologous to the sequences described in Table 1, and said antibody binds to a HER3 protein (e.g., human and/or cynomologus HER3), and retains the desired functional properties of those antibodies described in Table 1.

For example, the invention provides an isolated monoclonal antibody (or a functional fragment thereof) comprising a heavy chain variable region and a light chain variable region, wherein the heavy chain variable region comprises an amino acid sequence that is at least 80%, at least 90%, or at least 95% identical to an amino acid sequence selected from the group consisting of SEQ ID NOs: 15, 33, 51, 69, 87, 105, 123, 141, 159, 177, 195, 213, 231, 249, 267, 285, 303, 321, 339, 357, and 375; the light chain variable region comprises an amino acid sequence that is at least 80%, at least 90%, or at least 95% identical to an amino acid sequence selected from the group consisting of SEQ ID NOs: 14, 32, 50, 68, 86, 104, 122, 140, 158, 176, 194, 212, 230, 248, 266, 284, 302, 320, 338, 356, and 374; the antibody binds to HER3 (e.g., human and/or cynomologus HER3) and neutralizes the signaling activity of HER3, which can be measured in a phosphorylation assay or other measure of HER signaling (e.g., phospo-HER3 assays, phospho-Akt assays, cell proliferation, and ligand blocking assays as described in WO2012022814). Also includes within the scope of the invention are variable heavy and light chain parental nucleotide sequences; and full length heavy and light chain sequences optimized for expression in a mammalian cell. Other antibodies of the invention include amino acids or nucleic acids that have been mutated, yet have at least 60, 70, 80, 90, 95, or 98% percent identity to the sequences described above. In some embodiments, it include mutant amino acid sequences wherein no more than 1, 2, 3, 4 or 5 amino acids have been mutated by amino acid deletion, insertion or substitution in the variable regions when compared with the variable regions depicted in the sequence described above.

In other embodiments, the VH and/or VL amino acid sequences may be 50%, 60%, 70%, 80%, 90%, 95%, 96%, 97%, 98% or 99% identical to the sequences set forth in Table 1. In other embodiments, the VH and/or VL amino acid sequences may be identical except an amino acid substitution in no more than 1, 2, 3, 4 or 5 amino acid position. An antibody having VH and VL regions having high (i.e., 80% or greater) identity to the VH and VL regions of the antibodies described in Table 1 can be obtained by mutagenesis (e.g., site-directed or PCR-mediated mutagenesis), followed by testing of the encoded altered antibody for retained function using the functional assays described herein.

In other embodiments, the variable regions of heavy chain and/or light chain nucleotide sequences may be 60%, 70%, 80%, 90%, 95%, 96%, 97%, 98% or 99% identical to the sequences set forth above.

In certain embodiments, an antibody of the invention has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the HER3-binding antibodies of the invention.

Accordingly, the invention provides an isolated HER3 monoclonal antibody, or a fragment thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs: 2, 8, 20, 26, 38, 44, 56, 62, 74, 80, 92, 98, 110, 116, 128, 134, 146, 152, 164, 170, 182, 188, 200, 206, 218, 224, 236, 242, 254, 260, 272, 278, 290, 296, 308, 314, 326, 332, 344, 350, 362, and 368, and conservative modifications thereof; the heavy chain variable region CDR2 amino acid sequences are selected from the group consisting of SEQ ID NOs: 3, 9, 21, 27, 39, 45, 57, 63, 75, 81, 93, 99, 111, 117, 129, 135, 147, 153, 165, 171, 183, 189, 201, 207, 219, 225, 237, 243, 255, 261, 273, 279, 291, 297, 309, 315, 327, 333, 345, 351, 363, and 369 and conservative modifications thereof; the heavy chain variable region CDR3 amino acid sequences are selected from the group consisting of SEQ ID NOs: 4, 10, 22, 28, 40, 46, 58, 64, 76, 82, 94, 100, 112, 118, 130, 136, 148, 154, 166, 172, 184, 190, 202, 208, 220, 226, 238, 244, 256, 262, 274, 280, 292, 298, 310, 316, 328, 334, 346, 352, 364, and 370 and conservative modifications thereof; the light chain variable regions CDR1 amino acid sequences are selected from the group consisting of SEQ ID NOs: 5, 11, 23, 29, 41, 47, 59, 65, 77, 83, 95, 101, 113, 119, 131, 137, 149, 155, 167, 173, 185, 191, 203, 209, 221, 227, 239, 245, 257, 263, 275, 281, 293, 299, 311, 317, 329, 335, 347, 353, 365, and 371 and conservative modifications thereof; the light chain variable regions CDR2 amino acid sequences are selected from the group consisting of SEQ ID NOs: 6, 12, 24, 30, 42, 48, 60, 66, 78, 84, 96, 102, 114, 120, 132, 138, 150, 156, 168, 174, 186, 192, 204, 210, 222, 228, 240, 246, 258, 264, 276, 282, 294, 300, 312, 318, 330, 336, 348, 354, 366, and 372, and conservative modifications thereof; the light chain variable regions of CDR3 amino acid sequences are selected from the group consisting of SEQ ID NOs: 7, 13, 25, 31, 43, 49, 61, 67, 79, 85, 97, 103, 115, 121, 133, 139, 151, 157, 169, 175, 187, 193, 205, 211, 223, 229, 241, 247, 259, 265, 277, 283, 295, 301, 313, 319, 331, 337, 349, 355, 367, and 373, and conservative modifications thereof; the antibody or fragment thereof specifically binds to HER3, and neutralizes HER3 activity by inhibiting a HER signaling pathway, which can be measured in a phosphorylation assay or other measure of HER signaling (e.g., phospo-HER3 assays, phospho-Akt assays, cell proliferation, and ligand blocking assays as described in WO2012022814).

In another example, the isolated antibody or fragment thereof that cross-competes with an antibody described in Table 1. The antibodies can comprises a VH selected from the group consisting of SEQ ID NO: 15, SEQ ID NO: 33, SEQ ID NO: 51, SEQ ID NO: 69, SEQ ID NO: 87, SEQ ID NO: 105, SEQ ID NO: 123, SEQ ID NO: 141, SEQ ID NO: 159, SEQ ID NO: 177, SEQ ID NO: 195, SEQ ID NO: 213, SEQ ID NO: 231, SEQ ID NO: 249, SEQ ID NO: 267, SEQ ID NO: 285, SEQ ID NO: 303, SEQ ID NO: 321, SEQ ID NO: 339, SEQ ID NO: 357, and SEQ ID NO: 375; and a VL selected from the group consisting of SEQ ID NO: 14, SEQ ID NO: 32, SEQ ID NO: 50, SEQ ID NO: 68, SEQ ID NO: 86, SEQ ID NO: 104, SEQ ID NO: 122, SEQ ID NO: 140, SEQ ID NO: 158, SEQ ID NO: 176, SEQ ID NO: 194, SEQ ID NO: 212, SEQ ID NO: 230, SEQ ID NO: 248, SEQ ID NO: 266, SEQ ID NO: 284, SEQ ID NO: 302, SEQ ID NO: 320, SEQ ID NO: 338, SEQ ID NO: 356, and SEQ ID NO: 374 or an amino acid sequence with 97-99 percent identity thereof.

In another example, the isolated antibody or fragment thereof comprises a heavy chain variable region CDR1 selected from the group consisting of SEQ ID NO: 2, 20, 38, 56, 74, 92, 110, 128, 146, 164, 182, 200, 218, 236, 254, 272, 290, 308, 326, 344, and 362; CDR2 selected from the group consisting of SEQ ID NO: 3, 21, 39, 57, 75, 93, 111, 129, 147, 165, 183, 201, 219, 237, 255, 273, 291, 309, 327, 345, and 363; CDR3 selected from the group consisting of SEQ ID NO: 4, 22, 40, 58, 76, 94, 112, 130, 148, 166, 184, 202, 220, 238, 256, 274, 292, 310, 328, 346, and 364; a light chain variable region CDR1 selected from the group consisting of SEQ ID NO: 5, 23, 41, 59, 77, 95, 113, 131, 149, 167, 185, 203, 221, 239, 257, 275, 293, 311, 329, 347, and 365; CDR2 selected from the group consisting of SEQ ID NO: 6, 24, 42, 60, 78, 96, 114, 132, 150, 166, 186, 204, 222, 240, 258, 276, 294, 312, 330, 348, and 366; and CDR3 selected from the group consisting of SEQ ID NO: 7, 25, 43, 61, 79, 97, 115, 133, 151, 169, 187, 205, 223, 241, 259, 277, 295, 313, 331, 349, and 367.

In a specific example, the isolated antibody or fragment thereof, comprises a heavy chain variable region CDR1 of SEQ ID NO: 128; CDR2 of SEQ ID NO: 129; CDR3 of SEQ ID NO: 130; a light chain variable region CDR1 of SEQ ID NO: 131; CDR2 of SEQ ID NO: 132; and CDR3 of SEQ ID NO: 133.

The antibodies used in the invention can be fragment of an antibody that binds to HER3 selected from the group consisting of; Fab, F(ab$_2$)', F(ab)$_2$', scFv, VHH, VH, VL, dAbs.

The present invention also includes antibodies that interacts with (e.g., by binding, steric hindrance, stabilizing/destabilizing, spatial distribution) the same epitope as do the HER3-binding antibodies described in Table 1.

The present invention provides fully human antibodies that specifically bind to a HER3 protein (e.g., human and/or cynomolgus/mouse/rat HER3). Compared to the chimeric or humanized antibodies, the human HER3-binding antibodies of the invention have further reduced antigenicity when administered to human subjects.

The human HER3-binding antibodies can be generated using methods that are known in the art. For example, the humaneering technology used to converting non-human antibodies into engineered human antibodies. U.S. Patent Publication No. 20050008625 describes an in vivo method for replacing a nonhuman antibody variable region with a human variable region in an antibody while maintaining the same or providing better binding characteristics compared to that of the nonhuman antibody.

In another aspect, the present invention features biparatopic, bispecific or multispecific molecules comprising a HER3-binding antibody, or a fragment thereof, of the invention. An antibody of the invention, or fragments thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate biparatopic or multi-specific molecules that bind to more than two different binding sites and/or target molecules; such biparatopic or multi-specific molecules. To create a bispecific molecule of the invention, an antibody of the invention can be functionally linked (e.g., by chemical coupling, genetic fusion, non-covalent association or otherwise) to one or more other binding molecules, such as another antibody, antibody fragment, peptide or binding mimetic, such that a bispecific molecule results.

PI3K Inhibitors

PI3 kinase inhibitors can include, but are not limited to, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730), 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806), BKM120 and (5)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (also known as BYL719).

In one example, combinations of the present invention include a PI3K inhibitor selected from the group consisting of a compound of formula (I),

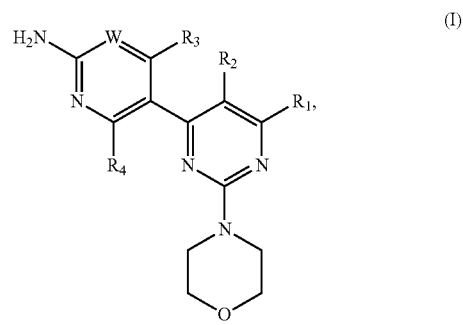

wherein
wherein W is $CR_w$ or N, wherein
$R_w$ is selected from the group consisting of:
(1) hydrogen,
(2) cyano,
(3) halogen,
(4) methyl,
5) trifluoromethyl,
(6) sulfonamide;
$R_1$ is selected from the group consisting of:
(1) hydrogen,
(2) cyano,
(3) nitro,
(4) halogen,
(5) substituted and unsubstituted alkyl,
(6) substituted and unsubstituted alkenyl,
(7) substituted and unsubstituted alkynyl,
(8) substituted and unsubstituted aryl,
(9) substituted and unsubstituted heteroaryl,
(10) substituted and unsubstituted heterocyclyl,
(11) substituted and unsubstituted cycloalkyl,
(12) —$COR_{1a}$,
(13) —$CO_2R_{1a}$,
(14) —$CONR_{1a}R_{1b}$,
(15) —$NR_{1a}R_{1b}$,
(16) —$NR_{1a}COR_{1b}$,
(17) —$NR_{1a}SO_2R_{1b}$,
(18) —$OCOR_{1a}$,
(19) —$OR_{1a}$,
(20) —$SR_{1a}$,
(21) —$SOR_{1a}$,
(23) —$SO_2NR_{1a}R_{1b}$ wherein
$R_{1a}$ and $R_{1b}$ are independently selected from the group consisting of:
(a) hydrogen,
(b) substituted or unsubstituted alkyl,
(c) substituted and unsubstituted aryl,
(d) substituted and unsubstituted heteroaryl,
(e) substituted and unsubstituted heterocyclyl, and
(f) substituted and unsubstituted cycloalkyl;
$R_2$ is selected from the group consisting of:
(1) hydrogen,
(2) cyano,
(3) nitro,
(4) halogen,
(5) hydroxy,
(6) amino,
(7) substituted and unsubstituted alkyl,
(8) —$COR_{2a}$, and
(9) —$NR_{2a}COR_{2b}$, wherein
$R_{2a}$ and $R_{2b}$ are independently selected from the group consisting of:
(a) hydrogen, and
(b) substituted or unsubstituted alkyl;

R₃ is selected from the group consisting of:
(1) hydrogen,
(2) cyano,
(3) nitro,
(4) halogen,
(5) substituted and unsubstituted alkyl,
(6) substituted and unsubstituted alkenyl,
(7) substituted and unsubstituted alkynyl,
(8) substituted and unsubstituted aryl,
(9) substituted and unsubstituted heteroaryl,
(10) substituted and unsubstituted heterocyclyl,
(11) substituted and unsubstituted cycloalkyl,
(12) —COR$_{3a}$,
(14) —NR$_{3a}$R$_{3b}$
(13) —NR$_{3a}$COR$_{3b}$,
(15) —NR$_{3a}$SO$_2$R$_{3b}$,
(16) —OR$_{3a}$,
(17) —SR$_{3a}$,
(18) —SOR$_{3a}$,
(19) —SO$_2$R$_{3a}$, wherein
R$_{3a}$, and R$_{3b}$ are independently selected from the group consisting of:
(a) hydrogen,
(b) substituted or unsubstituted alkyl,
(c) substituted and unsubstituted aryl,
(d) substituted and unsubstituted heteroaryl,
(e) substituted and unsubstituted heterocyclyl, and
(f) substituted and unsubstituted cycloalkyl; and
R₄ is selected from the group consisting of
(1) hydrogen, and
(2) halogen.
or a pharmaceutically acceptable salt thereof.

The radicals and symbols as used in the definition of a compound of formula (I) have meanings as disclosed in WO07/084786 which publication is hereby incorporated into the present application by reference in its entirety.

The PI3K inhibitor compound of formula (I) may be present in the combination in the form of the free base or a pharmaceutically acceptable salt thereof. Suitable salts of the compound of formula (I) include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemi-sulfate, heptanoate, hexanoate, fumarate, hydrochloride, hydrobromide, hydroiodide, 2 hydroxy-ethanesulfonate, lactate, maleate, methanesulfonate, nicotinate, 2 naphth-alenesulfonate, oxalate, pamoate, pectinate, persulfate, 3 phenylproionate, picrate, pivalate, propionate, succinate, sulfate, tartrate, thiocyanate, p toluenesulfonate, and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl, and stearyl chlorides, bromides and iodides, aralkyl halides like benzyl and phenethyl bromides, and others.

Suitable salts of the compound of formula (I) further include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine, pyridine, picoline, triethanolamine and the like, and basic amino acids such as arginine, lysine and ornithine.

A preferred compound of formula (I) for use in the combination of the present invention is the PI3K inhibitor 5-(2,6-di-morpholin-4-yl-pyrimidin-4-yl)-4-trifluorom-ethyl-pyridin-2-ylamine (also known as BKM120) or its hydrochloride salt. The synthesis of this compound is described in WO 2007/084786 as Example 10, the contents of which are incorporated herein by reference.

Use of the Combination and Administration

In accordance with the present invention, the combination of a HER3 antagonist and a PI3K inhibitor may be used for the treatment of a breast cancer brain metastases in a subject in need thereof by administering to the subject a pharmaceutical combination comprising (a) an effective amount of a phosphatidylinositol 3-kinase, e.g., selected from the group consisting of a compound of formula (I), and (b) an effective amount of a Her3 antagonist. Preferably, these therapeutic agents are administered at therapeutically effective dosages which, when combined, provide a jointly beneficial effect, e.g., synergistic or improved anti-proliferative effect, e.g., with regard to the delay of progression of breast cancer brain metastases or with regard to a change in tumor volume, as compared to either monotherapy. The administration may be separate, simultaneous or sequential. In one embodiment, the breast cancer is Her2 positive and has been determined to have one more PIK3CA mutations in exon 1, 2, 5, 7, 9 or 20 (e.g., in exon 9 E545K or exon 20 H1047R).

In one aspect, the present invention relates to a method for treating a breast cancer brain metastases comprising administering to subject in need thereof a combination of (a) a phosphatidylinositol 3-kinase selected from the group consisting of a compound of formula (I) or pharmaceutically acceptable salt thereof, and (b) a Her3 antibody or fragment thereof as described above in a quantity which is therapeutically effective against breast cancer brain metastases. In one embodiment, the breast cancer is Her2 positive. In another embodiment, the breast cancer is Her2 positive and has been determined to have one more PIK3CA mutations, e.g., in exon 1, 2, 5, 7, 9 or 20 (e.g., in exon 9 E545K or exon 20 H1047R).

In one aspect, the present invention relates to use of the combination of (a) a phosphatidylinositol 3-kinase selected from the group consisting of a compound of formula (I) or pharmaceutically acceptable salt thereof, and (b) a Her3 antibody or fragment thereof as described above for the preparation of a medicament for treating a breast cancer brain metastases. In one embodiment, the breast cancer is Her2 positive. In another embodiment, the breast cancer is Her2 positive and has been determined to have one more PIK3CA mutations, e.g., in exon 1, 2, 5, 7, 9 or 20 (e.g., in exon 9 E545K or exon 20 H1047R).

A patient having breast cancer brain metastases, may be separately, simultaneously or sequentially administered a combination comprising (a) a phosphatidylinositol 3-kinase inhibitor selected from the group consisting of a compound of formula (I) or pharmaceutically acceptable salt thereof, and (b) a Her3 antagonist as described herein for the treatment of said breast cancer brain metastases in accordance with the present invention.

The administration of a phosphatidylinositol 3-kinase inhibitor and a Her3 antagonist may result not only in a beneficial effect, e.g. therapeutic effect as compared to monotherapy of the individual therapeutic agents of the combination, e.g., a synergistic therapeutic effect, e.g. with regard to alleviating, delaying progression of or inhibiting the symptoms, but also in further surprising beneficial effects, e.g. fewer side-effects, an improved quality of life or a decreased morbidity, compared with a monotherapy applying only one of the pharmaceutically therapeutic agents used in the combination of the invention. In one embodiment, the progression of brain metastases is reduced.

A further benefit is that lower doses of the therapeutic agents of phosphatidylinositol 3-kinase inhibitor and a Her3 antagonist can be used, for example, that the dosages need not only often be smaller, but are also applied less frequently, or can be used in order to diminish the incidence of side-effects observed with one of the therapeutic agents alone. This is in accordance with the desires and requirements of the patients to be treated.

It can be shown by established test models that phosphatidylinositol 3-kinase inhibitor and a Her3 antagonist results in the beneficial effects described herein before. The person skilled in the art is fully enabled to select a relevant test model to prove such beneficial effects. The pharmacological activity of a phosphatidylinositol 3-kinase inhibitor and a Her3 antagonist may, for example, be demonstrated in a clinical study or in an in-vitro test procedure as essentially described hereinafter.

The optimal dosage of each therapeutic agent for treatment of breast cancer brain metastases can be determined empirically for each individual using known methods and will depend upon a variety of factors, including, though not limited to, the degree of advancement of the disease; the age, body weight, general health, gender and diet of the individual; the time and route of administration; and other medications the individual is taking. Optimal dosages may be established using routine testing and procedures that are well known in the art.

The amount of each therapeutic agent that may be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone.

Frequency of dosage may vary depending on the compound used and the particular condition to be treated. In general, the use of the minimum dosage that is sufficient to provide effective therapy is preferred. Patients may generally be monitored for therapeutic effectiveness using assays suitable for the condition being treated, which will be familiar to those of ordinary skill in the art.

The optimum ratios, individual and combined dosages, and concentrations of the drug compounds that yield efficacy without toxicity are based on the kinetics of the therapeutic agents' availability to target sites, and are determined using methods known to those of skill in the art.

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak (1996) Antibody Therapy, Bios Scientific Pub. Ltd, Oxfordshire, UK; Kresina (ed.) (1991) Monoclonal Antibodies, Cytokines and Arthritis, Marcel Dekker, New York, N.Y.; Bach (ed.) (1993) Monoclonal Antibodies and Peptide Therapy in Autoimmune Diseases, Marcel Dekker, New York, N.Y.; Baert et al., (2003) New Engl. J. Med. 348:601-608; Milgrom et al., (1999) New Engl. J. Med. 341:1966-1973; Slamon et al., (2001) New Engl. J. Med. 344:783-792; Beniaminovitz et al., (2000) New Engl. J. Med. 342:613-619; Ghosh et al., (2003) New Engl. J. Med. 348:24-32; Lipsky et al., (2000) New Engl. J. Med. 343:1594-1602).

Combinations comprising Her3 antibodies or fragments thereof of the invention can be provided separately or simultaneously with the PI3K inhibitor, and the compositions comprising the antibody can be provided by continuous infusion, or by doses at intervals of, e.g., one day, one week, or 1-7 times per week. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects. A total weekly dose may be at least 0.05 µg/kg body weight, at least 0.2 µg/kg, at least 0.5 µg/kg, at least 1 µg/kg, at least 10 µg/kg, at least 100 µg/kg, at least 0.2 mg/kg, at least 1.0 mg/kg, at least 2.0 mg/kg, at least 10 mg/kg, at least 25 mg/kg, or at least 50 mg/kg (see, e.g., Yang et al., (2003) New Engl. J. Med. 349:427-434; Herold et al., (2002) New Engl. J. Med. 346:1692-1698; Liu et al., (1999) J. Neurol. Neurosurg. Psych. 67:451-456; Portielji et al., (2003) Cancer Immunol. Immunother. 52:133-144). The desired dose of antibodies or fragments thereof is about the same as for an antibody or polypeptide, on a moles/kg body weight basis. The desired plasma concentration of the antibodies or fragments thereof is about, on a moles/kg body weight basis. The dose may be at least 15 µg at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, or at least 100 µg. The doses administered to a subject may number at least 1, 2, 3, 4, 5, 6, 7, 8, 9, 10, 11, or 12, or more.

For antibodies or fragments thereof the invention, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. In one example, doses may be delivered based on weight, e.g., 3 mg/kg, 10 mg/kg, 15 mg/kg, 20 mg/kg, 30 mg/kg, 40, mg/kg, 50 mg/kg, 60 mg/kg, 70 mg/kg, 80 mg/kg, 90 mg/kg, 100 mg/kg or as a fixed amount, e.g., 75 mg, 150 mg, 300 mg, 500 mg, 700 mg 1000 mg.

Unit dose of the antibodies or fragments thereof the invention may be 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 m g, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosage of the antibodies or fragments thereof the invention may achieve a serum titer of at least 0.1 µg/ml, at least 0.5 µg/ml, at least 1 µg/ml, at least 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml in a subject. Alternatively, the dosage of the antibodies or fragments thereof the invention may achieve a serum titer of at least 0.1 µg/ml, at least 0.5 µg/ml, at least 1 µg/ml, at least, 2 µg/ml, at least 5 µg/ml, at least 6 µg/ml, at least 10 µg/ml, at least 15 µg/ml, at least 20 .mu.g/ml, at least 25 µg/ml, at least 50 µg/ml, at least 100 µg/ml, at least 125 µg/ml, at least 150 µg/ml, at least 175 Kg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml in the subject.

Doses of antibodies or fragments thereof the invention may be repeated and the administrations may be separated by at least 1 day, 2 days, 3 days, 5 days, 7 days, 10 days, 15 days, 21 days, 30 days, 45 days, 2 months, 75 days, 3 months, or at least 6 months.

In one embodiment, the Her3 antagonist of the combination is administered every 5-14 days at a dosage of between 20 mg/ml-40 mg/ml. In one embodiment, the Her3 antagonist MOR10703 of the combination is administered every 7 days at a dosage of 20 mg/ml. In one embodiment, the Her3 antagonist MOR10703 of the combination is administered every 7 days at a dosage of 20 mg/ml+/−10 mg/ml. In one embodiment, the Her3 antagonist MOR10703 of the combination is administered every 14 days at a dosage of 20 mg/ml+/−10 mg/ml. In one embodiment, the Her3 antagonist MOR10703 of the combination is administered every 21 days at a dosage of 20 mg/ml+/−10 mg/ml.

The PI3K inhibitor of the combination is preferably administered daily at a dose in the range of from about 0.001 to 1000 mg/kg body weight daily and more preferred from 1.0 to 30 mg/kg body weight. In one embodiment, the dosage compound of formula I, is in the range of about 10 mg to about 2000 mg per person per day. In one example, 1.0 to 30 mg/kg body weight. In one preferred embodiment, the dosage of compound of formula (I) is in the range of about 60 mg/day to about 120 mg/day, especially if the warm-blooded animal is an adult human. Preferably, the dosage of compound of formula (I) is in the range of about 60 mg/day to about 100 mg/day for an adult human. The Compound of formula (I) may be administered orally to an adult human once daily continuously (each day) or intermittently (e.g, 5 out of 7 days) in a suitable dosage. For example, the phosphatidylinositol 3-kinase inhibitor of 5-(2,6-di-morpholin-4-yl-pyrimidin-4-yl)-4-trifluoromethyl-pyridin-2-ylamine or its hydrochloride salt is administered between 60 mg/day to about 120 mg/day, e.g., 100 mg·ml and the dosage of MOR10703 is administered every 5-14 days at a dosage of between 20 mg/ml-40 mg/ml. In another example, the phosphatidylinositol 3-kinase inhibitor of 5-(2,6-di-morpholin-4-yl-pyrimidin-4-yl)-4-trifluoromethyl-pyridin-2-ylamine or its hydrochloride salt is administered between 60 mg/day to about 120 mg/day, e.g., 100 mg·ml and the dosage of MOR10703 is administered every 14-30 days, e.g., 21-28 days at a dosage of between 20 mg/ml-40 mg/ml. In another example, the phosphatidylinositol 3-kinase inhibitor of 5-(2, 6-di-morpholin-4-yl-pyrimidin-4-yl)-4-trifluoromethyl-pyridin-2-ylamine or its hydrochloride salt is administered between 60 mg/day to about 120 mg/day, e.g., 100 mg·ml and the dosage of MOR10703 is administered every 7-28 days, e.g., every 21 days at a dosage of between 20 mg/ml-40 mg/ml.

An effective amount for a particular patient may vary depending on factors such as the condition being treated, the overall health of the patient, the method route and dose of administration and the severity of side affects (see, e.g., Maynard et al., (1996) A Handbook of SOPs for Good Clinical Practice, Interpharm Press, Boca Raton, Fla.; Dent (2001) Good Laboratory and Good Clinical Practice, Urch Publ., London, UK).

The route of administration of the PI3K and/or the Her3 antagonist of the combination may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al., (1983) Biopolymers 22:547-556; Langer et al., (1981) J. Biomed. Mater. Res. 15:167-277; Langer (1982) Chem. Tech. 12:98-105; Epstein et al., (1985) Proc. Natl. Acad. Sci. USA 82:3688-3692; Hwang et al., (1980) Proc. Natl. Acad. Sci. USA 77:4030-4034; U.S. Pat. Nos. 6,350,466 and 6,316,024). Where necessary, the composition may also include a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985, 320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

A composition of the present invention may also be administered via one or more routes of administration using one or more of a variety of methods known in the art. Parenteral routes of administration may be used for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the invention can be administered via a non-parenteral route, such as a topical, epidermal or mucosal route of administration, for example, intranasally, orally, vaginally, rectally, sublingually or topically.

Methods for co-administration or treatment with a PI3Kinase inhibitor such as a compound of formula (I) are known in the art (see, e.g., Hardman et al., (eds.) (2001) Goodman and Gilman's The Pharmacological Basis of Therapeutics, 10.sup.th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.).

PI3K inhibitors can be administered in combination with the antibodies or fragments thereof described herein and may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the antibodies or fragments thereof the invention. The two or more therapies may be administered within one same patient visit.

The HER3 antagonists and the PI3K inhibitors may be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the antibodies or fragments thereof the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade, (1989) J. Clin. Pharmacol. 29:685). Exemplary targeting moieties include folate or biotin (see, e.g., U.S. Pat. No. 5,416,016 to Low et al); mannosides (Umezawa et al., (1988) Biochem. Biophys. Res. Commun. 153:1038); antibodies (Bloeman et al., (1995) FEBS Left. 357:140; Owais et al., (1995) Antimicrob. Agents Chemother. 39:180); surfactant protein A receptor (Briscoe et al., (1995) Am. J. Physiol. 1233:134); p 120 (Schreier et al, (1994) J. Biol. Chem. 269:9090); see also K. Keinanen; M. L. Laukkanen (1994) FEBS Left. 346:123; J. J. Killion; I. J. Fidler (1994) Immunomethods 4:273.

The invention provides for the administration of HER3 antagonists in combination with a PI3K inhibitor. The therapies of the combination therapies of the present invention can be administered concomitantly or sequentially to a subject. The therapy of the combination therapies of the present invention can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The combination therapies of HER3 antagonists with PI3K inhibitors can be administered to a subject concurrently. The term "concurrently" is not limited to the administration of therapies (e.g., prophylactic or therapeutic agents) at exactly the same time, but rather it is meant that a pharmaceutical composition comprising antibodies or fragments thereof the invention are administered to a subject in a sequence and within a time interval such that the antibodies of the invention can act together with the PI3K inhibitors to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The combination therapies can be administered to a subject in the same pharmaceutical composition. Alternatively, the combination therapies can be administered concurrently to a subject in separate pharmaceutical compositions. The therapeutic agents may be administered to a subject by the same or different routes of administration.

The invention having been fully described, it is further illustrated by the following examples and claims, which are illustrative and are not meant to be further limiting.

EXAMPLES

Example 1: Example 1: Differential Response of HER2-Positive Breast Cancer to PI3K Inhibition when Growing in the MFP or Brain 5-(2,6-di-morpholin-4-yl-pyrimidin-4-yl)-4-trifluoromethyl-pyridin-2-ylamine (referred to herein as "COMPOUND A") is a potent and specific pan-Class I PI3K inhibitor with activity against breast cancer cells bearing HER2-amplification as well as oncogenic PI3K catalytic subunit alpha (PIK3CA) mutations. We compared the efficacy of COMPOUND A on identical human HER2-positive breast cancer cells growing in the MFP or in the brain parenchyma of nude mice. The three breast cancer cell lines examined included HER2-amplified BT474, HER2-amplified and PIK3CA mutant (E545K) MDA-MB-361, and PIK3CA mutant (H1047R) T-47D cell lines. While COMPOUND A led to regression of HER2- or PI3K-driven breast tumors growing in the MFP, established brain metastatic lesions were resistant to treatment (FIGS. 1A and 1B). Tumor tissue collected two hours after the final dose of COMPOUND A showed a comparable level of p-AKT inhibition in BM compared with MFP tumors. In addition to the level of inhibition, we observed a similar time course of p-AKT inhibition after short-term COMPOUND A treatment in BM or MFP tumors. Furthermore, the concentration of COMPOUND A in breast tumors growing at both sites, as well as in the plasma of these mice was identical. Taken together, these data show that the dramatic difference in growth sensitivity to PI3K inhibition is not simply due to a compromised pharmacokinetic/pharmacodynamic profile of COMPOUND A in brain tumors.

Example 2: HER2-Positive Breast Cancer Cells Require Constant Influence from the Brain Microenvironment for Resistance We began our investigation into the resistance of breast cancer BM to PI3K inhibition by asking if breast cancer cells require constant influence from the brain microenvironment. We isolated breast cancer cells after dissociation of a brain metastatic tumor (termed BT474-Gluc-BR). After cultured for a week in vitro, the vast majority of viable cells were cancer cells, as identified by GFP. These "brain microenvironment-exposed" breast cancer cells were similarly sensitive to COMPOUND A in vitro as parental cells. This data suggests that the brain microenvironment does not induce a permanent change to breast cancer cells, nor is there preferential growth of COMPOUND A-resistant clones in the brain. Instead, breast cancer cells must receive continuous support from the brain microenvironment in order to maintain resistance.

Example 3: MFP and Brain Tumors have an Equivalent Growth Rate

We first hypothesized the brain microenvironment induces breast cancer cells to be more proliferative, thus reducing the ability to slow their growth with targeted agents. While it takes fewer breast cancer cells to form a tumor in the brain parenchyma compared with the MFP, once a tumor is established the growth rate of cancer cells within the two microenvironments is identical.

Example 4: ErbB Family Members are Hyperphosphorylated and Overexpressed in Breast Tumors Growing in the Brain Parenchyma Compared to the MFP, and in Human Brain Metastases We hypothesized secreted factors from the host brain parenchyma could activate receptors on the surface of cancer cells to mediate resistance to PI3K inhibition. Therefore, we performed a phospho-receptor protein array to investigate the difference in phosphorylation status of a number of growth factor receptors between MFP and brain tumors. The array displayed clear hyperactivation of the ErbB family members EGFR and HER3 in BT474-Gluc brain tumors. Western blotting confirmed increased phosphorylated and total HER3 in both BT474-Gluc and T-47D-Gluc brain tumors, compared with their MFP counterparts. While BT474-Gluc brain tumors display increased phosphorylated and total EGFR, T-47D-Gluc brain tumors show much less compared to MFP tumors. MDA-MB-361-Gluc brain tumors show increased total EGFR, but undetectable levels of phosphorylated protein, as well as a slight increase in total, but not phosphorylated, HER3. Our findings led us to focus on HER3 as the regulator of resistance in our breast cancer BM model. Consistent with an increase in HER3 protein, human HER3 mRNA expression is higher in BT474-Gluc tumors growing in the brain. Finally, immunohistochemical analysis of matched human primary breast cancer and BM depicted increased HER3 protein in 63% (5 of 8) of brain metastatic lesions compare to 13% (1 of 8) of primary cancer.

Example 5: Neuregulins Induce Resistance of Breast Cancer Cells to PI3K Inhibition and are More Expressed in the Murine Brain Compared with MFP In an unbiased analysis of 220 growth factors, NRG-1 and -2 were the most potent inducers of resistance to COMPOUND A in the three HER2-positive breast cancer cell lines tested.

Since HER3 is the major receptor for NRG, we hypothesized NRG is signaling through HER3 to induce resistance. Therefore, we tested the ability of HER3 inhibition to overcome NRG-induced PI3K or HER2 inhibition in vitro. To target HER3 we employed MOR10375 an antibody that induces a conformational change and locks HER3 in an inactive state. NRG1-induced breast cancer PI3K inhibitor resistance was overcome through the addition of MOR10703. These data show that the NRG-HER3 axis, hyperactivated in COMPOUND A-resistant breast cancer BM, drive resistance of breast cancer cells to PI3K inhibition in vitro. Together, these findings suggest that NRG, constitutively produced by the brain microenvironment, induces HER2-positive breast cancer brain metastatic resistance to PI3K inhibition through HER3 activation.

Figure 2:
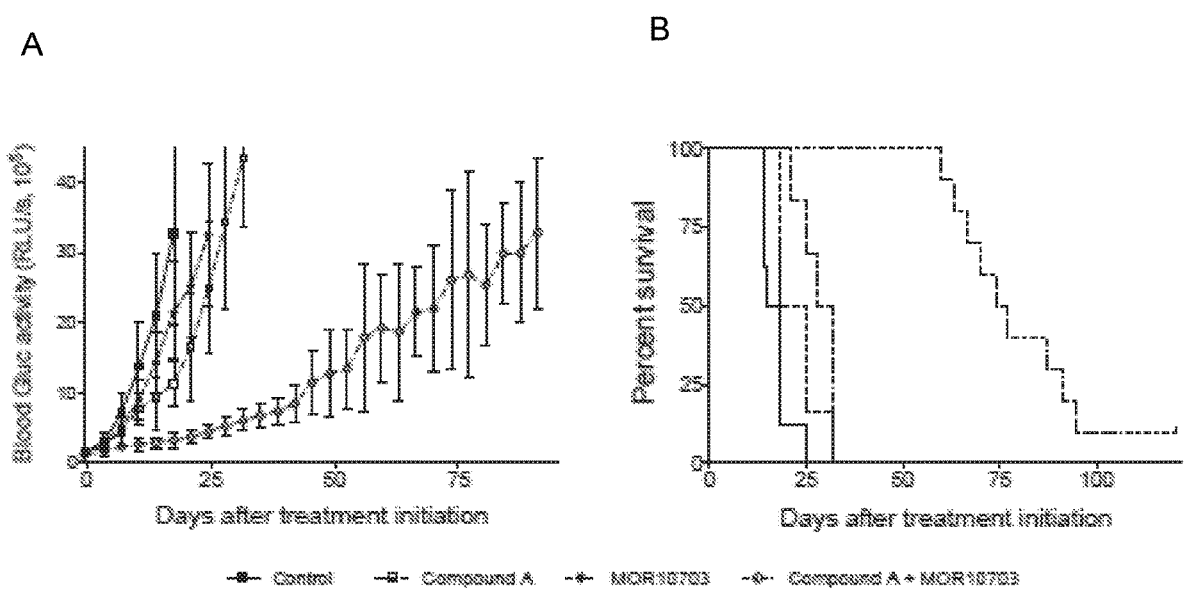
FIG. 2 shows a tumor growth curve (2A) and survival analysis (2B) of BT474-Gluc brain tumors untreated or treated with COMPOUND A, MOR10703, or COMPOUND A and MOR10703.
Figure 3:
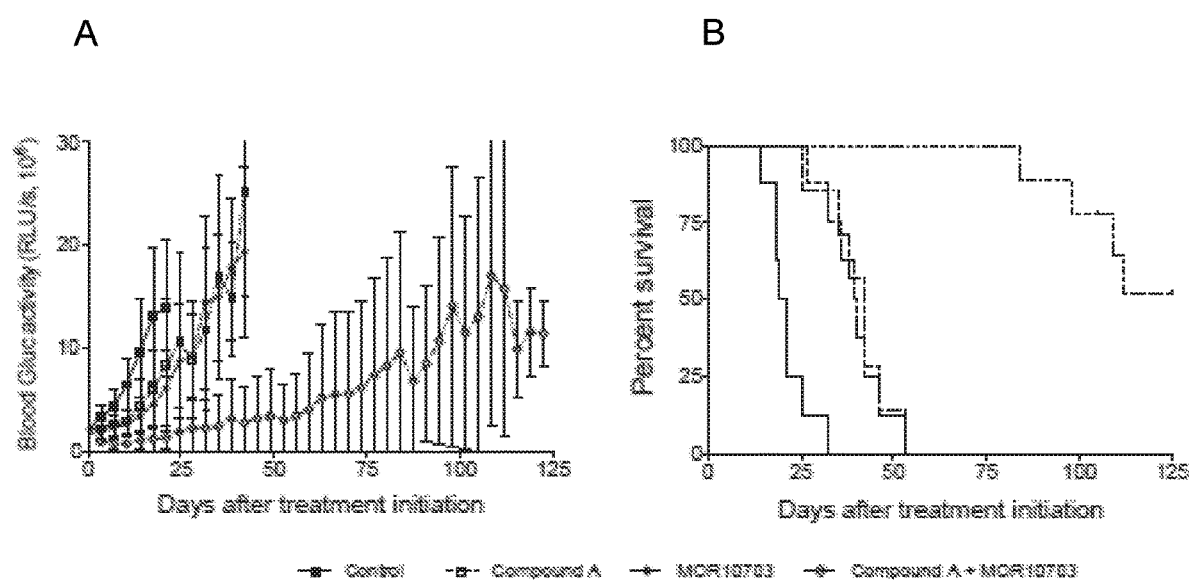
FIG. 3 shows a tumor growth curve (3A) and survival analysis (3B) of MDA-MB-361-Gluc brain tumors untreated or treated with COMPOUND A, MOR10703, or COMPOUND A and MOR10703.

Example 6: HER3 Inhibition Overcomes the Brain Microenvironment-Mediated Resistance of Breast Tumors to PI3K or HER2 Inhibition We tested the ability of the HER3 inhibitor MOR10703 alone or in combination with COMPOUND A, to slow the growth of BT474-Gluc brain tumors BM (FIG. 2A-B). MOR10703 monotherapy did not significantly slow the growth of breast cancer in the brain parenchyma. However, the combination of HER3 inhibition with COMPOUND A significantly slowed the growth of breast cancer BM. The tumor growth delay with the combination therapies led to a 2.5 or 2-fold increase in survival, compared with the COMPOUND A monotherapy group, in BT474-Gluc or MDA-MB-361-Gluc brain tumors, respectively (3A-B).

Conclusion:

Our findings show that a pathway known to mediate resistance of extracranial HER2-positive disease is hyperactivated a priori in the brain microenvironment, and leads to de novo resistance. Until this report, there is to date no published data on a possible role of NRG-1 in breast cancer brain metastases. While NRG-1 has been described as a mediator of PI3K-inhibitor resistance in breast cancer cells growing in vitro, we describe its role within an organ in vivo where expression levels are naturally occurring. We reveal translational evidence for NRG-1 in promoting therapy resistance of breast cancer BM, and, furthermore, propose treatment options to overcome NRG-1 activity and improve the therapeutic efficacy in the brain microenvironment by using a Her3 antagonist such as described herein. The treatments of the invention can now be used to metastatic breast cancer in the brain.

Example 7: Methods Summary

Cell Lines, Infections, and Culture.

BT474, MDA-MB-361, and T-47D cells were transduced with an expression cassette encoding Gluc and GFP separated by an internal ribosomal entry site, using a lentiviral vector. GFP-positive cells were sorted with a FACSAria cell sorter (BD Biosciences). BT474-Gluc and T-47D-Gluc cells were maintained in RPMI 1640 supplemented with 10% (vol/vol) FBS (Atlanta Biologics). MDA-MB-361-Gluc were maintained in DMEM/F12 supplemented with 10% (vol/vol) FBS.

Mammary Fat Pad and Brain Metastatic Xenografts.

Female nude mice (8-9 wk of age) were ovariectomized and implanted with a 0.36-mg or 0.72-mg 17β-estradiol pellet (Innovative Research of America) the day before implantation of tumor cells. Pellets were replaced at expiration date, either 60 or 90 days. For the mammary fat pad model, $5 \times 10^6$ BT474-Gluc cells were suspended in a 50-μL mixture of PBS and Matrigel Matrix High Concentration (BD Biosciences) at a 1:1 ratio before injection. For injection into the brain, the head of the mouse was fixed with a stereotactic apparatus and the skull over the left hemisphere of the brain was exposed via skin incision. Using a high-speed air-turbine drill (CH4201S; Champion Dental Products) with a burr tip size of 0.5 mm in diameter, three sides of a square (~2.5 mm in length, each side) were drilled through the skull until a bone flap became loose. Using blunt tweezers, the bone flap was pulled back, exposing the brain parenchyma. 100,000 cancer cells, diluted in 1 μL PBS, were stereotactically injected into the left frontal lobe of the mice. The bone flap was then placed back into position in the skull and sealed using histocompatible cyanoacrylate gluc, and the skin atop the skull was sutured closed. All animal procedures were performed according to the guidelines of the Public Health Service Policy on Human Care of Laboratory Animals and in accordance with a protocol approved by the Institutional Animal Care and Use Committee of Massachusetts General Hospital.

Cranial Window, Ultrasound Imaging, and Tumor Volume Calculation.

Cranial windows were implanted into nude mice. To assess tumor volume, in vivo imaging was performed through a cranial window using a small animal ultrasonography device (Vevo 2100, FujiFilm VisualSonics Inc.).

Tumor Size Monitoring and Survival Analysis.

Tumor size was measured twice a week by measuring the activity of secreted Gluc in the blood. Measurement of blood Gluc was performed as described previously[53]. Briefly, blood was drawn from a slight nick in a tail vein of the mouse. 13 μL of blood was collected and mixed with 3 μL of 50 mM EDTA, and was then stored at −80° C. Blood was transferred to an opaque 96-well plate, and Gluc activity was measured using coelenterazine (CTZ; Nanolight) as a substrate and a plate luminometer (Centro XS LB960; Berthold Technologies). The luminometer was set to inject 100 μL of 50 μg/mL CTZ in PBS automatically, and photon counts were acquired for 1 s. For survival analysis, mice were euthanized when they lost more than 20% body weight or exhibited signs of prolonged distress or neurological impairment.

Reagents and Treatments.

COMPOUND A was administered at either 30 or 50 mg/kg once a day via oral gavage (p.o.). MOR10703 was administered at 25 mg/kg every two days via intraperitoneal injection (i.p.). Both COMPOUND A and MOR10703 were obtained from Novartis. Trastuzumab (Genentech) and pertuzumab (Genetech) were administered at 15 mg/kg once a week via i.p. Both trastuzumab and pertuzumab were obtained from the Massachusetts General Hospital pharmacy. Neratinib was administered at 20 mg/kg once a day via p.o., and purchased from LC laboratories. Recombinant NRG113 was obtained from R&D Systems.

Compound A Concentration Measurement.

Tumor samples were collected, weighed and lysed in Lysing Matrix D tube (MP Biomedicals) in RIPA buffer (Cell Signaling Technologies (CST)) at fixed weight/volume ratio. The samples were centrifuged at 13,000 rpm and 4° C. in Micro centrifuge for 10 min. Supernatant was collected from the lysate and stored at −80° C. The COMPOUND A concentration in tumor lysate was analyzed by LC-MS/MS at Inventiv Health Clinical Lab, Inc. It was then normalized by tumor weight-lysis buffer ratio to yield COMPOUND A exposure (ng/mL) in tumor tissue.

Isolation of Cancer Cells from Brain Metastatic Tumor Tissue.

Tumor tissue was minced with scissors and a scalpel in RPMI media, and incubated in RPMI+10% FBS+1% penicillin/streptomycin (P/S) with 1 mg/mL collagenase/dispase enzyme mix (Roche) at 37° C., shaking for 1 h. Tissue was then centrifuged at 1500 rpm for 5 m, and supernatant removed. Tissue was resuspended in RPMI+10% FBS+1% P/S, and pipetted well to dissociate clumps. Further, the mixture was pipetted through a 70 m filter before plating. Media was refreshed the following day.

Quantitative Real Time-Polymerase Chain Reaction.

RNA was extracted using the RNEasy Mini Kit (Qiagen), using the manufacturer's protocol with optional on-column DNA digestion. cDNA was synthesized by employing the iScript Supermix RT system (BioRad). RT-PCR reactions were performed with the following primers: HER3, forward GCCAAGGGCCCAATCTACAA (SEQ ID NO: 380) and reverse TGTCAGATGGGTTTTGCCGA (SEQ ID NO: 381); HER2 forward AGCCGCGAGCACCCAAGT (SEQ ID NO: 382) and reverse TTGGTGGGCAGGTAGGT-GAGTT (SEQ ID NO: 383); GFAP forward GAGA-GAAAGGTTGAATCGCTGGA (SEQ ID NO: 384) and reverse CGGGACGCAGCGTCTGTG (SEQ ID NO: 385); Iba1 forward GTCCTTGAAGCGAATGCTGG (SEQ ID NO: 386) and reverse CATTCTCAAGATGGCAGATC (SEQ ID NO: 387); Actin forward AGAAAATCTGGCAC-CACACC (SEQ ID NO: 388) and reverse CTCCTTAAT-GTCACGCACG (SEQ ID NO: 389); NRG-1 forward GGT-GATCGCTGCCAAAACTA (SEQ ID NO: 390) and reverse GAGTGATGGGCTGTGGAAGT (SEQ ID NO: 391); NRG-2 forward GGTAATCCCCAGCCTTCCTA (SEQ ID NO: 392) and reverse GGTTGATGCCCTCGATGTAG (SEQ ID NO: 393).

Resistance Analysis of Secreted Growth Factors.

A collection of cDNA constructs representing secreted and single pass transmembrane proteins was identified (as described previously described[56]) and purchased from Invitrogen Ultimate ORF collection. (The library is maintained by DMP BioArchive.) pCDNA-DEST40 (Invitrogen) was the plasmid vector for all clones, and all clone inserts were confirmed by full sequencing. For this study a collection of 338 cDNA constructs, representing 220 unique secreted and single pass transmembrane proteins, was used to identify rescued ligands in the present of each compound treatment—each cDNA construct was reverse-transfected using HEK293T/17. After 3 days of incubation, secreted proteins were then transferred to studied cell lines followed with the addition of compounds for 96 h incubation. CellTiter-Glo assay was then used for conducting end-point read out.

Following plate to plate normalization of the raw CTG reading for triplicates, the rescue % value for each secreted protein was calculated using the following formula: Rescue %=[Median (drug+supe)−Median (drug)]/[Median (DMSO)−Median (drug)]. The statistical probability score of the Rescue % value was also calculated: p-value=Chidist [Z(drug+supe)$^2$, 1], where Z(drug+supe)=[Median (drug+supe)−Median (drug)]/Std(drug+supe), where drug+supe stands for the individual sample that were treated with individual supernatant that was expected to contain one unique secreted protein. Data points were then plotted using SpotFire software. Secreted proteins that had a rescue of ≥20% with P-value≤0.05 were labeled in each scatter plot.

In Vitro Cell Growth Assays.

The xCELLigence system (Acea Biosciences Inc.) was used to assess the cell index of T-47D, BT474 and MDA-MB-361 cells. xCELLigence measures electrical impedance across micro-electrodes integrated at the bottom of tissue culture E-plates to provide quantitative information about the biological status of cells, including cell number, morphology and viability. One day before drug addition, cells were seeded in 96-well E-plates at a density of 6000-10000 cells per well in 90 μl growth media. Cells were monitored every 15 m for a period of up to 24 h via the incorporated sensor electrode arrays of the E-Plate 96. After 24 h incubation E-plates were removed, and MOR10703 (100 nM) was added first and incubated for 1 h followed by NRG1 (10 ng) and/or COMPOUND A (1 μM). Each treatment was tested in triplicate. Electric impedance was measured in 1 h intervals after addition of drug until the end of the experiment. Cell index value, which is a dimensionless parameter derived as a relative change in measured electrical impedance to represent numbers of attached cells, was calculated from the electric impedance and plotted using the RTCA software provided by the vendor. At the end of the experiment, cell growth and/or viability was determined by measuring cellular ATP content using the CellTiter-Glo Luminescent Cell Viability Assay (Promega; Madison, Wis.) according to the manufacturer's protocol.

Statistical Analysis.

Data are expressed as the mean±SEM unless otherwise noted. The principal statistical test was a one-way ANOVA, and Tukey's posttest was used to compare all pairs of columns. A t test (two-tailed with unequal variance) was used when only two variables were present in the analysis. Significant differences in tumor growth were accomplished by determining the time it took (in days) to reach a specific blood Gluc activity. The survival curves were estimated using the Kaplan-Meier method, and the median survival day was used when determining statistical difference. Statistical significance is defined throughout the main text and figure legends. GraphPad Prism was used for all statistical analysis.

The invention claimed is:
1. A method of treating a brain metastases from breast cancer which comprises administering to a subject in need thereof a quantity of a jointly therapeutically effective pharmaceutical combination comprising:
(a) a compound of formula (I),

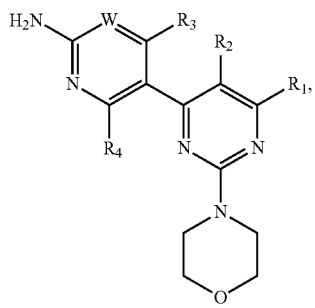

wherein W is $CR_w$ or N,
  wherein $R_w$ is selected from the group consisting of:
    (1) hydrogen,
    (2) cyano,
    (3) halogen,
    (4) methyl,
    (5) trifluoromethyl, and
    (6) sulfonamide;
  $R_1$ is selected from the group consisting of:
    (1) hydrogen,
    (2) cyano,
    (3) nitro,
    (4) halogen,
    (5) substituted and unsubstituted alkyl,
    (6) substituted and unsubstituted alkenyl,
    (7) substituted and unsubstituted alkynyl,
    (8) substituted and unsubstituted aryl,
    (9) substituted and unsubstituted heteroaryl,
    (10) substituted and unsubstituted heterocyclyl,
    (11) substituted and unsubstituted cycloalkyl,
    (12) —$COR_{1a}$,
    (13) —$CO_2R_{1a}$,
    (14) —$CONR_{1a}R_{1b}$,
    (15) —$NR_{1a}R_{1b}$,
    (16) —$NR_{1a}COR_{1b}$,
    (17) —$NR_{1a}SO_2R_{1b}$,
    (18) —$OCOR_{1a}$,
    (19) —$OR_{1a}$,
    (20) —$SR_{1a}$,
    (21) —$SOR_{1a}$, and
    (23) —$SO_2NR_{1a}R_{1b}$;
  wherein $R_{1a}$, and $R_{1b}$ are independently selected from the group consisting of:
    (a) hydrogen,
    (b) substituted or unsubstituted alkyl,
    (c) substituted and unsubstituted aryl,
    (d) substituted and unsubstituted heteroaryl,
    (e) substituted and unsubstituted heterocyclyl, and
    (f) substituted and unsubstituted cycloalkyl;
  $R_2$ is selected from the group consisting of:
    (1) hydrogen,
    (2) cyano,
    (3) nitro,
    (4) halogen,
    (5) hydroxy,
    (6) amino,
    (7) substituted and unsubstituted alkyl,
    (8) —$COR_{2a}$, and
    (9) —$NR_{2a}COR_{2b}$,
  wherein $R_{2a}$, and $R_{2b}$ are independently selected from the group consisting of:
    (a) hydrogen, and
    (b) substituted or unsubstituted alkyl;
  $R_3$ is selected from the group consisting of:
    (1) hydrogen,
    (2) cyano,
    (3) nitro,
    (4) halogen,
    (5) substituted and unsubstituted alkyl,
    (6) substituted and unsubstituted alkenyl,
    (7) substituted and unsubstituted alkynyl,
    (8) substituted and unsubstituted aryl,
    (9) substituted and unsubstituted heteroaryl,
    (10) substituted and unsubstituted heterocyclyl,
    (11) substituted and unsubstituted cycloalkyl,
    (12) —$COR_{3a}$,
    (13) —$NR_{3a}COR_{3b}$,
    (14) —$NR_{3a}R_{3b}$,
    (15) —$NR_{3a}SO_2R_{3b}$,
    (16) —$OR_{3a}$,
    (17) —$SR_{3a}$,
    (18) —$SOR_{3a}$,
    (19) —$SO_2R_{3a}$, wherein
  $R_{3a}$, and $R_{3b}$ are independently selected from the group consisting of:
    (a) hydrogen,
    (b) substituted or unsubstituted alkyl,
    (c) substituted and unsubstituted aryl,
    (d) substituted and unsubstituted heteroaryl,
    (e) substituted and unsubstituted heterocyclyl, and
    (f) substituted and unsubstituted cycloalkyl; and
  $R_4$ is selected from the group consisting of
    (1) hydrogen, and
    (2) halogen,
  or a pharmaceutically acceptable salt thereof, and
(b) a Her3 antibody or fragment thereof that recognizes a conformational epitope of a HER3 receptor comprising amino acid residues 265-277, and 315 within domain 2 and amino acid residues 571, 582-584, 596-597, 600-602, and 609-615 within domain 4 of the HER3 receptor of SEQ ID NO: 1, wherein the Her3 antibody or fragment thereof comprises a heavy chain variable region comprising CDR1 of SEQ ID NO: 128; CDR2 of SEQ ID NO: 129; and CDR3 of SEQ ID NO: 130;

and a light chain variable region comprising CDR1 of SEQ ID NO: 131; CDR2 of SEQ ID NO: 132; and CDR3 of SEQ ID NO: 133, and wherein the antibody or fragment thereof blocks both ligand-dependent and ligand-independent signal transduction, for simultaneous, separate or sequential administration for use in the treatment of a brain metastases from breast cancer.

2. The method of claim 1, wherein the compound of formula (I) is 5-(2,6-di-morpholin-4-yl-pyrimidin-4-yl)-4-trifluoromethyl-pyridin-2-ylamine, or a pharmaceutically acceptable salt thereof.

3. The method of claim 1, wherein the Her3 antagonist is administered every 7-28 days at a dosage of between 20 mg/ml-40 mg/ml and the compound of formula (I) or its pharmaceutically acceptable salts administered daily at a dose in the range of from about 60 mg/day to about 120 mg/day.

4. The method of claim 1, wherein the pharmaceutical combination is administered simultaneously, separately or sequentially.

5. The method of claim 1, wherein the compound of formula (I) is 5-(2,6-di-morpholin-4-yl-pyrimidin-4-yl)-4-trifluoromethyl-pyridin-2-ylamine, or its hydrochloride salt.

6. The method of claim 1, wherein the HER3 antibody or fragment thereof comprises a heavy chain variable region comprising SEQ ID NO: 141 and a light chain variable region comprising SEQ ID NO: 140.

7. The method of claim 1, wherein the HER3 antibody comprises a heavy chain comprising SEQ ID NO: 145 and a light chain comprising SEQ ID NO: 144.

8. A method of treating a brain metastases from breast cancer which comprises administering to a subject in need thereof a quantity of a jointly therapeutically effective pharmaceutical combination comprising:
(a) a compound of formula (I),

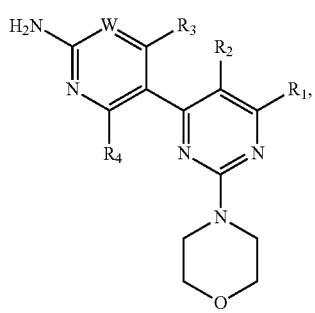

(I)

wherein W is $CR_w$ or N,
wherein $R_w$ is selected from the group consisting of:
(1) hydrogen,
(2) cyano,
(3) halogen,
(4) methyl,
(5) trifluoromethyl, and
(6) sulfonamide;
$R_1$ is selected from the group consisting of:
(1) hydrogen,
(2) cyano,
(3) nitro,
(4) halogen,
(5) substituted and unsubstituted alkyl,
(6) substituted and unsubstituted alkenyl,
(7) substituted and unsubstituted alkynyl,
(8) substituted and unsubstituted aryl,
(9) substituted and unsubstituted heteroaryl,
(10) substituted and unsubstituted heterocyclyl,
(11) substituted and unsubstituted cycloalkyl,
(12) —$COR_{1a}$,
(13) —$CO_2R_{1a}$,
(14) —$CONR_{1a}R_{1b}$,
(15) —$NR_{1a}R_{1b}$,
(16) —$NR_{1a}COR_{1b}$,
(17) —$NR_{1a}SO_2R_{1b}$,
(18) —$OCOR_{1a}$,
(19) —$OR_{1a}$,
(20) —$SR_{1a}$,
(21) —$SOR_{1a}$, and
(23) —$SO_2NR_{1a}R_{1b}$;
wherein $R_{1a}$, and $R_{1b}$ are independently selected from the group consisting of:
(a) hydrogen,
(b) substituted or unsubstituted alkyl,
(c) substituted and unsubstituted aryl,
(d) substituted and unsubstituted heteroaryl,
(e) substituted and unsubstituted heterocyclyl, and
(f) substituted and unsubstituted cycloalkyl;
$R_2$ is selected from the group consisting of:
(1) hydrogen,
(2) cyano,
(3) nitro,
(4) halogen,
(5) hydroxy,
(6) amino,
(7) substituted and unsubstituted alkyl,
(8) —$COR_{2a}$, and
(9) —$NR_{2a}COR_{2b}$,
wherein $R_{2a}$, and $R_{2b}$ are independently selected from the group consisting of:
(a) hydrogen, and
(b) substituted or unsubstituted alkyl;
$R_3$ is selected from the group consisting of:
(1) hydrogen,
(2) cyano,
(3) nitro,
(4) halogen,
(5) substituted and unsubstituted alkyl,
(6) substituted and unsubstituted alkenyl,
(7) substituted and unsubstituted alkynyl,
(8) substituted and unsubstituted aryl,
(9) substituted and unsubstituted heteroaryl,
(10) substituted and unsubstituted heterocyclyl,
(11) substituted and unsubstituted cycloalkyl,
(12) —$COR_{3a}$,
(13) —$NR_{3a}COR_{3b}$,
(14) —$NR_{3a}R_{3b}$,
(15) —$NR_{3a}SO_2R_{3b}$,
(16) —$OR_{3a}$,
(17) —$SR_{3a}$,
(18) —$SOR_{3a}$,
(19) —$SO_2R_{3a}$, wherein
$R_{3a}$, and $R_{3b}$ are independently selected from the group consisting of:
(a) hydrogen,
(b) substituted or unsubstituted alkyl,
(c) substituted and unsubstituted aryl,
(d) substituted and unsubstituted heteroaryl,
(e) substituted and unsubstituted heterocyclyl, and
(f) substituted and unsubstituted cycloalkyl; and R$_4$ is selected from the group consisting of
  (1) hydrogen, and
  (2) halogen,
  or a pharmaceutically acceptable salt thereof, and
(b) a Her3 antibody or fragment thereof, wherein the Her3 antibody or fragment thereof comprises a heavy chain variable region comprising CDR1 of SEQ ID NO: 128; CDR2 of SEQ ID NO: 129; and CDR3 of SEQ ID NO: 130; and a light chain variable region comprising CDR1 of SEQ ID NO: 131; CDR2 of SEQ ID NO: 132; and CDR3 of SEQ ID NO: 133, and wherein the Her3 antibody or fragment thereof blocks both ligand-dependent and ligand-independent signal transduction, for simultaneous, separate or sequential administration for use in the treatment of a brain metastases from breast cancer.

9. The method of claim 8, wherein the compound of formula (I) is 5-(2,6-dimorpholin-4-yl-pyrimidin-4-yl)-4-trifluoromethyl-pyridin-2-ylamine, or a pharmaceutically acceptable salt thereof.

10. The method of claim 8, wherein the Her3 antagonist is administered every 7-28 days at a dosage of between 20 mg/ml-40 mg/ml and the compound of formula (I) or its pharmaceutically acceptable salts administered daily at a dose in the range of from about 60 mg/day to about 120 mg/day.

11. The method of claim 8, wherein the pharmaceutical combination is administered simultaneously, separately or sequentially.

12. The method of claim 8, wherein the compound of formula (I) is 5-(2,6-dimorpholin-4-yl-pyrimidin-4-yl)-4-trifluoromethyl-pyridin-2-ylamine, or its hydrochloride salt.

13. The method of claim 8, wherein the HER3 antibody or fragment thereof comprises a heavy chain variable region comprising SEQ ID NO: 141 and a light chain variable region comprising SEQ ID NO: 140.

14. The method of claim 8, wherein the HER3 antibody comprises a heavy chain comprising SEQ ID NO: 145 and a light chain comprising SEQ ID NO: 144.

\* \* \* \* \*

UNITED STATES PATENT AND TRADEMARK OFFICE
CERTIFICATE OF CORRECTION

| | |
|---|---|
| PATENT NO. | : 10,689,459 B2 |
| APPLICATION NO. | : 15/535405 |
| DATED | : June 23, 2020 |
| INVENTOR(S) | : Qing Sheng et al. |

It is certified that error appears in the above-identified patent and that said Letters Patent is hereby corrected as shown below:

In the Specification

Column 1, Line 9, please insert the following paragraph:
--GOVERNMENT FUNDING
This invention was made with government support under W81XWH-10-1-0016 awarded by the Medical Research and Development Command. The government has certain rights in the invention.--

Signed and Sealed this
Ninth Day of May, 2023

Katherine Kelly Vidal
*Director of the United States Patent and Trademark Office*

SEQUENCE LISTING

```
<160> NUMBER OF SEQ ID NOS: 379

<210> SEQ ID NO 1
<211> LENGTH: 1342
<212> TYPE: PRT
<213> ORGANISM: Homo sapiens

<400> SEQUENCE: 1

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190
```

-continued

```
Arg Cys Trp Gly Pro Gly Ser Glu Asp Cys Gln Thr Leu Thr Lys Thr
        195                 200                 205
Ile Cys Ala Pro Gln Cys Asn Gly His Cys Phe Gly Pro Asn Pro Asn
        210                 215                 220
Gln Cys Cys His Asp Glu Cys Ala Gly Gly Cys Ser Gly Pro Gln Asp
225                 230                 235                 240
Thr Asp Cys Phe Ala Cys Arg His Phe Asn Asp Ser Gly Ala Cys Val
                245                 250                 255
Pro Arg Cys Pro Gln Pro Leu Val Tyr Asn Lys Leu Thr Phe Gln Leu
            260                 265                 270
Glu Pro Asn Pro His Thr Lys Tyr Gln Tyr Gly Gly Val Cys Val Ala
        275                 280                 285
Ser Cys Pro His Asn Phe Val Val Asp Gln Thr Ser Cys Val Arg Ala
        290                 295                 300
Cys Pro Pro Asp Lys Met Glu Val Asp Lys Asn Gly Leu Lys Met Cys
305                 310                 315                 320
Glu Pro Cys Gly Gly Leu Cys Pro Lys Ala Cys Glu Gly Thr Gly Ser
                325                 330                 335
Gly Ser Arg Phe Gln Thr Val Asp Ser Ser Asn Ile Asp Gly Phe Val
            340                 345                 350
Asn Cys Thr Lys Ile Leu Gly Asn Leu Asp Phe Leu Ile Thr Gly Leu
        355                 360                 365
Asn Gly Asp Pro Trp His Lys Ile Pro Ala Leu Asp Pro Glu Lys Leu
        370                 375                 380
Asn Val Phe Arg Thr Val Arg Glu Ile Thr Gly Tyr Leu Asn Ile Gln
385                 390                 395                 400
Ser Trp Pro Pro His Met His Asn Phe Ser Val Phe Ser Asn Leu Thr
                405                 410                 415
Thr Ile Gly Gly Arg Ser Leu Tyr Asn Arg Gly Phe Ser Leu Leu Ile
            420                 425                 430
Met Lys Asn Leu Asn Val Thr Ser Leu Gly Phe Arg Ser Leu Lys Glu
        435                 440                 445
Ile Ser Ala Gly Arg Ile Tyr Ile Ser Ala Asn Arg Gln Leu Cys Tyr
        450                 455                 460
His His Ser Leu Asn Trp Thr Lys Val Leu Arg Gly Pro Thr Glu Glu
465                 470                 475                 480
Arg Leu Asp Ile Lys His Asn Arg Pro Arg Arg Asp Cys Val Ala Glu
                485                 490                 495
Gly Lys Val Cys Asp Pro Leu Cys Ser Ser Gly Gly Cys Trp Gly Pro
            500                 505                 510
Gly Pro Gly Gln Cys Leu Ser Cys Arg Asn Tyr Ser Arg Gly Gly Val
        515                 520                 525
Cys Val Thr His Cys Asn Phe Leu Asn Gly Glu Pro Arg Glu Phe Ala
        530                 535                 540
His Glu Ala Glu Cys Phe Ser Cys His Pro Glu Cys Gln Pro Met Glu
545                 550                 555                 560
Gly Thr Ala Thr Cys Asn Gly Ser Gly Ser Asp Thr Cys Ala Gln Cys
                565                 570                 575
Ala His Phe Arg Asp Gly Pro His Cys Val Ser Ser Cys Pro His Gly
            580                 585                 590
Val Leu Gly Ala Lys Gly Pro Ile Tyr Lys Tyr Pro Asp Val Gln Asn
        595                 600                 605
```

-continued

```
Glu Cys Arg Pro Cys His Glu Asn Cys Thr Gln Cys Lys Gly Pro
    610                 615                 620
Glu Leu Gln Asp Cys Leu Gly Gln Thr Leu Val Leu Ile Gly Lys Thr
625                 630                 635                 640
His Leu Thr Met Ala Leu Thr Val Ile Ala Gly Leu Val Val Ile Phe
                645                 650                 655
Met Met Leu Gly Gly Thr Phe Leu Tyr Trp Arg Gly Arg Arg Ile Gln
            660                 665                 670
Asn Lys Arg Ala Met Arg Arg Tyr Leu Glu Arg Gly Glu Ser Ile Glu
        675                 680                 685
Pro Leu Asp Pro Ser Glu Lys Ala Asn Lys Val Leu Ala Arg Ile Phe
    690                 695                 700
Lys Glu Thr Glu Leu Arg Lys Leu Lys Val Leu Gly Ser Gly Val Phe
705                 710                 715                 720
Gly Thr Val His Lys Gly Val Trp Ile Pro Glu Gly Glu Ser Ile Lys
                725                 730                 735
Ile Pro Val Cys Ile Lys Val Ile Glu Asp Lys Ser Gly Arg Gln Ser
            740                 745                 750
Phe Gln Ala Val Thr Asp His Met Leu Ala Ile Gly Ser Leu Asp His
        755                 760                 765
Ala His Ile Val Arg Leu Leu Gly Leu Cys Pro Gly Ser Ser Leu Gln
    770                 775                 780
Leu Val Thr Gln Tyr Leu Pro Leu Gly Ser Leu Leu Asp His Val Arg
785                 790                 795                 800
Gln His Arg Gly Ala Leu Gly Pro Gln Leu Leu Leu Asn Trp Gly Val
                805                 810                 815
Gln Ile Ala Lys Gly Met Tyr Tyr Leu Glu Glu His Gly Met Val His
            820                 825                 830
Arg Asn Leu Ala Ala Arg Asn Val Leu Leu Lys Ser Pro Ser Gln Val
        835                 840                 845
Gln Val Ala Asp Phe Gly Val Ala Asp Leu Leu Pro Pro Asp Asp Lys
    850                 855                 860
Gln Leu Leu Tyr Ser Glu Ala Lys Thr Pro Ile Lys Trp Met Ala Leu
865                 870                 875                 880
Glu Ser Ile His Phe Gly Lys Tyr Thr His Gln Ser Asp Val Trp Ser
                885                 890                 895
Tyr Gly Val Thr Val Trp Glu Leu Met Thr Phe Gly Ala Glu Pro Tyr
            900                 905                 910
Ala Gly Leu Arg Leu Ala Glu Val Pro Asp Leu Leu Glu Lys Gly Glu
        915                 920                 925
Arg Leu Ala Gln Pro Gln Ile Cys Thr Ile Asp Val Tyr Met Val Met
    930                 935                 940
Val Lys Cys Trp Met Ile Asp Glu Asn Ile Arg Pro Thr Phe Lys Glu
945                 950                 955                 960
Leu Ala Asn Glu Phe Thr Arg Met Ala Arg Asp Pro Pro Arg Tyr Leu
                965                 970                 975
Val Ile Lys Arg Glu Ser Gly Pro Gly Ile Ala Pro Gly Pro Glu Pro
            980                 985                 990
His Gly Leu Thr Asn Lys Lys Leu  Glu Glu Val Glu Leu  Glu Pro Glu
        995                 1000                1005
Leu Asp  Leu Asp  Leu Asp  Leu  Glu Ala Glu Glu Asp  Asn Leu Ala
    1010            1015            1020
```

-continued

```
Thr Thr Thr Leu Gly Ser Ala Leu Ser Leu Pro Val Gly Thr Leu
1025                1030                1035

Asn Arg Pro Arg Gly Ser Gln Ser Leu Leu Ser Pro Ser Ser Gly
1040                1045                1050

Tyr Met Pro Met Asn Gln Gly Asn Leu Gly Glu Ser Cys Gln Glu
1055                1060                1065

Ser Ala Val Ser Gly Ser Ser Glu Arg Cys Pro Arg Pro Val Ser
1070                1075                1080

Leu His Pro Met Pro Arg Gly Cys Leu Ala Ser Glu Ser Ser Glu
1085                1090                1095

Gly His Val Thr Gly Ser Glu Ala Glu Leu Gln Glu Lys Val Ser
1100                1105                1110

Met Cys Arg Ser Arg Ser Arg Ser Arg Ser Pro Arg Pro Arg Gly
1115                1120                1125

Asp Ser Ala Tyr His Ser Gln Arg His Ser Leu Leu Thr Pro Val
1130                1135                1140

Thr Pro Leu Ser Pro Pro Gly Leu Glu Glu Glu Asp Val Asn Gly
1145                1150                1155

Tyr Val Met Pro Asp Thr His Leu Lys Gly Thr Pro Ser Ser Arg
1160                1165                1170

Glu Gly Thr Leu Ser Ser Val Gly Leu Ser Ser Val Leu Gly Thr
1175                1180                1185

Glu Glu Glu Asp Glu Asp Glu Glu Tyr Glu Tyr Met Asn Arg Arg
1190                1195                1200

Arg Arg His Ser Pro Pro His Pro Pro Arg Pro Ser Ser Leu Glu
1205                1210                1215

Glu Leu Gly Tyr Glu Tyr Met Asp Val Gly Ser Asp Leu Ser Ala
1220                1225                1230

Ser Leu Gly Ser Thr Gln Ser Cys Pro Leu His Pro Val Pro Ile
1235                1240                1245

Met Pro Thr Ala Gly Thr Thr Pro Asp Glu Asp Tyr Glu Tyr Met
1250                1255                1260

Asn Arg Gln Arg Asp Gly Gly Gly Pro Gly Gly Asp Tyr Ala Ala
1265                1270                1275

Met Gly Ala Cys Pro Ala Ser Glu Gln Gly Tyr Glu Glu Met Arg
1280                1285                1290

Ala Phe Gln Gly Pro Gly His Gln Ala Pro His Val His Tyr Ala
1295                1300                1305

Arg Leu Lys Thr Leu Arg Ser Leu Glu Ala Thr Asp Ser Ala Phe
1310                1315                1320

Asp Asn Pro Asp Tyr Trp His Ser Arg Leu Phe Pro Lys Ala Asn
1325                1330                1335

Ala Gln Arg Thr
1340
```

```
<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Tyr Ala Met Ser
1               5
```

```
<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Thr Gly Ala Val Gly Arg Thr Tyr Tyr Pro Asp Ser Val Lys Gly
1               5                   10                  15

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Trp Gly Asp Glu Gly Phe Asp Ile
1               5

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ala Ser Gln Gly Ile Ser Asn Trp Leu Ala
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Ala Ser Ser Leu Gln Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Gln Tyr Ser Ser Phe Pro Thr Thr
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 8

Gly Phe Thr Phe Ser Ser Tyr
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Ala Val Gly Arg
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Trp Gly Asp Glu Gly Phe Asp Ile
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Gln Gly Ile Ser Asn Trp
1               5

<210> SEQ ID NO 12
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Ala Ser
1

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Ser Ser Phe Pro Thr
1               5
```

-continued

```
<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 15
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Arg Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Trp Gly Asp Glu Gly Phe Asp Ile Trp Gly Gln Gly Thr Leu Val
            100                 105                 110

Thr Val Ser Ser
        115

<210> SEQ ID NO 16
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 16

```
gatatccaga tgacccagag cccgtctagc ctgagcgcga gcgtgggtga tcgtgtgacc    60
attacctgca gagcgagcca gggtatttct aattggctgg cttggtacca gcagaaacca   120
ggtaaagcac cgaaactatt aatttatggt gcttcttctt tgcaaagcgg ggtcccgtcc   180
cgttttagcg gctctggatc cggcactgat tttaccctga ccattagcag cctgcaacct   240
gaagactttg cggtttatta ttgccagcag tattcttctt ttcctactac ctttggccag   300
ggtacgaaag ttgaaattaa a                                             321
```

<210> SEQ ID NO 17
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
caggtgcaat tggtggaaag cggcggcggc ctggtgcaac cgggcggcag cctgcgtctg    60
agctgcgcgg cctccggatt tacctttagc agctatgcga tgagctgggt gcgccaagcc   120
cctgggaagg gtctcgagtg ggtgagcgtt actggtgctg ttggtcgtac ttattatcct   180
gattctgtta agggtcgttt taccatttca cgtgataatt cgaaaaacac cctgtatctg   240
caaatgaaca gcctgcgtgc ggaagatacg gccgtgtatt attgcgcgcg ttggggtgat   300
gagggttttg atatttgggg ccaaggcacc ctggtgacgg ttagctca                348
```

<210> SEQ ID NO 18
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 19
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Arg Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Trp Gly Asp Glu Gly Phe Asp Ile Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300
```

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
    435                 440                 445

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Tyr Ala Met Ser
1               5

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Ile Ser Ala Trp Gly His Val Lys Tyr Tyr Ala Asp Ser Val Lys
1               5                   10                  15

Gly

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Trp Gly Asp Glu Gly Phe Asp Ile
1               5

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 23

Arg Ala Ser Gln Gly Ile Ser Asn Trp Leu Ala
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Ala Ser Ser Leu Gln Ser
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Gln Tyr Ser Ser Phe Pro Thr Thr
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Phe Thr Phe Ser Ser Tyr
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Ala Trp Gly His Val
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Trp Gly Asp Glu Gly Phe Asp Ile
1               5
```

```
<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Gln Gly Ile Ser Asn Trp
1               5

<210> SEQ ID NO 30
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Ala Ser
1

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Tyr Ser Ser Phe Pro Thr
1               5

<210> SEQ ID NO 32
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 33
<211> LENGTH: 117
<212> TYPE: PRT
<213> ORGANISM: Artificial Sequence
```

<220> FEATURE:
<223> OTHER INFORMATION: Description of Artificial Sequence: Synthetic
    polypeptide

<400> SEQUENCE: 33

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Ala Trp Gly His Val Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
        115
```

<210> SEQ ID NO 34
<211> LENGTH: 321
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 34

```
gatatccaga tgacccagag cccgtctagc ctgagcgcga gcgtgggtga tcgtgtgacc    60
attacctgca gcgagccca gggtatttct aattggctgg cttggtacca gcagaaacca   120
ggtaaagcac cgaaactatt aatttatggt gcttcttctt tgcaaagcgg ggtcccgtcc   180
cgttttagcg gctctggatc cggcactgat tttaccctga ccattagcag cctgcaacct   240
gaagactttg cggtttatta ttgccagcag tattcttctt ttcctactac ctttggccag   300
ggtacgaaag ttgaaattaa a                                             321
```

<210> SEQ ID NO 35
<211> LENGTH: 351
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 35

```
caggtgcaat tggtggaaag cggcggcggc ctggtgcaac cgggcggcag cctgcgtctg    60
agctgcgcgg cctccggatt tacctttagc agctatgcga tgagctgggt gcgccaagcc   120
cctgggaagg gtctcgagtg ggtgagcgtt atttctgctt ggggtcatgt taagtattat   180
gctgattctg ttaagggtcg ttttaccatt tcacgtgata attcgaaaaa caccctgtat   240
ctgcaaatga acagcctgcg tgcggaagat acggccgtgt attattgcgc gcgttggggt   300
gatgagggtt ttgatatttg gggccaaggc accctggtga cggttagctc a            351
```

```
<210> SEQ ID NO 36
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 37
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Ala Trp Gly His Val Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Arg Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 38

Ser Tyr Ala Met Ser
1               5

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Ile Asn Ser Gln Gly Lys Ser Thr Tyr Tyr Ala Asp Ser Val Lys
1               5                   10                  15

Gly

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Trp Gly Asp Glu Gly Phe Asp Ile
1               5

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Ala Ser Gln Gly Ile Ser Asn Trp Leu Ala
1               5                   10

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Ala Ser Ser Leu Gln Ser
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Gln Tyr Ser Ser Phe Pro Thr Thr
1               5
```

```
<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Phe Thr Phe Ser Ser Tyr
1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asn Ser Gln Gly Lys Ser
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Trp Gly Asp Glu Gly Phe Asp Ile
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Gln Gly Ile Ser Asn Trp
1               5

<210> SEQ ID NO 48
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Ala Ser
1

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 49

Tyr Ser Ser Phe Pro Thr
1               5

<210> SEQ ID NO 50
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 51
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
        115

<210> SEQ ID NO 52
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
gatatccaga tgacccagag cccgtctagc ctgagcgcga gcgtgggtga tcgtgtgacc    60
attacctgca gagcgagcca gggtatttct aattggctgg cttggtacca gcagaaacca   120
ggtaaagcac cgaaactatt aatttatggt gcttcttctt tgcaaagcgg ggtcccgtcc   180
cgttttagcg gctctggatc cggcactgat tttaccctga ccattagcag cctgcaacct   240
gaagactttg cggtttatta ttgccagcag tattcttctt ttcctactac ctttggccag   300
ggtacgaaag ttgaaattaa a                                             321

<210> SEQ ID NO 53
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
caggtgcaat tggtggaaag cggcggcggc ctggtgcaac cgggcggcag cctgcgtctg    60
agctgcgcgg cctccggatt tacctttagc agctatgcga tgagctgggt gcgccaagcc   120
cctgggaagg gtctcgagtg ggtgagcgct attaattctc agggtaagtc tacttattat   180
gctgattctg ttaagggtcg ttttaccatt tcacgtgata attcgaaaaa caccctgtat   240
ctgcaaatga acagcctgcg tgcggaagat acggccgtgt attattgcgc gcgttggggt   300
gatgagggtt tgatatttg gggccaaggc accctggtga cggttagctc a            351

<210> SEQ ID NO 54
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 55
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

-continued

```
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Tyr Ala Met Ser
1               5

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Val Ile Asn Pro Ser Gly Asn Phe Thr Asn Tyr Ala Asp Ser Val Lys
1               5                   10                  15
Gly

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Trp Gly Asp Glu Gly Phe Asp Ile
1               5

<210> SEQ ID NO 59
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 59

Arg Ala Ser Gln Gly Ile Ser Asn Trp Leu Ala
1               5                   10

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Ala Ser Ser Leu Gln Ser
1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Gln Tyr Ser Ser Phe Pro Thr Thr
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Phe Thr Phe Ser Ser Tyr
1               5

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asn Pro Ser Gly Asn Phe
1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Trp Gly Asp Glu Gly Phe Asp Ile
1               5
```

```
<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Gln Gly Ile Ser Asn Trp
1               5

<210> SEQ ID NO 66
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Ala Ser
1

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Tyr Ser Ser Phe Pro Thr
1               5

<210> SEQ ID NO 68
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 69
<211> LENGTH: 117
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 69

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Asn Pro Ser Gly Asn Phe Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
        115

<210> SEQ ID NO 70
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
gatatccaga tgacccagag cccgtctagc ctgagcgcga gcgtgggtga tcgtgtgacc      60
attacctgca gcgagcca gggtatttct aattggctgg cttggtacca gcagaaacca      120
ggtaaagcac cgaaactatt aatttatggt gcttcttctt tgcaaagcgg ggtcccgtcc      180
cgttttagcg gctctggatc cggcactgat tttaccctga ccattagcag cctgcaacct      240
gaagactttg cggtttatta ttgccagcag tattcttctt ttcctactac ctttggccag      300
ggtacgaaag ttgaaattaa a                                                321

<210> SEQ ID NO 71
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
caggtgcaat tggtggaaag cggcggcggc ctggtgcaac cgggcggcag cctgcgtctg      60
agctgcgcgg cctccggatt tacctttagc agctatgcga tgagctgggt gcgccaagcc      120
cctgggaagg gtctcgagtg ggtgagcgtt attaatcctt ctggtaattt tactaattat      180
gctgattctg ttaagggtcg ttttaccatt tcacgtgata attcgaaaaa cacccctgtat     240 ctgcaaatga acagcctgcg tgcggaagat acggccgtgt attattgcgc gcgttggggt      300
gatgagggtt ttgatatttg gggccaaggc accctggtga cggttagctc a              351

```
<210> SEQ ID NO 72
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 73
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Asn Pro Ser Gly Asn Phe Thr Asn Tyr Ala Asp Ser Val
50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130             135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
            210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 74

Ser Tyr Ala Met Ser
1               5

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Asn Thr Ser Pro Ile Gly Tyr Thr Tyr Tyr Ala Gly Ser Val Lys Gly
1               5                   10                  15

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Trp Gly Asp Glu Gly Phe Asp Ile
1               5

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Arg Ala Ser Gln Gly Ile Ser Asn Trp Leu Ala
1               5                   10

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Ala Ser Ser Leu Gln Ser
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gln Gln Tyr Ser Ser Phe Pro Thr Thr
1               5
```

```
<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Phe Thr Phe Ser Ser Tyr
1               5

<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ser Pro Ile Gly Tyr
1               5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Trp Gly Asp Glu Gly Phe Asp Ile
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ser Gln Gly Ile Ser Asn Trp
1               5

<210> SEQ ID NO 84
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Ala Ser
1

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85
```

Tyr Ser Ser Phe Pro Thr
1               5

<210> SEQ ID NO 86
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 87
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asn Thr Ser Pro Ile Gly Tyr Thr Tyr Tyr Ala Gly Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Trp Gly Asp Glu Gly Phe Asp Ile Trp Gly Gln Gly Thr Leu Val
            100                 105                 110

Thr Val Ser Ser
        115

<210> SEQ ID NO 88
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88

```
gatatccaga tgacccagag cccgtctagc ctgagcgcga gcgtgggtga tcgtgtgacc    60
attacctgca gagcgagcca gggtatttct aattggctgg cttggtacca gcagaaacca   120
ggtaaagcac cgaaactatt aatttatggt gcttcttctt tgcaaagcgg ggtcccgtcc   180
cgttttagcg gctctggatc cggcactgat tttaccctga ccattagcag cctgcaacct   240
gaagactttg cggtttatta ttgccagcag tattcttctt ttcctactac ctttggccag   300
ggtacgaaag ttgaaattaa a                                             321
```

<210> SEQ ID NO 89
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89

```
caggtgcaat tggtggaaag cggcggcggc ctggtgcaac cgggcggcag cctgcgtctg    60
agctgcgcgg cctccggatt tacctttagc agctatgcga tgagctgggt gcgccaagcc   120
cctgggaagg gtctcgagtg ggtgagcaat acttctccta ttggttatac ttattatgct   180
ggttctgtta agggtcgttt taccatttca cgtgataatt cgaaaaacac cctgtatctg   240
caaatgaaca gcctgcgtgc ggaagatacg gccgtgtatt attgcgcgcg ttggggtgat   300
gagggttttg atatttgggg ccaaggcacc ctggtgacgg ttagctca                348
```

<210> SEQ ID NO 90
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Ala
            210

<210> SEQ ID NO 91
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asn Thr Ser Pro Ile Gly Tyr Thr Tyr Ala Gly Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Trp Gly Asp Glu Gly Phe Asp Ile Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser
            210                 215

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ser Tyr Ala Met Ser
1               5

<210> SEQ ID NO 93
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Val Thr Gly Ala Val Gly Arg Ser Thr Tyr Tyr Pro Asp Ser Val Lys
1               5                   10                  15

Gly

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Trp Gly Asp Glu Gly Phe Asp Ile
1               5

<210> SEQ ID NO 95
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Ala Ser Gln Gly Ile Ser Asn Trp Leu Ala
1               5                   10

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Ala Ser Ser Leu Gln Ser
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gln Gln Tyr Ser Ser Phe Pro Thr Thr
1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 98

Gly Phe Thr Phe Ser Ser Tyr
1               5

<210> SEQ ID NO 99
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Ala Val Gly Arg Ser
1               5

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Trp Gly Asp Glu Gly Phe Asp Ile
1               5

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ser Gln Gly Ile Ser Asn Trp
1               5

<210> SEQ ID NO 102
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Ala Ser
1

<210> SEQ ID NO 103
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Tyr Ser Ser Phe Pro Thr
1               5

<210> SEQ ID NO 104

<210> SEQ ID NO 104
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 105
<211> LENGTH: 117
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 105

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Arg Ser Thr Tyr Tyr Pro Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
        115

<210> SEQ ID NO 106
<211> LENGTH: 321
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 106
gatatccaga tgacccagag ccccagcagc ctgagcgcca gcgtgggcga cagagtgacc      60
atcacctgtc gggccagcca gggcatcagc aactggctgg cctggtatca gcagaagccc     120

```
ggcaaggccc ccaagctgct gatctacggc gccagctccc tgcagagcgg cgtgccaagc    180
agattcagcg gcagcggctc cggcaccgac ttcaccctga ccatcagcag cctgcagccc    240
gaggacttcg ccacctacta ctgccagcag tacagcagct cccccaccac cttcggccag    300
ggcaccaagg tggaaatcaa g                                              321
```

<210> SEQ ID NO 107
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 107

```
gaggtgcaat tgctggaaag cggcggaggc ctggtgcagc ctggcggcag cctgagactg    60
tcttgcgccg ccagcggctt caccttcagc agctacgcca tgagctgggt ccgccaggcc    120
cctggcaagg gactggaatg ggtgtccgtg acaggcgccg tgggcagaag cacctactac    180
cccgacagcg tgaagggccg gttcaccatc agccgggaca acagcaagaa caccctgtac    240
ctgcagatga acagcctgcg ggccgaggac accgccgtgt actactgtgc cagatggggc    300
gacgagggct tcgacatctg gggccagggc accctggtca ccgtcagctc a            351
```

<210> SEQ ID NO 108
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 108

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
            195                 200                 205

Phe Asn Arg Gly Glu Cys
    210

<210> SEQ ID NO 109
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Arg Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335
```

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 110
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ser Tyr Ala Met Ser
1               5

<210> SEQ ID NO 111
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Val Ile Ser Ala Trp Gly His Val Lys Tyr Tyr Ala Asp Ser Val Lys
1               5                   10                  15

Gly

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Trp Gly Asp Glu Gly Phe Asp Ile
1               5

<210> SEQ ID NO 113
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Arg Ala Ser Gln Gly Ile Ser Asn Trp Leu Ala
1               5                   10

```
<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gly Ala Ser Ser Leu Gln Ser
1               5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gln Gln Tyr Ser Ser Phe Pro Thr Thr
1               5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Phe Thr Phe Ser Ser Tyr
1               5

<210> SEQ ID NO 117
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ser Ala Trp Gly His Val
1               5

<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Trp Gly Asp Glu Gly Phe Asp Ile
1               5

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 119

Ser Gln Gly Ile Ser Asn Trp
1               5

<210> SEQ ID NO 120
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Ala Ser
1

<210> SEQ ID NO 121
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Tyr Ser Ser Phe Pro Thr
1               5

<210> SEQ ID NO 122
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 123
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Ser Tyr
        20                  25                  30

Ala Met Ser Trp Val Arg Gln Ala Pro Gly Lys Gly Leu Glu Trp Val
            35                  40                  45

Ser Val Ile Ser Ala Trp Gly His Val Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
            115

<210> SEQ ID NO 124
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
gatatccaga tgacccagag ccccagcagc ctgagcgcca gcgtgggcga cagagtgacc        60
atcacctgtc gggccagcca gggcatcagc aactggctgg cctggtatca gcagaagccc       120
ggcaaggccc ccaagctgct gatctacggc gccagctccc tgcagagcgg cgtgccaagc       180
agattcagcg gcagcggctc cggcaccgac ttcacccctga ccatcagcag cctgcagccc      240
gaggacttcg ccacctacta ctgccagcag tacagcagct cccccaccac cttcggccag       300
ggcaccaagg tggaaatcaa g                                                 321

<210> SEQ ID NO 125
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
gaggtgcaat tgctggaaag cggcggaggc ctggtgcagc ctggcggcag cctgagactg        60
tcttgcgccg ccagcggctt caccttcagc agctacgcca tgagctgggt ccgccaggcc       120
cctggcaagg gactggaatg ggtgtccgtg atcagcgcct ggggccacgt gaagtactac       180
gccgacagcg tgaagggccg gttcaccatc agccgggaca acagcaagaa cacccctgtac      240 ctgcagatga acagcctgcg ggccgaggac accgccgtgt actactgtgc cagatggggc       300
gacgagggct tcgacatctg gggccagggc accctggtca ccgtcagctc a                351

<210> SEQ ID NO 126
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 127
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Ala Trp Gly His Val Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140
```

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 128
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ser Tyr Ala Met Ser
1               5

<210> SEQ ID NO 129
<211> LENGTH: 17
<212> TYPE: PRT
<213> ORGANISM: Artificial Sequence
<220> FEATURE:
<223> OTHER INFORMATION: Description of Artificial Sequence: Synthetic

```
                       peptide

<400> SEQUENCE: 129

Ala Ile Asn Ser Gln Gly Lys Ser Thr Tyr Tyr Ala Asp Ser Val Lys
1               5                   10                  15
Gly

<210> SEQ ID NO 130
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Trp Gly Asp Glu Gly Phe Asp Ile
1               5

<210> SEQ ID NO 131
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Arg Ala Ser Gln Gly Ile Ser Asn Trp Leu Ala
1               5                   10

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gly Ala Ser Ser Leu Gln Ser
1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gln Gln Tyr Ser Ser Phe Pro Thr Thr
1               5

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gly Phe Thr Phe Ser Ser Tyr
1               5
```

<210> SEQ ID NO 135
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asn Ser Gln Gly Lys Ser
1               5

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Trp Gly Asp Glu Gly Phe Asp Ile
1               5

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ser Gln Gly Ile Ser Asn Trp
1               5

<210> SEQ ID NO 138
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Ala Ser
1

<210> SEQ ID NO 139
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Tyr Ser Ser Phe Pro Thr
1               5

<210> SEQ ID NO 140
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 141
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
        115

<210> SEQ ID NO 142
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 142
gatatccaga tgacccagag ccccagcagc ctgagcgcca gcgtgggcga cagagtgacc      60
atcacctgtc gggccagcca gggcatcagc aactggctgg cctggtatca gcagaagccc    120
ggcaaggccc ccaagctgct gatctacggc gccagctccc tgcagagcgg cgtgccaagc    180
agattcagcg gcagcggctc cggcaccgac ttcaccctga ccatcagcag cctgcagccc    240
gaggacttcg ccacctacta ctgccagcag tacagcagct cccccaccac cttcggccag    300
ggcaccaagg tggaaatcaa g                                           321

<210> SEQ ID NO 143
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 143
gaggtgcaat tgctggaaag cggcggaggc ctggtgcagc ctggcggcag cctgagactg      60
tcttgcgccg ccagcggctt caccttcagc agctacgcca tgagctgggt ccgccaggcc     120
cctggcaagg gactggaatg ggtgtccgcc atcaacagcc agggcaagag cacctactac     180
gccgacagcg tgaagggccg gttcaccatc agcggggaca acagcaagaa cacccctgtac    240 ctgcagatga acagcctgcg ggccgaggac accgccgtgt actactgtgc cagatggggc     300
gacgagggct cgacatctg gggccagggc accctggtca ccgtcagctc a              351

<210> SEQ ID NO 144
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 145
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

```
Val Lys Gly Phe Tyr Pro Ser Asp Ile Ala Val Glu Trp Glu Ser Asn
        370                 375                 380
Gly Gln Pro Glu Asn Asn Tyr Lys Thr Thr Pro Pro Val Leu Asp Ser
    385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
                420                 425                 430
His Asn His Tyr Thr Gln Lys Ser Leu Ser Leu Ser Pro Gly Lys
            435                 440                 445

<210> SEQ ID NO 146
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ser Tyr Ala Met Ser
1               5

<210> SEQ ID NO 147
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ala Ile Ser Ser Gln Gly Lys Ser Thr Tyr Tyr Ala Asp Ser Val Lys
1               5                   10                  15
Gly

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Trp Gly Asp Glu Gly Phe Asp Ile
1               5

<210> SEQ ID NO 149
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Arg Ala Ser Gln Gly Ile Ser Asn Trp Leu Ala
1               5                   10

<210> SEQ ID NO 150
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 150

Gly Ala Ser Ser Leu Gln Ser
1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gln Gln Tyr Ser Ser Phe Pro Thr Thr
1               5

<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Phe Thr Phe Ser Ser Tyr
1               5

<210> SEQ ID NO 153
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ser Ser Gln Gly Lys Ser
1               5

<210> SEQ ID NO 154
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Trp Gly Asp Glu Gly Phe Asp Ile
1               5

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ser Gln Gly Ile Ser Asn Trp
1               5
```

-continued

```
<210> SEQ ID NO 156
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gly Ala Ser
1

<210> SEQ ID NO 157
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Tyr Ser Ser Phe Pro Thr
1               5

<210> SEQ ID NO 158
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 159
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

Ser Ala Ile Ser Ser Gln Gly Lys Ser Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Gly Asp Glu Gly Phe Asp Ile Trp Gly Gln Gly Thr Leu
            100                 105                 110

Val Thr Val Ser Ser
        115

<210> SEQ ID NO 160
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 160
gatatccaga tgacccagag ccccagcagc ctgagcgcca gcgtgggcga cagagtgacc      60
atcacctgtc gggccagcca gggcatcagc aactggctgg cctggtatca gcagaagccc    120
ggcaaggccc ccaagctgct gatctacggc gccagctccc tgcagagcgg cgtgccaagc    180
agattcagcg gcagcggctc cggcaccgac ttcaccctga ccatcagcag cctgcagccc    240
gaggacttcg ccacctacta ctgccagcag tacagcagct cccccaccac cttcggccag    300
ggcaccaagg tggaaatcaa g                                              321

<210> SEQ ID NO 161
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 161
gaggtgcaat tgctggaaag cggcggaggc ctggtgcagc ctggcggcag cctgagactg      60
tcttgcgccg ccagcggctt caccttcagc agctacgcca tgagctgggt ccgccaggcc    120
cctggcaagg gactggaatg ggtgtccgcc atcagcagcc agggcaagag cacctactac    180
gccgacagcg tgaagggccg gttcaccatc agccgggaca acagcaagaa caccctgtac    240
ctgcagatga acagcctgcg ggccgaggac accgccgtgt actactgtgc cagatggggc    300
gacgagggct tcgacatctg gggccagggc accctggtca ccgtcagctc a             351

<210> SEQ ID NO 162
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile

```
                35                  40                  45
Tyr Gly Ala Ser Ser Leu Gln Ser Gly Val Pro Ser Arg Phe Ser Gly
 50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Ser Ser Phe Pro Thr
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 163
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Ser Gln Gly Lys Ser Thr Tyr Tyr Ala Asp Ser Val
    50                  55                  60
Lys Gly Arg Phe Thr Ile Ser Arg Asp Asn Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Trp Gly Asp Glu Gly Phe Asp Ile Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
```

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 164
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ser Tyr Ala Met Ser
1               5

<210> SEQ ID NO 165
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ala Ile Gly Ser Gln Gly Lys Ser Thr Tyr Tyr Ala Asp Ser Val Lys
1               5                   10                  15

Gly

<210> SEQ ID NO 166
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Trp Gly Asp Glu Gly Phe Asp Ile
1               5

<210> SEQ ID NO 167
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Arg Ala Ser Gln Gly Ile Ser Asn Trp Leu Ala
1               5                   10

<210> SEQ ID NO 168
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Gly Ala Ser Ser Leu Gln Ser
1               5

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gln Gln Tyr Ser Ser Phe Pro Thr Thr
1               5

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gly Phe Thr Phe Ser Ser Tyr
1               5

<210> SEQ ID NO 171
<211> LENGTH: 6
<212> TYPE: PRT
<213> ORGANISM: Artificial Sequence
<220> FEATURE:
<223> OTHER INFORMATION: Description of Artificial Sequence: Synthetic

```
                                peptide

<400> SEQUENCE: 171

Gly Ser Gln Gly Lys Ser
1               5

<210> SEQ ID NO 172
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Trp Gly Asp Glu Gly Phe Asp Ile
1               5

<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ser Gln Gly Ile Ser Asn Trp
1               5

<210> SEQ ID NO 174
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gly Ala Ser
1

<210> SEQ ID NO 175
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Tyr Ser Ser Phe Pro Thr
1               5

<210> SEQ ID NO 176
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30
```

Leu Ala Trp Tyr Gln Gln Lys Pro Gly Lys Ala Pro Lys Leu Leu Ile
         35                  40                  45

Tyr Gly Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Ser Phe Pro Thr
                 85                  90                  95

Thr Phe Gly Gln Gly Thr Lys Val Glu Ile Lys
            100                 105

<210> SEQ ID NO 177
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Gly Ser Gln Gly Lys Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Gly Asp Glu Gly Phe Asp Ile Trp Gly Gln Gly Thr Leu
            100                 105                 110

Val Thr Val Ser Ser
        115

<210> SEQ ID NO 178
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178
gatatccaga tgacccagag ccccagcagc ctgagcgcca gcgtgggcga cagagtgacc      60
atcacctgtc gggccagcca gggcatcagc aactggctgg cctggtatca gcagaagccc     120
ggcaaggccc ccaagctgct gatctacggc gccagctccc tgcagagcgg cgtgccaagc     180
agattcagcg gcagcggctc cggcaccgac ttcaccctga ccatcagcag cctgcagccc     240
gaggacttcg ccacctacta ctgccagcag tacagcagct cccccaccac cttcggccag     300
ggcaccaagg tggaaatcaa g                                               321

<210> SEQ ID NO 179
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 179

```
gaggtgcaat tgctggaaag cggcggaggc ctggtgcagc ctggcggcag cctgagactg       60
tcttgcgccg ccagcggctt caccttcagc agctacgcca tgagctgggt ccgccaggcc      120
cctggcaagg gactggaatg ggtgtccgcc atcggcagcc agggcaagag cacctactac      180
gccgacagcg tgaagggccg gttcaccatc agccgggaca acagcaagaa caccctgtac      240
ctgcagatga acagcctgcg ggccgaggac accgccgtgt actactgtgc cagatggggc      300
gacgagggct tcgacatctg gggccagggc accctggtca ccgtcagctc a               351
```

<210> SEQ ID NO 180
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 181
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Ser Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
```

```
                    405                 410                 415
Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 182
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ser Tyr Ala Met Ser
1               5

<210> SEQ ID NO 183
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ala Ile Ser Asn Gln Gly Lys Ser Thr Tyr Tyr Ala Asp Ser Val Lys
1               5                   10                  15
Gly

<210> SEQ ID NO 184
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Trp Gly Asp Glu Gly Phe Asp Ile
1               5

<210> SEQ ID NO 185
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Arg Ala Ser Gln Gly Ile Ser Asn Trp Leu Ala
1               5                   10

<210> SEQ ID NO 186
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Gly Ala Ser Ser Leu Gln Ser
1               5
```

```
<210> SEQ ID NO 187
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Gln Gln Tyr Ser Ser Phe Pro Thr Thr
1               5

<210> SEQ ID NO 188
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gly Phe Thr Phe Ser Ser Tyr
1               5

<210> SEQ ID NO 189
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Ser Asn Gln Gly Lys Ser
1               5

<210> SEQ ID NO 190
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Trp Gly Asp Glu Gly Phe Asp Ile
1               5

<210> SEQ ID NO 191
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ser Gln Gly Ile Ser Asn Trp
1               5

<210> SEQ ID NO 192
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 192

Gly Ala Ser
1

<210> SEQ ID NO 193
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Tyr Ser Ser Phe Pro Thr
1               5

<210> SEQ ID NO 194
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 195
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Asn Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                    85                  90                  95
Ala Arg Trp Gly Asp Glu Gly Phe Asp Ile Trp Gly Gln Gly Thr Leu
                100                 105                 110

Val Thr Val Ser Ser
        115

<210> SEQ ID NO 196
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 196
gatatccaga tgacccagag ccccagcagc ctgagcgcca gcgtgggcga cagagtgacc      60
atcacctgtc gggccagcca gggcatcagc aactggctgg cctggtatca gcagaagccc     120
ggcaaggccc ccaagctgct gatctacggc gccagctccc tgcagagcgg cgtgccaagc     180
agattcagcg gcagcggctc cggcaccgac ttcaccctga ccatcagcag cctgcagccc     240
gaggacttcg ccacctacta ctgccagcag tacagcagct cccccaccac cttcggccag     300
ggcaccaagg tggaaatcaa g                                               321

<210> SEQ ID NO 197
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 197
gaggtgcaat tgctggaaag cggcggaggc ctggtgcagc ctggcggcag cctgagactg      60
tcttgcgccg ccagcggctt caccttcagc agctacgcca tgagctgggt ccgccaggcc     120
cctggcaagg gactggaatg ggtgtccgcc atcagcaacc agggcaagag cacctactac     180
gccgacagcg tgaagggccg gttcaccatc agcggggaca cagcaagaa cacccctgtac     240 ctgcagatga acagcctgcg ggccgaggac accgccgtgt actactgtgc cagatggggc     300
gacgagggct cgacatctg ggcccagggc accctggtca ccgtcagctc a               351

<210> SEQ ID NO 198
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 199
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Asn Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His

```
            210                 215                 220
Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 200
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Ser Tyr Ala Met Ser
1               5

<210> SEQ ID NO 201
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Val Ile Ser Ser Gln Gly Lys Ser Thr Tyr Tyr Ala Asp Ser Val Lys
1               5                   10                  15

Gly

<210> SEQ ID NO 202
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 202

Trp Gly Asp Glu Gly Phe Asp Ile
1               5

<210> SEQ ID NO 203
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Arg Ala Ser Gln Gly Ile Ser Asn Trp Leu Ala
1               5                   10

<210> SEQ ID NO 204
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Gly Ala Ser Ser Leu Gln Ser
1               5

<210> SEQ ID NO 205
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Gln Gln Tyr Ser Ser Phe Pro Thr Thr
1               5

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gly Phe Thr Phe Ser Ser Tyr
1               5

<210> SEQ ID NO 207
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ser Ser Gln Gly Lys Ser
1               5
```

```
<210> SEQ ID NO 208
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Trp Gly Asp Glu Gly Phe Asp Ile
1               5

<210> SEQ ID NO 209
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ser Gln Gly Ile Ser Asn Trp
1               5

<210> SEQ ID NO 210
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gly Ala Ser
1

<210> SEQ ID NO 211
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Tyr Ser Ser Phe Pro Thr
1               5

<210> SEQ ID NO 212
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 213
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Val Ile Ser Ser Gln Gly Lys Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
        115

<210> SEQ ID NO 214
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 214
gatatccaga tgacccagag cccccagcagc ctgagcgcca gcgtgggcga cagagtgacc      60
atcacctgtc gggccagcca gggcatcagc aactggctgg cctggtatca gcagaagccc     120
ggcaaggccc ccaagctgct gatctacggc gccagctccc tgcagagcgg cgtgccaagc     180
agattcagcg gcagcggctc cggcaccgac ttcaccctga ccatcagcag cctgcagccc     240
gaggacttcg ccacctacta ctgccagcag tacagcagct cccccaccac cttcggccag     300
ggcaccaagg tggaaatcaa g                                               321

<210> SEQ ID NO 215
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 215
gaggtgcaat tgctggaaag cggcggaggc ctggtgcagc ctggcggcag cctgagactg      60

```
tcttgcgccg ccagcggctt caccttcagc agctacgcca tgagctgggt ccgccaggcc    120
cctggcaagg gactggaatg ggtgtccgtc atcagcagcc agggcaagag cacctactac    180
gccgacagcg tgaagggccg gttcaccatc agccgggaca acagcaagaa caccctgtac    240
ctgcagatga acagcctgcg ggccgaggac accgccgtgt actactgtgc cagatggggc    300
gacgagggct tcgacatctg gggccagggc accctggtca ccgtcagctc a            351
```

<210> SEQ ID NO 216
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 217
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
              20                  25                  30
Ala Met Ser Trp Val Arg Gln Ala Pro Gly Lys Gly Leu Glu Trp Val
             35                  40                  45
Ser Val Ile Ser Ser Gln Gly Lys Ser Thr Tyr Tyr Ala Asp Ser Val
             50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Trp Gly Asp Glu Gly Phe Asp Ile Trp Gly Gln Gly Thr Leu
                100                 105                 110
Val Thr Val Ser Ser Ala Ser Thr Lys Gly Pro Ser Val Phe Pro Leu
                115                 120                 125
Ala Pro Ser Ser Lys Ser Thr Ser Gly Gly Thr Ala Ala Leu Gly Cys
                130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
                180                 185                 190
Leu Gly Thr Gln Thr Tyr Ile Cys Asn Val Asn His Lys Pro Ser Asn
                195                 200                 205
Thr Lys Val Asp Lys Arg Val Glu Pro Lys Ser Cys Asp Lys Thr His
                210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
                260                 265                 270
Val Lys Phe Asn Trp Tyr Val Asp Gly Val Glu Val His Asn Ala Lys
                275                 280                 285
Thr Lys Pro Arg Glu Glu Gln Tyr Asn Ser Thr Tyr Arg Val Val Ser
                290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Arg Glu Glu Met Thr Lys Asn Gln Val Ser Leu Thr Cys Leu
                355                 360                 365
Val Lys Gly Phe Tyr Pro Ser Asp Ile Ala Val Glu Trp Glu Ser Asn
                370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
                420                 425                 430
His Asn His Tyr Thr Gln Lys Ser Leu Ser Leu Ser Pro Gly Lys
                435                 440                 445
```

```
<210> SEQ ID NO 218
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ser Tyr Ala Met Ser
1               5

<210> SEQ ID NO 219
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Val Ile Gly Ser Gln Gly Lys Ser Thr Tyr Tyr Ala Asp Ser Val Lys
1               5                   10                  15

Gly

<210> SEQ ID NO 220
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Trp Gly Asp Glu Gly Phe Asp Ile
1               5

<210> SEQ ID NO 221
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Arg Ala Ser Gln Gly Ile Ser Asn Trp Leu Ala
1               5                   10

<210> SEQ ID NO 222
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gly Ala Ser Ser Leu Gln Ser
1               5

<210> SEQ ID NO 223
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 223

Gln Gln Tyr Ser Ser Phe Pro Thr Thr
1               5

<210> SEQ ID NO 224
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Gly Phe Thr Phe Ser Ser Tyr
1               5

<210> SEQ ID NO 225
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Gly Ser Gln Gly Lys Ser
1               5

<210> SEQ ID NO 226
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Trp Gly Asp Glu Gly Phe Asp Ile
1               5

<210> SEQ ID NO 227
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Ser Gln Gly Ile Ser Asn Trp
1               5

<210> SEQ ID NO 228
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gly Ala Ser
1
```

```
<210> SEQ ID NO 229
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Tyr Ser Ser Phe Pro Thr
1               5

<210> SEQ ID NO 230
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 231
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Gly Ser Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
            115
```

<210> SEQ ID NO 232
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 232

```
gatatccaga tgacccagag ccccagcagc ctgagcgcca gcgtgggcga cagagtgacc      60
atcacctgtc gggccagcca gggcatcagc aactggctgg cctggtatca gcagaagccc     120
ggcaaggccc ccaagctgct gatctacggc gccagctccc tgcagagcgg cgtgccaagc     180
agattcagcg gcagcggctc cggcaccgac ttcaccctga ccatcagcag cctgcagccc     240
gaggacttcg ccacctacta ctgccagcag tacagcagct cccccaccac cttcggccag     300
ggcaccaagg tggaaatcaa g                                               321
```

<210> SEQ ID NO 233
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 233

```
gaggtgcaat tgctggaaag cggcggaggc ctggtgcagc ctggcggcag cctgagactg      60
tcttgcgccg ccagcggctt caccttcagc agctacgcca tgagctgggt ccgccaggcc     120
cctggcaagg gactggaatg ggtgtccgtc atcggcagcc agggcaagag cacctactac     180
gccgacagcg tgaagggccg gttcaccatc agccgggaca cagcaagaa caccctgtac      240
ctgcagatga acagcctgcg ggccgaggac accgccgtgt actactgtgc cagatggggc     300
gacgagggct cgacatctg gggccagggc accctggtca ccgtcagctc a              351
```

<210> SEQ ID NO 234
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Ser Pro Thr
                85                  90                  95

Thr Phe Gly Gln Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 235
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Gly Ser Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255
```

```
Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 236
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ser Tyr Ala Met Ser
1               5

<210> SEQ ID NO 237
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Ala Ile Asn Ala Gln Gly Lys Ser Thr Tyr Tyr Ala Asp Ser Val Lys
1               5                   10                  15

Gly

<210> SEQ ID NO 238
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Trp Gly Asp Glu Gly Phe Asp Ile
```

```
<210> SEQ ID NO 239
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Arg Ala Ser Gln Gly Ile Ser Asn Trp Leu Ala
1               5                   10

<210> SEQ ID NO 240
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gly Ala Ser Ser Leu Gln Ser
1               5

<210> SEQ ID NO 241
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Gln Gln Tyr Ser Ser Phe Pro Thr Thr
1               5

<210> SEQ ID NO 242
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gly Phe Thr Phe Ser Ser Tyr
1               5

<210> SEQ ID NO 243
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Asn Ala Gln Gly Lys Ser
1               5

<210> SEQ ID NO 244
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                                     peptide

<400> SEQUENCE: 244

Trp Gly Asp Glu Gly Phe Asp Ile
1               5

<210> SEQ ID NO 245
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Ser Gln Gly Ile Ser Asn Trp
1               5

<210> SEQ ID NO 246
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Gly Ala Ser
1

<210> SEQ ID NO 247
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Tyr Ser Ser Phe Pro Thr
1               5

<210> SEQ ID NO 248
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
```

<210> SEQ ID NO 249
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 249

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
        115

<210> SEQ ID NO 250
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 250
gatatccaga tgacccagag ccccagcagc ctgagcgcca gcgtgggcga cagagtgacc      60
atcacctgtc gggccagcca gggcatcagc aactggctgg cctggtatca gcagaagccc     120
ggcaaggccc ccaagctgct gatctacggc gccagctccc tgcagagcgg cgtgccaagc     180
agattcagcg gcagcggctc cggcaccgac ttcaccctga ccatcagcag cctgcagccc     240
gaggacttcg ccacctacta ctgccagcag tacagcagct cccccaccac cttcggccag     300
ggcaccaagg tggaaatcaa g                                               321

<210> SEQ ID NO 251
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 251
gaggtgcaat tgctggaaag cggcggaggc ctggtgcagc ctggcggcag cctgagactg      60
tcttgcgccg ccagcggctt caccttcagc agctacgcca tgagctgggt ccgccaggcc     120
cctggcaagg gactggaatg ggtgtccgcc atcaacgccc agggcaagag cacctactac     180
gccgacagcg tgaagggccg gttcaccatc agccgggaca acagcaagaa caccctgtac     240

-continued

```
ctgcagatga acagcctgcg ggccgaggac accgccgtgt actactgtgc cagatggggc    300
gacgagggct tcgacatctg ggccagggc accctggtca ccgtcagctc a              351
```

<210> SEQ ID NO 252
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 253
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Gln Gly Lys Ser Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 254
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 254

Ser Tyr Ala Met Ser
1               5

<210> SEQ ID NO 255
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Ala Ile Asn Thr Gln Gly Lys Ser Thr Tyr Tyr Ala Asp Ser Val Lys
1               5                   10                  15

Gly

<210> SEQ ID NO 256
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Trp Gly Asp Glu Gly Phe Asp Ile
1               5

<210> SEQ ID NO 257
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Arg Ala Ser Gln Gly Ile Ser Asn Trp Leu Ala
1               5                   10

<210> SEQ ID NO 258
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Gly Ala Ser Ser Leu Gln Ser
1               5

<210> SEQ ID NO 259
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Gln Gln Tyr Ser Ser Phe Pro Thr Thr
1               5
```

<210> SEQ ID NO 260
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Gly Phe Thr Phe Ser Ser Tyr
1               5

<210> SEQ ID NO 261
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Asn Thr Gln Gly Lys Ser
1               5

<210> SEQ ID NO 262
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Trp Gly Asp Glu Gly Phe Asp Ile
1               5

<210> SEQ ID NO 263
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Ser Gln Gly Ile Ser Asn Trp
1               5

<210> SEQ ID NO 264
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Gly Ala Ser
1

<210> SEQ ID NO 265
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Tyr Ser Ser Phe Pro Thr
1               5

<210> SEQ ID NO 266
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 267
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Thr Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
        115

<210> SEQ ID NO 268
<211> LENGTH: 321
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 268

```
gatatccaga tgacccagag ccccagcagc ctgagcgcca gcgtgggcga cagagtgacc    60
atcacctgtc gggccagcca gggcatcagc aactggctgg cctggtatca gcagaagccc   120
ggcaaggccc ccaagctgct gatctacggc gccagctccc tgcagagcgg cgtgccaagc   180
agattcagcg gcagcggctc cggcaccgac ttcaccctga ccatcagcag cctgcagccc   240
gaggacttcg ccacctacta ctgccagcag tacagcagct cccccaccac cttcggccag   300
ggcaccaagg tggaaatcaa g                                              321
```

<210> SEQ ID NO 269
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 269

```
gaggtgcaat tgctggaaag cggcggaggc ctggtgcagc ctggcggcag cctgagactg    60
tcttgcgccg ccagcggctt caccttcagc agctacgcca tgagctgggt ccgccaggcc   120
cctggcaagg gactggaatg ggtgtccgcc atcaacaccc agggcaagag cacctactac   180
gccgacagcg tgaagggccg gttcaccatc agccgggaca cagcaagaa caccctgtac   240
ctgcagatga acagcctgcg ggccgaggac accgccgtgt actactgtgc cagatggggc   300
gacgagggct tcgacatctg gggccagggc accctggtca ccgtcagctc a            351
```

<210> SEQ ID NO 270
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Ser Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
        145                 150                 155                 160
Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 271
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Thr Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285
```

-continued

```
Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 272
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

```
Ser Tyr Ala Met Ser
1               5
```

<210> SEQ ID NO 273
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

```
Val Thr Gly Ala Val Gly Ser Ser Thr Tyr Tyr Pro Asp Ser Val Lys
1               5                   10                  15

Gly
```

<210> SEQ ID NO 274
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

```
Trp Gly Asp Glu Gly Phe Asp Ile
1               5
```

<210> SEQ ID NO 275
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 275

Arg Ala Ser Gln Gly Ile Ser Asn Trp Leu Ala
1               5                   10

<210> SEQ ID NO 276
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Gly Ala Ser Ser Leu Gln Ser
1               5

<210> SEQ ID NO 277
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Gln Gln Tyr Ser Ser Phe Pro Thr Thr
1               5

<210> SEQ ID NO 278
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Gly Phe Thr Phe Ser Ser Tyr
1               5

<210> SEQ ID NO 279
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Gly Ala Val Gly Ser Ser
1               5

<210> SEQ ID NO 280
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Trp Gly Asp Glu Gly Phe Asp Ile
1               5
```

<210> SEQ ID NO 281
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Ser Gln Gly Ile Ser Asn Trp
1               5

<210> SEQ ID NO 282
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Gly Ala Ser
1

<210> SEQ ID NO 283
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Tyr Ser Ser Phe Pro Thr
1               5

<210> SEQ ID NO 284
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 285
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Ser Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
        115
```

<210> SEQ ID NO 286
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 286

```
gatatccaga tgacccagag ccccagcagc ctgagcgcca gcgtgggcga cagagtgacc       60
atcacctgtc gggccagcca gggcatcagc aactggctgg cctggtatca gcagaagccc      120
ggcaaggccc ccaagctgct gatctacggc gccagctccc tgcagagcgg cgtgccaagc      180
agattcagcg gcagcggctc cggcaccgac ttcaccctga ccatcagcag cctgcagccc      240
gaggacttcg ccacctacta ctgccagcag tacagcagct cccccaccac cttcggccag      300
ggcaccaagg tggaaatcaa g                                                 321
```

<210> SEQ ID NO 287
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 287

```
gaggtgcaat tgctggaaag cggcggaggc ctggtgcagc ctggcggcag cctgagactg       60
tcttgcgccg ccagcggctt caccttcagc agctacgcca tgagctgggt ccgccaggcc      120
cctggcaagg gactggaatg ggtgtccgtg acaggcgccg tgggcagcag cacctactac      180
cccgacagcg tgaagggccg gttcaccatc agccgggaca acagcaagaa caccctgtac      240
ctgcagatga acagcctgcg ggccgaggac accgccgtgt actactgtgc cagatggggc      300
gacgagggct tcgacatctg gggccagggc accctggtca ccgtcagctc a               351
```

<210> SEQ ID NO 288
<211> LENGTH: 214

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 288

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 289
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Ser Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 290
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Ser Tyr Ala Met Ser
1               5
```

<210> SEQ ID NO 291
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Val Thr Gly Ala Val Gly Gly Ser Thr Tyr Tyr Pro Asp Ser Val Lys
1               5                   10                  15

Gly

<210> SEQ ID NO 292
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Trp Gly Asp Glu Gly Phe Asp Ile
1               5

<210> SEQ ID NO 293
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Arg Ala Ser Gln Gly Ile Ser Asn Trp Leu Ala
1               5                   10

<210> SEQ ID NO 294
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Gly Ala Ser Ser Leu Gln Ser
1               5

<210> SEQ ID NO 295
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Gln Gln Tyr Ser Ser Phe Pro Thr Thr
1               5

<210> SEQ ID NO 296
<211> LENGTH: 7
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 296

Gly Phe Thr Phe Ser Ser Tyr
1               5

<210> SEQ ID NO 297
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Gly Ala Val Gly Gly Ser
1               5

<210> SEQ ID NO 298
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Trp Gly Asp Glu Gly Phe Asp Ile
1               5

<210> SEQ ID NO 299
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Ser Gln Gly Ile Ser Asn Trp
1               5

<210> SEQ ID NO 300
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Gly Ala Ser
1

<210> SEQ ID NO 301
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Tyr Ser Ser Phe Pro Thr
1               5
```

```
<210> SEQ ID NO 302
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 303
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Gly Ser Thr Tyr Tyr Pro Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
        115

<210> SEQ ID NO 304
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 304
gatatccaga tgacccagag ccccagcagc ctgagcgcca gcgtgggcga cagagtgacc      60
```

```
atcacctgtc gggccagcca gggcatcagc aactggctgg cctggtatca gcagaagccc    120
ggcaaggccc ccaagctgct gatctacggc gccagctccc tgcagagcgg cgtgccaagc    180
agattcagcg gcagcggctc cggcaccgac ttcaccctga ccatcagcag cctgcagccc    240
gaggacttcg ccacctacta ctgccagcag tacagcagct cccccaccac cttcggccag    300
ggcaccaagg tggaaatcaa g                                              321
```

<210> SEQ ID NO 305
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 305

```
gaggtgcaat tgctggaaag cggcggaggc ctggtgcagc ctggcggcag cctgagactg    60
tcttgcgccg ccagcggctt caccttcagc agctacgcca tgagctgggt ccgccaggcc    120
cctggcaagg gactggaatg ggtgtccgtg acaggcgccg tgggcggaag cacctactac    180
cccgacagcg tgaagggccg gttcaccatc agccgggaca cagcaagaa cacccctgtac    240 ctgcagatga acagcctgcg ggccgaggac accgccgtgt actactgtgc cagatggggc    300
gacgagggct tcgacatctg gggccagggc accctggtca ccgtcagctc a             351
```

<210> SEQ ID NO 306
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
    195                 200                 205

Phe Asn Arg Gly Glu Cys
    210

<210> SEQ ID NO 307
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile

```
                    325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
            435                 440                 445

<210> SEQ ID NO 308
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Ser Tyr Ala Met Ser
1               5

<210> SEQ ID NO 309
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Val Thr Gly Ala Val Gly Lys Ser Thr Tyr Tyr Pro Asp Ser Val Lys
1               5                   10                  15
Gly

<210> SEQ ID NO 310
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Trp Gly Asp Glu Gly Phe Asp Ile
1               5

<210> SEQ ID NO 311
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Arg Ala Ser Gln Gly Ile Ser Asn Trp Leu Ala
```

```
1               5                   10
```

<210> SEQ ID NO 312
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Gly Ala Ser Ser Leu Gln Ser
1               5

<210> SEQ ID NO 313
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Gln Gln Tyr Ser Ser Phe Pro Thr Thr
1               5

<210> SEQ ID NO 314
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Gly Phe Thr Phe Ser Ser Tyr
1               5

<210> SEQ ID NO 315
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Gly Ala Val Gly Lys Ser
1               5

<210> SEQ ID NO 316
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Trp Gly Asp Glu Gly Phe Asp Ile
1               5

<210> SEQ ID NO 317
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 317

Ser Gln Gly Ile Ser Asn Trp
1               5

<210> SEQ ID NO 318
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Gly Ala Ser
1

<210> SEQ ID NO 319
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Tyr Ser Ser Phe Pro Thr
1               5

<210> SEQ ID NO 320
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 320

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 321
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Glu Val Gln Leu Leu Glu Ser Gly Gly Gly Leu Val Gln Pro Gly Gly

```
                1               5                  10                 15
              Ser Leu Arg Leu Ser Cys Ala Ala Ser Gly Phe Thr Phe Ser Ser Tyr
                           20                  25                  30

Ala Met Ser Trp Val Arg Gln Ala Pro Gly Lys Gly Leu Glu Trp Val
                           35                  40                  45

Ser Val Thr Gly Ala Val Gly Lys Ser Thr Tyr Tyr Pro Asp Ser Val
                           50                  55                  60

Lys Gly Arg Phe Thr Ile Ser Arg Asp Asn Ser Lys Asn Thr Leu Tyr
              65                       70                  75                  80

Leu Gln Met Asn Ser Leu Arg Ala Glu Asp Thr Ala Val Tyr Tyr Cys
                           85                  90                  95

Ala Arg Trp Gly Asp Glu Gly Phe Asp Ile Trp Gly Gln Gly Thr Leu
                           100                 105                 110

Val Thr Val Ser Ser
                           115

<210> SEQ ID NO 322
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 322
gatatccaga tgacccagag ccccagcagc ctgagcgcca gcgtgggcga cagagtgacc        60
atcacctgtc gggccagcca gggcatcagc aactggctgg cctggtatca gcagaagccc       120
ggcaaggccc ccaagctgct gatctacggc gccagctccc tgcagagcgg cgtgccaagc       180
agattcagcg gcagcggctc cggcaccgac ttcaccctga ccatcagcag cctgcagccc       240
gaggacttcg ccacctacta ctgccagcag tacagcagct cccccaccac cttcggccag       300
ggcaccaagg tggaaatcaa g                                                  321

<210> SEQ ID NO 323
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 323
gaggtgcaat tgctggaaag cggcggaggc ctggtgcagc ctggcggcag cctgagactg        60
tcttgcgccg ccagcggctt caccttcagc agctacgcca tgagctgggt ccgccaggcc       120
cctggcaagg gactggaatg ggtgtccgtg acaggcgccg tgggcaaaag cacctactac       180
cccgacagcg tgaagggccg gttcaccatc agccgggaca acagcaagaa caccctgtac       240
ctgcagatga acagcctgcg ggccgaggac accgccgtgt actactgtgc cagatggggc       300
gacgagggct tcgacatctg gggccagggc accctggtca ccgtcagctc a                351

<210> SEQ ID NO 324
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 325
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Lys Ser Thr Tyr Tyr Pro Asp Ser Val
50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
```

```
                130                 135                 140
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Arg Val Glu Pro Lys Ser Cys Asp Lys Thr His
                210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Asn Ser Thr Tyr Arg Val Val Ser
                290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 326
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Ser Tyr Ala Met Ser
1               5

<210> SEQ ID NO 327
<211> LENGTH: 16
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 327

Val Thr Gly Ala Val Gly Arg Thr Tyr Tyr Pro Asp Ser Val Lys Gly
1               5                   10                  15

<210> SEQ ID NO 328
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Trp Gly Asp Glu Gly Phe Asp Ile
1               5

<210> SEQ ID NO 329
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Arg Ala Ser Gln Gly Ile Ser Asn Trp Leu Ala
1               5                   10

<210> SEQ ID NO 330
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Gly Ala Ser Ser Leu Gln Ser
1               5

<210> SEQ ID NO 331
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Gln Gln Tyr Ser Ser Phe Pro Thr Thr
1               5

<210> SEQ ID NO 332
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Gly Phe Thr Phe Ser Ser Tyr
1               5

```
<210> SEQ ID NO 333
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Gly Ala Val Gly Arg Thr
1               5

<210> SEQ ID NO 334
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Trp Gly Asp Glu Gly Phe Asp Ile
1               5

<210> SEQ ID NO 335
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Ser Gln Gly Ile Ser Asn Trp
1               5

<210> SEQ ID NO 336
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Gly Ala Ser
1

<210> SEQ ID NO 337
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Tyr Ser Ser Phe Pro Thr
1               5

<210> SEQ ID NO 338
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Ser Ser Phe Pro Thr
            85                  90                  95

Thr Phe Gly Gln Gly Thr Lys Val Glu Ile Lys
            100                 105
```

<210> SEQ ID NO 339
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Arg Thr Tyr Tyr Pro Asp Ser Val Lys
    50                  55                  60

Gly Arg Phe Thr Ile Ser Arg Asp Asn Ser Lys Asn Thr Leu Tyr Leu
65              70                  75                  80

Gln Met Asn Ser Leu Arg Ala Glu Asp Thr Ala Val Tyr Tyr Cys Ala
            85                  90                  95

Arg Trp Gly Asp Glu Gly Phe Asp Ile Trp Gly Gln Gly Thr Leu Val
            100                 105                 110

Thr Val Ser Ser
        115
```

<210> SEQ ID NO 340
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 340

```
gatatccaga tgacccagag ccccagcagc ctgagcgcca gcgtgggcga cagagtgacc      60
atcacctgtc gggccagcca gggcatcagc aactggctgg cctggtatca gcagaagccc     120
ggcaaggccc ccaagctgct gatctacggc gccagctccc tgcagagcgg cgtgccaagc     180
agattcagcg gcagcggctc cggcaccgac ttcaccctga ccatcagcag cctgcagccc     240
gaggacttcg ccacctacta ctgccagcag tacagcagct cccccaccac cttcggccag     300
ggcaccaagg tggaaatcaa g                                               321
```

<210> SEQ ID NO 341
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 341
gaggtgcaat tgctggaaag cggcggaggc ctggtgcagc ctggcggcag cctgagactg     60
tcttgcgccg ccagcggctt caccttcagc agctacgcca tgagctgggt ccgccaggcc    120
cctggcaagg gactggaatg ggtgtccgtg acaggcgccg tgggcagaac ctactacccc    180
gacagcgtga agggccggtt caccatcagc cgggacaaca gcaagaacac cctgtacctg    240
cagatgaaca gcctgcgggc cgaggacacc gccgtgtact actgtgccag atggggcgac    300
gagggcttcg acatctgggg ccagggcacc ctggtcaccg tcagctca                348

<210> SEQ ID NO 342
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 342

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 343

```
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 343

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Arg Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Trp Gly Asp Glu Gly Phe Asp Ile Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
```

```
                    370                 375                 380
Gln Pro Glu Asn Asn Tyr Lys Thr Thr Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 344
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Ser Tyr Ala Met Ser
1               5

<210> SEQ ID NO 345
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Val Ile Asn Gly Leu Gly Tyr Thr Thr Phe Tyr Ala Asp Ser Val Lys
1               5                   10                  15

Gly

<210> SEQ ID NO 346
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Trp Gly Asp Glu Gly Phe Asp Ile
1               5

<210> SEQ ID NO 347
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Arg Ala Ser Gln Gly Ile Ser Asn Trp Leu Ala
1               5                   10

<210> SEQ ID NO 348
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 348

Gly Ala Ser Ser Leu Gln Ser
1               5

<210> SEQ ID NO 349
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Gln Gln Tyr Ser Ser Phe Pro Thr Thr
1               5

<210> SEQ ID NO 350
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Gly Phe Thr Phe Ser Ser Tyr
1               5

<210> SEQ ID NO 351
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Asn Gly Leu Gly Tyr Thr
1               5

<210> SEQ ID NO 352
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Trp Gly Asp Glu Gly Phe Asp Ile
1               5

<210> SEQ ID NO 353
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Ser Gln Gly Ile Ser Asn Trp
1               5

<210> SEQ ID NO 354

-continued

```
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Gly Ala Ser
1

<210> SEQ ID NO 355
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Tyr Ser Ser Phe Pro Thr
1               5

<210> SEQ ID NO 356
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 356

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 357
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 357

Gln Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Asn Gly Leu Gly Tyr Thr Thr Phe Tyr Ala Asp Ser Val
```

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Gly Asp Glu Gly Phe Asp Ile Trp Gly Gln Gly Thr Leu
            100                 105                 110

Val Thr Val Ser Ser
            115
```

<210> SEQ ID NO 358
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 358
gatatccaga tgacccagag cccgtctagc ctgagcgcga gcgtgggtga tcgtgtgacc      60
attacctgca gagcgagcca gggtatttct aattggctgg cttggtacca gcagaaacca     120
ggtaaagcac cgaaactatt aatttatggt gcttcttctt tgcaaagcgg ggtcccgtcc     180
cgttttagcg gctctggatc cggcactgat tttaccctga ccattagcag cctgcaacct     240
gaagactttg cggtttatta ttgccagcag tattcttctt ttcctactac ctttggccag     300
ggtacgaaag ttgaaattaa a                                               321

<210> SEQ ID NO 359
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 359
caggtgcaat tggtggaaag cggcggcggc ctggtgcaac gggcggcag cctgcgtctg       60 agctgcgcgg cctccggatt tacctttagc agctatgcga tgagctgggt gcgccaagcc    120
cctgggaagg gtctcgagtg ggtgagcgtt attaatggtc ttggttatac tactttttat    180
gctgattctg ttaagggtcg ttttaccatt tcacgtgata attcgaaaaa caccctgtat    240
ctgcaaatga acagcctgcg tgcggaagat acggccgtgt attattgcgc gcgttggggt    300
gatgagggtt ttgatatttg gggccaaggc accctggtga cggttagctc a             351

<210> SEQ ID NO 360
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 360

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Asn Trp
             20                  25                  30

Leu Ala Trp Tyr Gln Gln Lys Pro Gly Lys Ala Pro Lys Leu Leu Ile
         35                  40                  45
```

```
Tyr Gly Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Val Tyr Tyr Cys Gln Gln Tyr Ser Ser Phe Pro Thr
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 361
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 361

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Val Ile Asn Gly Leu Gly Tyr Thr Thr Phe Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Gly Asp Glu Gly Phe Asp Ile Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
```

```
                    180                 185                 190
Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
        435                 440                 445

<210> SEQ ID NO 362
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Ser Tyr Ala Met Ser
1               5

<210> SEQ ID NO 363
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Gly Thr Gly Pro Tyr Gly Gly Thr Tyr Tyr Pro Asp Ser Val Lys Gly
1               5                   10                  15
```

```
<210> SEQ ID NO 364
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Trp Gly Asp Glu Gly Phe Asp Ile
1               5

<210> SEQ ID NO 365
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Arg Ala Ser Gln Gly Ile Ser Asn Trp Leu Ala
1               5                   10

<210> SEQ ID NO 366
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Gly Ala Ser Ser Leu Gln Ser
1               5

<210> SEQ ID NO 367
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Gln Gln Tyr Ser Ser Phe Pro Thr Thr
1               5

<210> SEQ ID NO 368
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Gly Phe Thr Phe Ser Ser Tyr
1               5

<210> SEQ ID NO 369
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369
```

-continued

Gly Pro Tyr Gly Gly
1               5

<210> SEQ ID NO 370
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Trp Gly Asp Glu Gly Phe Asp Ile
1               5

<210> SEQ ID NO 371
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Ser Gln Gly Ile Ser Asn Trp
1               5

<210> SEQ ID NO 372
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Gly Ala Ser
1

<210> SEQ ID NO 373
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Tyr Ser Ser Phe Pro Thr
1               5

<210> SEQ ID NO 374
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 374

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

```
Tyr Gly Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Val Tyr Tyr Cys Gln Gln Tyr Ser Ser Phe Pro Thr
                 85                  90                  95

Thr Phe Gly Gln Gly Thr Lys Val Glu Ile Lys
            100                 105

<210> SEQ ID NO 375
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 375

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Thr Gly Pro Tyr Gly Gly Thr Tyr Tyr Pro Asp Ser Val Lys
    50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Trp Gly Asp Glu Gly Phe Asp Ile Trp Gly Gln Gly Thr Leu Val
            100                 105                 110

Thr Val Ser Ser
        115

<210> SEQ ID NO 376
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 376
gatatccaga tgacccagag cccgtctagc ctgagcgcga gcgtgggtga tcgtgtgacc        60
attacctgca gagcgagcca gggtatttct aatttggctgg cttggtacca gcagaaacca      120
ggtaaagcac cgaaactatt aatttatggt gcttcttctt tgcaaagcgg ggtcccgtcc      180
cgttttagcg gctctggatc cggcactgat tttaccctga ccattagcag cctgcaacct      240
gaagactttg cggtttatta ttgccagcag tattcttctt ttcctactac ctttggccag      300
ggtacgaaag ttgaaattaa a                                                 321

<210> SEQ ID NO 377
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 377

```
caggtgcaat tggtggaaag cggcggcggc ctggtgcaac cgggcggcag cctgcgtctg      60
agctgcgcgg cctccggatt tacctttagc agctatgcga tgagctgggt gcgccaagcc     120
cctgggaagg gtctcgagtg ggtgagcggt actggtcctt atggtggtac ttattatcct     180
gattctgtta agggtcgttt taccatttca cgtgataatt cgaaaaacac cctgtatctg     240
caaatgaaca gcctgcgtgc ggaagatacg gccgtgtatt attgcgcgcg ttggggtgat     300
gagggttttg atatttgggg ccaaggcacc ctggtgacgg ttagctca                  348
```

<210> SEQ ID NO 378
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 378

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 379
<211> LENGTH: 446
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 379

-continued

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Thr Gly Pro Tyr Gly Gly Thr Tyr Tyr Pro Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Trp Gly Asp Glu Gly Phe Asp Ile Trp Gly Gln Gly Thr Leu Val
        100                 105                 110

Thr Val Ser Ser Ala Ser Thr Lys Gly Pro Ser Val Phe Pro Leu Ala
    115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415
```

```
Gln Gln Gly Asn Val Phe Ser Cys Ser Val Met His Glu Ala Leu His
            420             425             430
Asn His Tyr Thr Gln Lys Ser Leu Ser Leu Ser Pro Gly Lys
        435             440             445
```